US009660196B2

(12) United States Patent
Abbotto et al.

(10) Patent No.: US 9,660,196 B2
(45) Date of Patent: May 23, 2017

(54) ORGANIC DYE FOR A DYE-SENSITIZED SOLAR CELL

(71) Applicant: ENI S.P.A., Rome (IT)

(72) Inventors: Alessandro Abbotto, Milan (IT); Maurizio Filippo Acciarri, Milan (IT); Paolo Biagini, San Giuliano Terme (IT); Simona Olga Binetti, Milan (IT)

(73) Assignee: ENI S.p.A., Rome (IT)

( * ) Notice: Subject to any disclaimer, the term of this patent is extended or adjusted under 35 U.S.C. 154(b) by 0 days.

(21) Appl. No.: 14/428,659

(22) PCT Filed: Oct. 4, 2013

(86) PCT No.: PCT/EP2013/070683
§ 371 (c)(1),
(2) Date: Mar. 17, 2015

(87) PCT Pub. No.: WO2014/053626
PCT Pub. Date: Apr. 10, 2014

(65) Prior Publication Data
US 2015/0221871 A1 Aug. 6, 2015

(30) Foreign Application Priority Data
Oct. 5, 2012 (IT) .............. MI2012A1672

(51) Int. Cl.
H01G 9/20 (2006.01)
H01L 51/00 (2006.01)
C07D 333/24 (2006.01)
C07D 495/04 (2006.01)
C07D 519/00 (2006.01)
C09B 57/00 (2006.01)
C09B 23/10 (2006.01)
H01L 51/42 (2006.01)

(52) U.S. Cl.
CPC ........ H01L 51/0061 (2013.01); C07D 333/24 (2013.01); C07D 495/04 (2013.01); C07D 519/00 (2013.01); C09B 23/105 (2013.01); C09B 57/00 (2013.01); C09B 57/008 (2013.01); H01G 9/2004 (2013.01); H01G 9/2027 (2013.01); H01G 9/2059 (2013.01); H01L 51/0064 (2013.01); H01L 51/422 (2013.01); H01L 51/0068 (2013.01); H01L 51/0071 (2013.01); H01L 51/0074 (2013.01); Y02E 10/542 (2013.01); Y02E 10/549 (2013.01)

(58) Field of Classification Search
CPC .................. H01G 9/2059; H01G 9/20
See application file for complete search history.

(56) References Cited

U.S. PATENT DOCUMENTS 2,803,640 A * 8/1957 Heckert ............. C07C 255/00
544/301
4,927,721 A * 5/1990 Gratzel ............. H01G 9/2031
429/111
5,670,091 A * 9/1997 Marder ................ B82Y 30/00
252/582
6,084,176 A * 7/2000 Shiratsuchi ........ H01L 51/0059
136/248
6,245,988 B1* 6/2001 Gratzel .................. C07F 9/587
136/252
6,291,763 B1* 9/2001 Nakamura .......... H01G 9/2009
136/252
6,335,481 B1* 1/2002 Watanabe .......... H01L 51/0064
136/263
6,376,765 B1* 4/2002 Wariishi ............. H01G 9/2009
136/256
7,943,848 B2* 5/2011 Nishimura .......... H01L 51/0059
136/252
7,947,898 B2* 5/2011 Itami .................. H01L 51/0059
136/252
7,977,570 B2* 7/2011 Shigaki .............. C09B 23/0066
136/250
8,022,294 B2* 9/2011 Shigaki ................ C07D 471/06
136/250
8,039,741 B2* 10/2011 Itami .................. H01L 51/0059
136/252
2002/0010969 A1* 1/2002 Goettel .................. A61K 8/494
8/405
2003/0152827 A1* 8/2003 Ikeda .................... H01L 51/005
429/111
2004/0074532 A1* 4/2004 Ikeda .................... H01L 51/005
136/250

(Continued)

FOREIGN PATENT DOCUMENTS

CN 101735640 A 6/2010
EP 1311001 A1 5/2003

OTHER PUBLICATIONS

CN 101 735 640 A Online Machine Translation, Translated on Feb. 9, 2016.*
Abbotto A. et al., "Dalton Transaction" (2011), vol. 40, pp. 12421-12438.
Abbotto, A., et al. Energy & Environmental Science (2009), vol. 2, pp. 1094-1101.
Alesi S. et al., "Green Chemistry" (2008) vol. 10, pp. 517-523.
Blankenburg L. et al., "Journal of Applied Polymer Science" (2009), vol. 111, pp. 1850-1861.
Elliott, C. M., "Nature Chemistry" (2011), vol. 3, pp. 188-189.
Grätzel M., "Nature" (2001), vol. 414, pp. 338-344.
Hagfeldt A. et al. "Chemical Reviews" (2010), vol. 110, pp. 6595-6663.

(Continued)

Primary Examiner — Golam Mowla
(74) Attorney, Agent, or Firm — Abel Law Group, LLP

(57) ABSTRACT

Organic dye for a Dye Sensitized Solar Cell (DSSC) comprising at least one electron donor group and at least two electron acceptor groups, each of said electron acceptor groups being bound to said electron donor group through a π-conjugated unit.
Said organic dye is particularly useful in a dye sensitized photoelectric transformation element, which, in its turn, can be used in a Dye Sensitized Solar Cell (DSSC).

9 Claims, No Drawings

(56) References Cited

U.S. PATENT DOCUMENTS

| | | | |
|---|---|---|---|
| 2004/0099306 A1* | 5/2004 | Hara | H01L 51/0064 136/263 |
| 2004/0187918 A1* | 9/2004 | Ikeda | H01L 51/0064 136/263 |
| 2006/0130249 A1* | 6/2006 | Ikeda | H01G 9/2031 8/550 |
| 2006/0237059 A1* | 10/2006 | Kurihara | H01G 9/2063 136/263 |
| 2007/0191455 A1* | 8/2007 | Hiyoshi | C07D 487/14 514/410 |
| 2007/0265443 A1* | 11/2007 | Wu | C07F 15/0046 544/225 |
| 2008/0015356 A1* | 1/2008 | Kakuta | C07D 231/22 546/10 |
| 2008/0067476 A1* | 3/2008 | Shigaki | C09B 23/0091 252/501.1 |
| 2008/0087327 A1* | 4/2008 | Horiuchi | C09B 23/0083 136/265 |
| 2008/0296564 A1 | 12/2008 | Nishimura et al. | |
| 2009/0044857 A1* | 2/2009 | Shigaki | C09B 23/0075 136/256 |
| 2009/0250115 A1 | 10/2009 | Miwa et al. | |
| 2011/0100467 A1* | 5/2011 | Kakita | C09B 57/10 136/263 |

OTHER PUBLICATIONS

Kalyanasundaram K., "Dye-Sensitized Solar Cells" (2010), CRC Press Inc., 1a Edition.
Yen Y.-S. et al., "Journal of Materials Chemistry" (2012), vol. 22, pp. 8734-8747.
Mishra A. et al., "Angewandte Chemie" (2009), vol. 48, pp. 2474-2499.
Yella A. et al., "Science" (2011), vol. 334, pp. 629-634.
Ning, Z. et al., "Chemical Communications" (2009), vol. 37, pp. 5483-5495.
Xu M. et al., "Journal of Phyical Chemistry C" (2009), vol. 113, pp. 2966-2973.
Zhang G. et al., "Chemical Communications" (2009), vol. 1, Issue 16, pp. 2198-2200.
Zeng W. et al., "Chemistry of Materials" (2010), vol. 22, pp. 1915-1925.
Nazeeruddin M. K., "Journal of the American Chemical Society" (1993), vol. 115, pp. 6382-6390.
Jiang, Xiao, et al. "Highly Efficient Solid—State Dye—Sensitized Solar Cells Based on Triphenylamine Dyes." Advanced Functional Materials 21.15 (2011): 2944-2952.
Shang, Huixia, et al. "The effect of anchoring group number on the performance of dye-sensitized solar cells." Dyes and Pigments 87.3 (2010): 249-256.
Zhang, Guangliang, et al. "High efficiency and stable dye-sensitized solar cells with an organic chromophore featuring a binary π-conjugated spacer." Chemical Communications 16 (2009): 2198-2200.
Still, W. C. et al. "Journal of Organic Chemistry" (1978), vol. 43, pp. 2923-2925.
Khouly M. E. et al., "The Journal of Physical Chemistry B" (2008), vol. 112, pp. 3910-3917.
Wang Z.-S. et al., "The Journal of Physical Chemistry C" (2007), vol. 111, pp. 7224-7230.
Willinger K. et al., "Journal of Materials Chemistry" (2009), vol. 19, pp. 5364-5376.
Li Z. A. et al., "Journal of Polymer Science Part A: Polymer Chemistry" (2011), vol. 49, pp. 1977-1987.
Zulauf A. et al., "European Journal of Organic Chemistry" (2008), vol. 2008, pp. 2118-2129.
Zhan H. et al., "Macromolecules" (2011), vol. 44, pp. 5155-5167.
Sahu et al., "Journal of Materials Chemistry" (2012), vol. 22, pp. 7945-7953.
Tsao H. N. et al., "ChemSusChem" (2011), vol. 4, pp. 591-594.
International Search Report and Written Opinion dated Oct. 31, 2013 for PCT/EP2013/070683.
Liu, Jingyuan, et al. "Mesoscopic titania solar cells with the tris (1, 10-phenanthroline) cobalt redox shuttle: uniped versus biped organic dyes."Energy & Environmental Science 4.8 (2011): 3021-3029.
Chang, Hui-Wen, et al. "New P-type of poly (4-methoxy-triphenylamine) s derived by coupling reactions: Synthesis, electrochromic behaviors, and hole mobility." Journal of Polymer Science Part A: Polymer Chemistry 47.16 (2009): 4037-4050.
O'Regan & Gratzel. "A low-cost, high-efficiency solar cell based on dye-sensitized colloidal TiO2 films." Institute of Physical Chemistry, Swiss Federal Institute of Technology, Letters to Nature, vol. 353 (1991), p. 737-740.

* cited by examiner

ORGANIC DYE FOR A DYE-SENSITIZED SOLAR CELL

The present invention relates to an organic dye for a Dye Sensitized Solar Cell (DSSC).

More specifically, the present invention relates to an organic dye for a Dye Sensitized Solar Cell (DSSC) comprising at least one electron donor group and at least two electron acceptor groups, each of said electron acceptor groups being bound to said electron donor group through a π-conjugated unit.

Said organic dye is particularly useful in a dye sensitized photoelectric transformation element, which, in its turn, can be used in a Dye Sensitized Solar Cell (DSSC).

Consequently, a further object of the present invention relates to a dye sensitized photoelectric transformation element comprising at least one organic dye indicated above, in addition to a Dye Sensitized Solar Cell (DSSC) comprising said photoelectric transformation element.

Dye Sensitized Solar Cells (DSSCs) were developed by Grätzel M. et al. in 1991 and they have attracted considerable attention in recent years as they represent one of the photovoltaic conversion methods of solar light having a greater potentiality both in terms of photoelectric transformation efficiency ($\eta$) and in terms of production costs.

Further details relating to Dye Sensitized Solar Cells (DSSCs) can be found, for example, in: Kalyanasundaram K., "*Dye-Sensitized Solar Cells*" (2010), CRC Press Inc., 1$^a$ Edition; Elliott, C. M., "*Nature Chemistry*" (2011), Vol. 3, pages 188-189; Hagfeldt A. et al. "*Chemical Reviews*" (2010), Vol. 110, pages 6595-6663; Grätzel M., "*Nature*" (2001), Vol. 414, pages 338-344.

Dye Sensitized Solar Cells (DSSCs) generally comprise four main components: an optically transparent electrode (anode); an organic or organometallic molecule, called dye or photosensitizer (hereinafter indicated as dye), adsorbed on a semiconductor oxide, typically on mesoporous nanocrystalline titanium dioxide ($TiO_2$); a liquid inorganic electrolyte or a solid organic hole transporting material; and a counter-electrode (cathode). The dye is photochemically excited when it absorbs solar light and in this way, its electrons move to an orbital with a higher energy (LUMO or dye excited state) from which they are transferred to the conduction band of the semi-conductor oxide [i.e. titanium dioxide ($TiO_2$], leaving the dye molecules in their oxidized form. The electrons are then collected on a transparent conductive layer, generally consisting of tin dioxide ($SnO_2$) doped with fluorine ("Fluorine-doped Tin Oxide"—FTO) and reach the counter-electrode (cathode) through an external electric circuit. The oxidized molecules of the dye are regenerated as follows: through a transfer catalyzed by platinum (Pt), deposited on the cathode, the electrons trigger a series of redox reactions through a redox pair which acts as an electrolyte (typically the pair iodide/triiodide), at the end of said reactions, the redox pair in reduced form transfers an electron to the dye, which had remained in oxidized form, regenerating it and closing the cycle.

The dye represents one of the main components of Dye Sensitized Solar Cells (DSSCs) as its function is to collect solar light and to transform it into a stream of electrons. In order to have solar cells with high photoelectric transformation efficiencies ($\eta$), the dye must have optimum optical absorption properties, i.e. a wide absorption spectrum of solar light and a high molar extinction coefficient ($\epsilon$).

The most widely-used organic dyes, which have allowed high photoelectric transformation efficiencies ($\eta$) to be reached (i.e. photoelectric transformation efficiencies ($\eta$) of over 11%), are organometallic compounds typically based on ruthenium complexes in oxidation state 2+ [Ru(II)]. In spite of recent progress (see, for example, Abbotto A. et al., "*Dalton Transaction*" (2011), Vol. 40, pages 12421-12438), these compounds, however, have some drawbacks such as, for example, a low molar extinction coefficient ($\epsilon$) inherent to derivatives of [Ru(II)]; difficulties in synthesis and purification (they require, in fact, an accurate synthesis and complex purification phases); high costs for both the synthesis and the ruthenium itself; a limited chemical stability.

For these reasons, metal-free organic dyes have recently been proposed, as described for example, in Yen Y.-S. et al., "*Journal of Materials Chemistry*" (2012), Vol. 22, pages 8734-8747; Mishra A. et al., in "*Angewandte Chemie*" (2009), Vol. 48, pages 2474-2499. These metal-free organic dyes have various advantages with respect to organometallic dyes, among which: a higher structural variety, a simpler and less expensive synthesis (for example, the purification can be carried out using standard methods adopted in organic chemistry), presence of a chemical industry already capable of carrying out the synthesis on a large scale and, above all, good optical absorption properties, i.e. the possibility of obtaining, through a suitable design, wide absorption spectra of solar light and high molar extension coefficients ($\epsilon$). With the exception of only one example in which a metal-free organic dye, mixed with a metal-porphyrin (i.e. a zinc porphyrin) has allowed, in the presence of electrolytes suitably designed and with questionable applicability [e.g., a redox electrolyte based on Co$^{(II/III)}$tris(bipyridyl)], a photoelectric transformation efficiency ($\eta$) of 12.3% to be obtained [as indicated by Yella A. et al., "*Science*" (2011), Vol. 334, pages 629-634], metal-free organic dyes have allowed Dye Sensitized Solar Cells (DSSCs) to be obtained, having photoelectric transformation ($\eta$) efficiencies lower than those obtained using organic dyes containing metals.

Further studies have in fact been carried out in order to find metal-free organic dyes showing improved optical absorption properties.

The structure of metal-free organic dyes is usually of the linear type D-π-A, wherein D is an electron donor group (i.e. electron-rich), π is an unsaturated spacer having π-conjugated bonds and A is an electron acceptor group (i.e. electron-poor) to which a group is bound which allows the anchoring (i.e. adsorption) of the dyes based on titanium dioxide (typically, a COOH group).

Metal-free organic dyes capable of giving dye sensitized solar cells (DSSCs) with a good photoelectric transformation efficiency ($\eta$) in which the electron donor group (D) has a triarylamine core and π is an unsaturated spacer comprising thiophene structures such as, for example, condensed monocyclic and polycyclic thiophene rings, are described, for example, by Ning, Z. et al., in "*Chemical Communications*" (2009), Vol. 37, pages 5483-5495. Organic dyes of the same type are also described, for example by: Xu M. et al., in "*Journal of Physical Chemistry C*" (2009), Vol. 113, pages. 2966-2973; Zhang G. et al., in "*Chemical Communications*" (2009), Vol. 1, Issue 16, pages 2198-2200; Zeng W. et al., in "*Chemistry of Materials*" (2010), Vol. 22, pages 1915-1925.

In "*Energy & Environmental Science*" (2009), Vol. 2, pages 1094-1101, Abbotto A. et al. describe metal-free organic dyes for dye sensitized solar cells (DSSCs) with a multi-branched structure, comprising an electron donor D chemically bound to two branches of the π-A type, wherein π is an unsaturated spacer with π-conjugated bonds and A is an electron acceptor group, each group A carrying the carboxylic function necessary for anchorage on the titanium dioxide. In other words, there is a shift from a geometry of the linear type (i.e. D-π-A) to a geometry of the branched type.

This branched-type geometry on the one hand allows a more extended π-conjugated system, and consequently a more efficient absorption of the solar spectrum, and on the other hand, to contain, by means of the two groups A, two channels (instead of only one channel, typical of the other organic dyes) for transferring the electrons from the excited state of the dye to the conduction band of the titanium dioxide (similar to organometallic dyes having from 2 to 4 groups A). The above organic dyes show an improvement not only in the optical absorption properties, but also in the chemical stability, with respect to the corresponding linear structures. With respect to the photoelectric transformation efficiency (η), however, the above organic dyes do not always show good results.

In spite of the numerous efforts made, the study of new metal-free organic dyes capable of giving dye sensitized solar cells (DSSCs) having a good photoelectric transformation efficiency (η), i.e. a photoelectric transformation efficiency (η) higher than or equal to 5%, is still of great interest.

The Applicant has therefore considered the problem of finding an organic dye capable of giving dye sensitized solar cells (DSSCs) having a good photoelectric transformation efficiency (η), i.e. a photoelectric transformation efficiency (η) higher than or equal to 5%.

The Applicant has now found an organic dye comprising at least one electron donor group and at least two electron acceptor groups, each of said electron acceptor groups being bound to said electron donor group through a π-conjugated unit which is capable of providing a Dye Sensitized Solar Cell (DSSC) having a good photoelectric transformation efficiency (η), i.e. a photoelectric transformation efficiency (η) higher than or equal to 5% and with open-circuit photovoltage (Voc), short-circuit current density (Jsc) and fill factor FF values comparable to those of organometallic dyes known in the art.

An object of the present invention therefore relates to an organic dye having general formula (I):

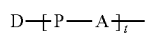  (I)

wherein:
P represents one of the following general formulae (Ia), (Ib), (Ic), (Id):

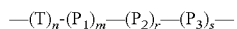  (Ia)

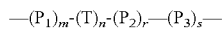  (Ib)

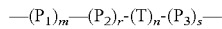  (Ic)

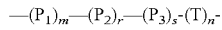  (Id)

wherein:
T represents a carbon-carbon triple bond having general formula (II), or a carbon-carbon double bond having general formula (III) or (IV):

wherein $R_1$ and $R_2$, the same or different, represent a hydrogen atom; or they are selected from linear or branched $C_1$-$C_{20}$, preferably $C_1$-$C_{12}$ alkyl groups, saturated or unsaturated, optionally containing heteroatoms, aryl groups optionally substituted, heteroaryl groups optionally substituted, cycloalkyl groups optionally substituted;

n is an integer ranging from 0 to 5, preferably is 0 or 1;

$P_1$, $P_2$ and $P_3$, the same or different, are selected from bivalent heteroaryl groups having the following general formulae (V), (VI), (VII), (VIII), (IX), (X), (XI), (XII):

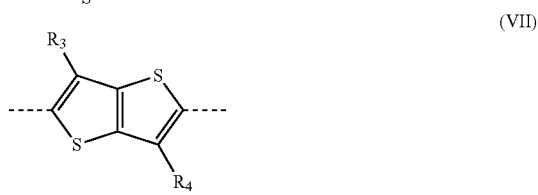

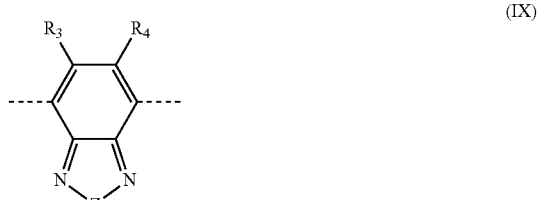

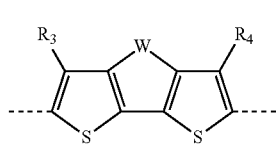

-continued

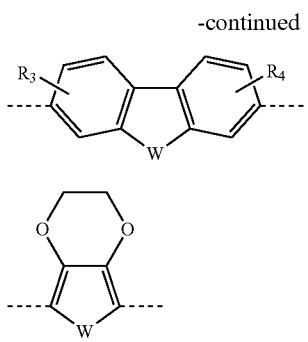

wherein:
$R_3$ and $R_4$, the same or different, represent a hydrogen atom; or they represent a halogen atom such as, for example, fluorine, chlorine or bromine, preferably fluorine or bromine; or they are selected from linear or branched $C_1$-$C_{20}$, preferably $C_1$-$C_{12}$, alkyl groups, saturated or unsaturated, optionally containing heteroatoms, aryl groups optionally substituted, heteroaryl groups optionally substituted, cycloalkyl groups optionally substituted, heterocyclic groups optionally substituted, trialkyl- or triaryl-silyl groups, dialkyl- or diaryl-amine groups, dialkyl- or diaryl phosphinic groups, linear or branched $C_1$-$C_{20}$, preferably $C_2$-$C_{10}$, alkoxyl groups, saturated or unsaturated, aryloxyl groups optionally substituted, thioalkoxyl or thioaryloxyl groups optionally substituted, cyano groups;

Z represents a heteroatom such as, for example, oxygen, sulfur, selenium, tellurium, preferably sulfur; or it is selected from groups having general formula $X(R_5)$ or from groups having general formula $Y(R_6R_7)$, wherein $R_5$, $R_6$ and $R_7$, have the meanings specified hereunder, X represents a heteroatom such as, for example, nitrogen, phosphorous, arsenic, boron, preferably nitrogen, Y represents a carbon, silicon or germanium atom, preferably silicon or carbon;

W represents a heteroatom such as, for example, oxygen, sulfur, selenium, tellurium, preferably sulfur; or it is selected from groups having general formula $Y(R_6R_7)$ wherein $R_6$ and $R_7$, have the meanings specified hereunder, Y represents a carbon, silicon, or germanium atom, preferably silicon or carbon;

$R_5$ represents a hydrogen atom; or it is selected from linear or branched $C_1$-$C_{20}$, preferably $C_1$-$C_{12}$ alkyl groups, saturated or unsaturated, optionally containing heteroatoms, aryl groups optionally substituted, cycloalkyl groups optionally substituted;

$R_6$ and $R_7$, the same or different, are selected from linear or branched $C_1$-$C_{20}$, preferably $C_1$-$C_{12}$ alkyl groups, saturated or unsaturated, optionally containing heteroatoms, aryl groups optionally substituted, cycloalkyl groups optionally substituted, linear or branched $C_1$-$C_{20}$, preferably $C_1$-$C_{10}$ alkoxyl groups, saturated or unsaturated, aryloxyl groups optionally substituted, thioalkoxyl or thioaryloxyl groups optionally substituted;

or $R_3$ and $R_4$, in general formulae (V), (VIII), or (IX), can be optionally bound to each other so as to form, together with the other atoms to which they are bound, a cycle containing from 1 to 12 carbon atoms, saturated, unsaturated, or aromatic, optionally substituted with linear or branched $C_1$-$C_{20}$ alkyl groups, saturated or unsaturated, optionally containing heteroatoms, aryl groups optionally substituted, heteroaryl groups optionally substituted, cycloalkyl groups optionally substituted, heterocyclic groups optionally substituted, trialkyl- or triaryl-silyl groups, dialkyl- or diaryl-amine groups, dialkyl- or diaryl phosphinic groups, linear or branched $C_1$-$C_{20}$, preferably $C_2$-$C_{10}$, alkoxyl groups, saturated or unsaturated, aryloxyl groups optionally substituted, thioalkoxyl or thioaryloxyl groups optionally substituted, cyano groups, said cycle optionally containing heteroatoms such as, for example, oxygen, sulfur, nitrogen, silicon, phosphorous, selenium;

m, r and s, the same or different, are an integer ranging from 0 to 5, preferably are 0 or 1, with the proviso that at least one of m, r and s, is different from 0;

A represents a —COOH group; a phosphonic group having formula —PO(OH)$_2$ or —PO(OH)(R), wherein R is selected from linear or branched $C_1$-$C_{20}$, preferably $C_1$-$C_{10}$, alkyl groups; a carboxycyano-vinylene group having general formula (XIII) or (XIV):

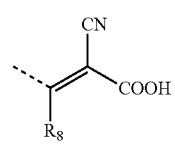

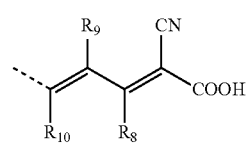

wherein $R_8$, $R_9$ and $R_{10}$, the same or different, represent a hydrogen atom; or they represent a halogen atom such as, for example, fluorine, chlorine or bromine, preferably fluorine or bromine; or they are selected from linear or branched $C_1$-$C_{20}$, preferably $C_1$-$C_{12}$, alkyl groups, saturated or unsaturated, optionally containing heteroatoms, aryl groups optionally substituted, heteroaryl groups optionally substituted, cycloalkyl groups optionally substituted, cyano groups, nitro groups;

t is an integer ranging from 2 to 6, preferably is 2 or 3;

D represents a triarylamine group having the following general formulae (XV), (XVI), (XVII), (XVIII), (XIX), (XX), (XXI), (XXII), (XXIII), (XXIV):

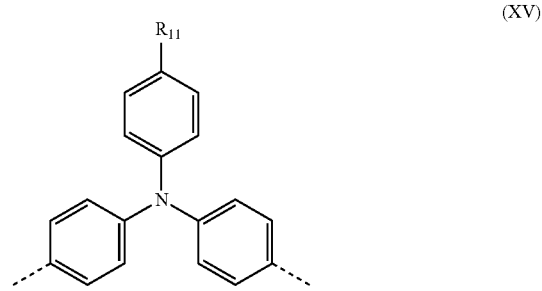

-continued
(XVI)
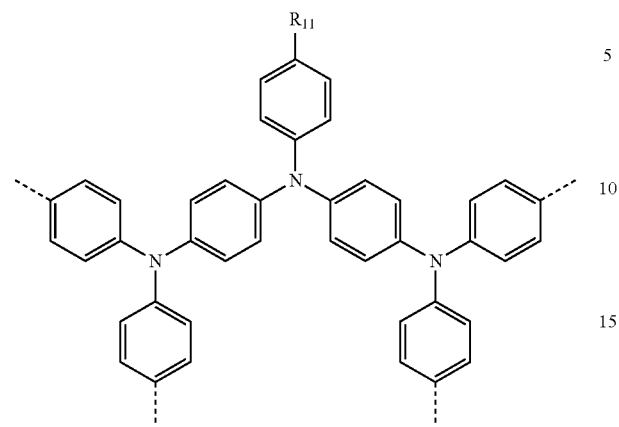
(XVII)
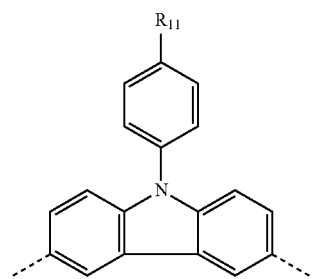
(XVIII)
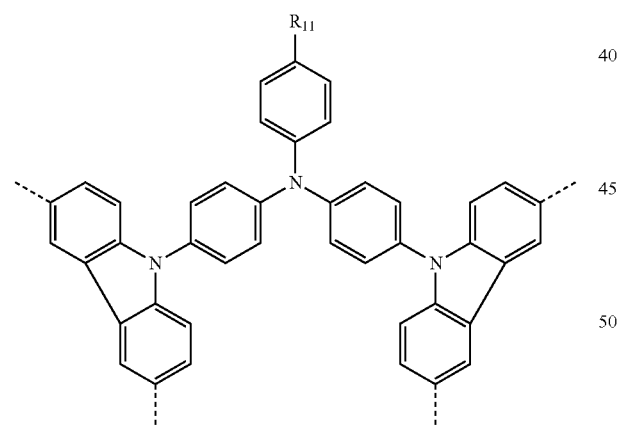
(XIX)
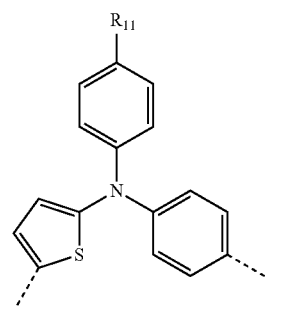
(XX)
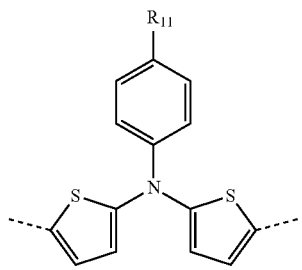
(XXI)
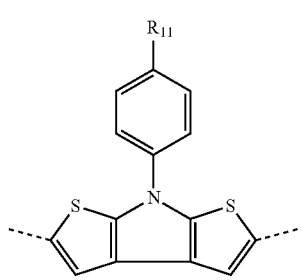
(XXII)
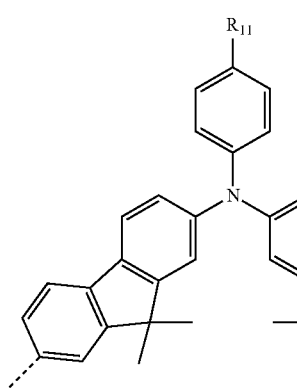
(XXIII)
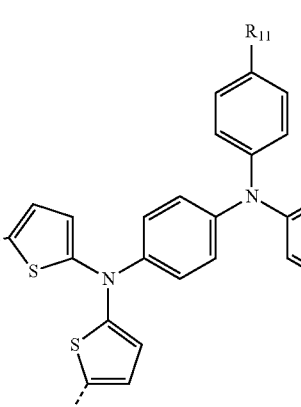
(XXIV)
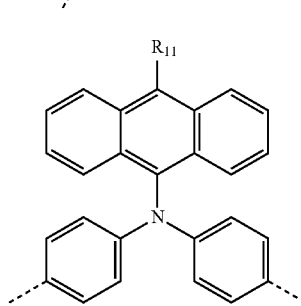

wherein $R_{11}$ represents a hydrogen atom, or it is selected from linear or branched $C_1$-$C_{20}$, preferably $C_1$-$C_{12}$, alkyl groups, saturated or unsaturated, optionally containing heteroatoms, linear or branched $C_1$-$C_{20}$, preferably $C_1$-$C_{10}$, alkoxyl groups, saturated or unsaturated, polyethyleneoxyl groups having formula R'—O—[—CH$_2$—CH$_2$—O]$_m$— wherein R' represents a hydrogen atom; or it is selected from linear or branched $C_1$-$C_{20}$, preferably $C_1$-$C_{12}$, alkyl groups, and m is an integer ranging from 1 to 20, preferably ranging from 2 to 10, aryl groups optionally substituted, heteroaryl groups optionally substituted, cycloalkyl groups optionally substituted, heterocyclic groups optionally substituted, trialkyl- or triaryl-silyl groups, dialkyl- or diaryl-amine groups, dialkyl- or diaryl phosphinic groups, linear or branched $C_1$-$C_{20}$, preferably $C_2$-$C_{10}$, alkoxyl groups, saturated or unsaturated, aryloxyl groups optionally substituted, thioalkoxyl or thioaryloxyl groups optionally substituted.

For the purposes of the present description and of the following claims, the definition of the numerical ranges always include the extremes unless otherwise specified.

For the purposes of the present description and of the following claims, the term "comprising" also includes the wording "which essentially consists of" or "which consists of".

The term "$C_1$-$C_{20}$ alkyl groups" means alkyl groups having from 1 to 20 carbon atoms, linear or branched, saturated or unsaturated. Specific examples of $C_1$-$C_{20}$ alkyl groups are: methyl, ethyl, n-propyl, iso-propyl, n-butyl, iso-butyl, t-butyl, pentyl, hexyl, heptyl, octyl, 2-ethylheptyl, 2-ethylhexyl, 2-butenyl, 2-pentenyl, 2-ethyl-3-hexenyl, 3-octenyl, 1-methyl-4-hexenyl, 2-butyl-3-hexenyl.

The term "$C_1$-$C_{20}$ alkyl groups, optionally containing heteroatoms" means alkyl groups having from 1 to 20 carbon atoms, linear or branched, saturated or unsaturated, wherein at least one hydrogen atom is substituted by a heteroatom selected from: halogens such as, for example, fluorine, chlorine, bromine, preferably fluorine; nitrogen; sulfur; oxygen. Specific examples of $C_1$-$C_{20}$ alkyl groups optionally containing heteroatoms are: fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl, perfluoropentyl, perfluorooctyl, perfluorodecyl, oxymethyl, thiomethyl, thyoethyl, dimethylamino, propylamino, dioctylamino.

The term "aryl groups" means aromatic carbocyclic groups containing from 6 to 60 carbon atoms. Said aryl groups can be optionally substituted with one or more groups, the same or different, selected from: halogen atoms such as, for example, fluorine, chlorine, bromine, preferably fluorine; hydroxyl groups; $C_1$-$C_{12}$ alkyl groups; $C_1$-$C_{12}$ alkoxyl groups; $C_1$-$C_{12}$ thioalkoxyl groups; $C_3$-$C_{24}$ tri-alkylsilyl groups; pentaethyleneoxyl groups; cyano groups; amino groups; $C_1$-$C_{12}$ mono- or di-alkylamine groups; nitro groups. Specific examples of aryl groups are: phenyl, methyphenyl, trimethylphenyl, methoxyphenyl, hydroxyphenyl, phenyloxyphenyl, fluorophenyl, pentafluorophenyl, chlorophenyl, bromophenyl, nitrophenyl, dimethylaminophenyl, naphthyl, phenylnaphthyl, phenanthrene, anthracene.

The term "heteroaryl groups" means penta- or hexaatomic aromatic heterocyclic groups, also benzocondensed or heterobicyclic, containing from 4 to 60 carbon atoms and from 1 to 4 heteroatoms selected from nitrogen, sulfur, silicon, selenium, phosphorous. Said heteroaryl groups can be optionally substituted with one or more groups, the same or different, selected from: halogen atoms such as, for example fluorine, chlorine, bromine, preferably fluorine; hydroxyl groups; $C_1$-$C_{12}$ alkyl groups; $C_1$-$C_{12}$ alkoxyl groups; $C_1$-$C_{12}$ thioalkoxyl groups; $C_3$-$C_{24}$ tri-alkylsilyl groups; polyethyleneoxyl groups; cyano groups; amino groups; $C_1$-$C_{12}$ mono- or di-alkylamine groups; nitro groups. Specific examples of heteroaryl groups are: pyridine, methylpyridine, methoxypyridine, phenylpyridine, fluoropyridine, pyrimidine, pyridazine, pyrazine, triazine, tetrazine, quinoline, quinoxaline, quinazoline, furan, thiophene, hexylthiophene, bromothiophene, dibromothiophene, pyrrole, oxazole, thiazole, isooxazole, isothiazole, oxadiazole, thiadiazole, pyrazole, imidazole, triazole, tetrazole, indole, benzofuran, benzothiophene, benzoxazole, benzothiazole, benzooxadiazole, benzothiadiazole, benzopyrazole, benzimidazole, benzotriazole, triazolepyridine, triazolepyrimidine, coumarin.

The term "cycloalkyl groups" means cycloalkyl groups having from 3 to 30 carbon atoms. Said cycloalkyl groups can be optionally substituted with one or more groups, the same or different, selected from: halogen atoms such as, for example, fluorine, chlorine, bromine, preferably fluorine; hydroxyl groups; $C_1$-$C_{12}$ alkyl groups; $C_1$-$C_{12}$ alkoxyl groups; $C_1$-$C_{12}$ thioalkoxyl groups; $C_3$-$C_{24}$ tri-alkylsilyl groups; polyethyleneoxyl groups; cyano groups; amino groups; $C_1$-$C_{12}$ mono- or di-alkylamine groups; nitro groups. Specific examples of cycloalkyl groups are: cyclopropyl, 2,2-difluorocyclopropyl, cyclobutyl, cyclopentyl, cyclohexyl, methylcyclohexyl, methoxycyclohexyl, fluorocyclohexyl, phenylcyclohexyl, decalin, abietyl.

The term "heterocyclic groups" means rings having from 3 to 12 atoms, saturated or unsaturated, containing at least one heteroatom selected from nitrogen, oxygen, sulfur, silicon, selenium, phosphorous, optionally condensed with other aromatic or non-aromatic rings. Said heterocyclic groups can be optionally substituted with one or more groups, the same or different, selected from: halogen atoms, such as, for example, fluorine, chlorine, bromine, preferably fluorine; hydroxyl groups; $C_1$-$C_{12}$ alkyl groups; $C_1$-$C_{12}$ alkoxyl groups; $C_1$-$C_{12}$ thioalkoxyl groups; $C_3$-$C_{24}$ tri-alkylsilyl groups; polyethyleneoxyl groups; cyano groups; amino groups; mono- or di-alkylamine $C_1$-$C_{12}$ groups; nitro groups. Specific examples of heterocyclic groups are: pyrrolidine, methoxypyrrolidine, piperidine, fluoropiperidine, methylpiperidine, dihydropyridine, piperazine, morpholine, thiazine, indoline, phenylindoline, 2-ketoazetidine, diketopiperazine, tetrahydrofuran, tetrahydrothiophene.

The term "cycle" means a system containing a ring containing from 1 to 12 carbon atoms, optionally containing heteroatoms selected from nitrogen, oxygen, sulfur, silicon, selenium, phosphorous. Specific examples of cycle are: toluene, benzonitrile, cycloheptatriene, cyclooctadiene, pyridine, piperidine, tetrahydrofuran, thiadiazole, pyrrole, thiophene, selenophene, t-butylpyridine.

The term "trialkyl- or triaryl-silyl groups" means groups comprising one silicon atom to which three alkyl groups $C_1$-$C_{12}$, or three aryl groups $C_6$-$C_{24}$, are bound, or a combination of the two. Specific examples of trialkyl- or triarylsilyl groups are: trimethylsilane, triethylsilane, trihexylsilane, tridodecylsilane, dimethyldodecylsilane, triphenylsilane, methyldiphenyl-silane, dimethylnaphthylsilane.

The term "dialkyl- or diaryl-amine groups" means groups comprising a nitrogen atom to which two $C_1$-$C_{12}$ alkyl groups, or two $C_6$-$C_{24}$ aryl groups, are bound, or a combination of thereof. Specific example of dialkyl- or diarylamine groups are: dimethylamine, diethylamine, dibutylamine, diisobutylamine, diphenylamine, methylphenylamine, dibenzylamine, ditolylamine, dinaphthylamine.

The term "dialkyl- or diaryl-phosphine groups" means groups comprising one phosphorous atom to which two $C_1$-$C_{12}$ alkyl groups, or two $C_6$-$C_{24}$ aryl groups, are bound, or a combination thereof. Specific examples of dialkyl- or diaryl-phosphine groups are: dimethylphosphine, diethylphosphine, dibutylphosphine, diphenylphosphine, methylphenylphosphine, dinaphthyl-phosphine.

The term "$C_1$-$C_{20}$ alkoxyl groups" means groups comprising an oxygen atom to which a linear or branched $C_1$-$C_{20}$ alkyl group is bound. Specific examples of $C_1$-$C_{20}$ alkoxyl groups are: methoxyl, ethoxyl, n-propoxyl, iso-propoxyl, n-butoxyl, iso-butoxyl, t-butoxyl, pentoxyl, hexyloxyl, heptyloxyl, octyloxyl, nonyloxyl, decyloxyl, dodecyloxyl.

The term "aryloxyl groups" means groups comprising one oxygen atom to which one $C_6$-$C_{24}$ aryl group is bound. Said aryloxyl groups can be optionally substituted with one or more groups, the same or different, selected from: halogen atoms such as, for example, fluorine, chlorine, bromine, preferably fluorine; hydroxyl groups; $C_1$-$C_{12}$ alkyl groups; $C_1$-$C_{12}$ alkoxyl groups; $C_1$-$C_{12}$ thioalkoxyl groups; $C_3$-$C_{24}$ trialkylsilyl groups; cyano groups; amino groups; $C_1$-$C_{12}$ mono- or di-alkylamine groups; nitro groups. Specific examples of aryloxyl groups are: phenoxyl, para-methylphenoxyl, para-fluorophenoxyl, ortho-butylphenoxyl, naphthyloxyl, anthracenoxyl.

The term "thioalkoxyl or thioaryloxyl groups" means groups comprising one sulfur atom to which a $C_1$-$C_{12}$ alkoxyl group, or a $C_6$-$C_{24}$ aryloxyl group, is bound. Said thioalkoxyl or thioaryloxyl groups can be optionally substituted with one or more groups, the same or different, selected from: halogen atoms such as, for example, fluorine, chlorine, bromine, preferably fluorine; hydroxyl groups; $C_1$-$C_{12}$ alkyl groups; $C_1$-$C_{12}$ alkoxyl groups; $C_1$-$C_{12}$ thioalkoxyl groups; $C_3$-$C_{24}$ trialkylsilyl groups; cyano groups; amino groups; $C_1$-$C_{12}$ mono- or di-alkylamino groups; nitro groups. Specific examples of thioalkoxyl or thioaryloxyl groups are: thiomethoxyl, thioethoxyl, thiopropoxyl, thiobutoxyl, thioisobutoxyl, 2-ethylthiohexyloxyl, thiophenoxyl, para-fluorothiophenoxyl, ortho-butylthiophenoxyl, naphthylthioxyl, anthracenylthioxyl.

The term "polyethyleneoxyl groups" means groups having from 2 to 80 carbon atoms containing at least one oxyethylene unit. Specific examples of polyethyleneoxyl groups are: methyloxy-ethyleneoxyl, methyloxy-diethyleneoxyl, 3-oxatetraoxyl, 3,6-dioxaheptyloxyl, 3,6,9-trioxadecyloxyl, 3,6,9,12-tetraoxahexadecyloxyl.

According to a preferred embodiment of the present invention, in said general formula (I):

P represents general formula (Ia) wherein:
T represents a carbon-carbon triple bond having general formula (II), or a carbon-carbon double bond having general formula (III) or (IV):

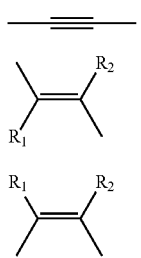

(II)

(III)

(IV)

wherein $R_1$ and $R_2$, the same as each other, represent a hydrogen atom;
n is 0 or 1;
$P_1$, $P_2$ and $P_3$, the same or different, are selected from heteroaryl bivalent groups having the following general formulae (V), (VII), (XII):

(V)

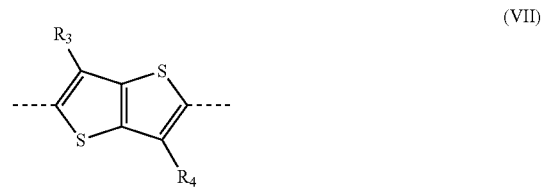

(VII)

(XII)

wherein:
$R_3$ and $R_4$, the same as each other, represent a hydrogen atom;
W represents sulfur;
m, r and s, the same or different, represent 0 or 1, with the proviso that at least one is different from 0;
A represents a carboxycyanovinylene group having general formula (XIII):

(XIII)

wherein $R_8$ represents a hydrogen atom;
t is 2;
D represents a triarylamine group having general formula (XV):

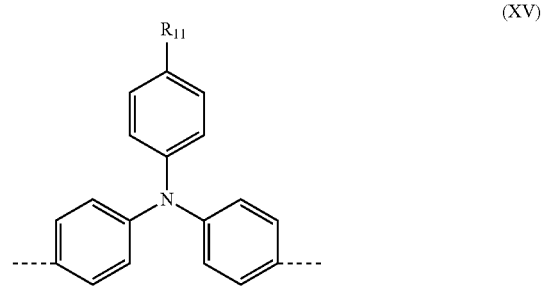

(XV)

wherein $R_{11}$ represents a hydrogen atom, or it is selected from $C_1$-$C_{20}$ alkoxyl groups, preferably is a methoxyl, hexyloxyl, octyloxyl group; or it is selected from polyethyleneoxyl groups having formula R'—O—[—CH$_2$—CH$_2$—O]$_m$— wherein R' represents a hydrogen atom or it is selected from linear or branched C$_1$-C$_{20}$ alkyl groups, and m is an integer ranging from 1 to 20; preferably R' is methyl and m is 3; or R$_{11}$ is an aryl group optionally substituted with one or more groups, the same or different, selected from: C$_1$-C$_{16}$ alkyl groups, C$_1$-C$_{16}$ alkoxyl groups, C$_1$-C$_{16}$ thioalkoxyl groups, C$_3$-C$_{24}$ trialkylsilyl groups, polyethyleneoxyl groups, amino groups, C$_1$-C$_{16}$ mono- or di-alkylamine groups, R$_{11}$ is preferably 2,4-di-hexyloxybenzene; or R$_{11}$ is a heteroaryl group containing from 1 to 4, preferably 1 or 2, heteroatoms selected from nitrogen, oxygen, sulfur, silicon, selenium, phosphorous, preferably sulfur, optionally substituted with one or more groups, the same or different, selected from C$_1$-C$_{16}$ alkyl groups; C$_1$-C$_{16}$ alkoxyl groups; C$_1$-C$_{16}$ thioalkoxyl groups; C$_3$-C$_{24}$ trialkylsilyl groups, polyethyleneoxyl groups, amino groups, C$_1$-C$_{16}$ mono- or di-alkylamine groups, R$_{11}$ is preferably 2-(5-hexyl)-thiophene or 5-(5'-hexyl)-2,2'-dithiophene.

Specific examples of compounds having general formula (I) are indicated in Table 1.

TABLE 1

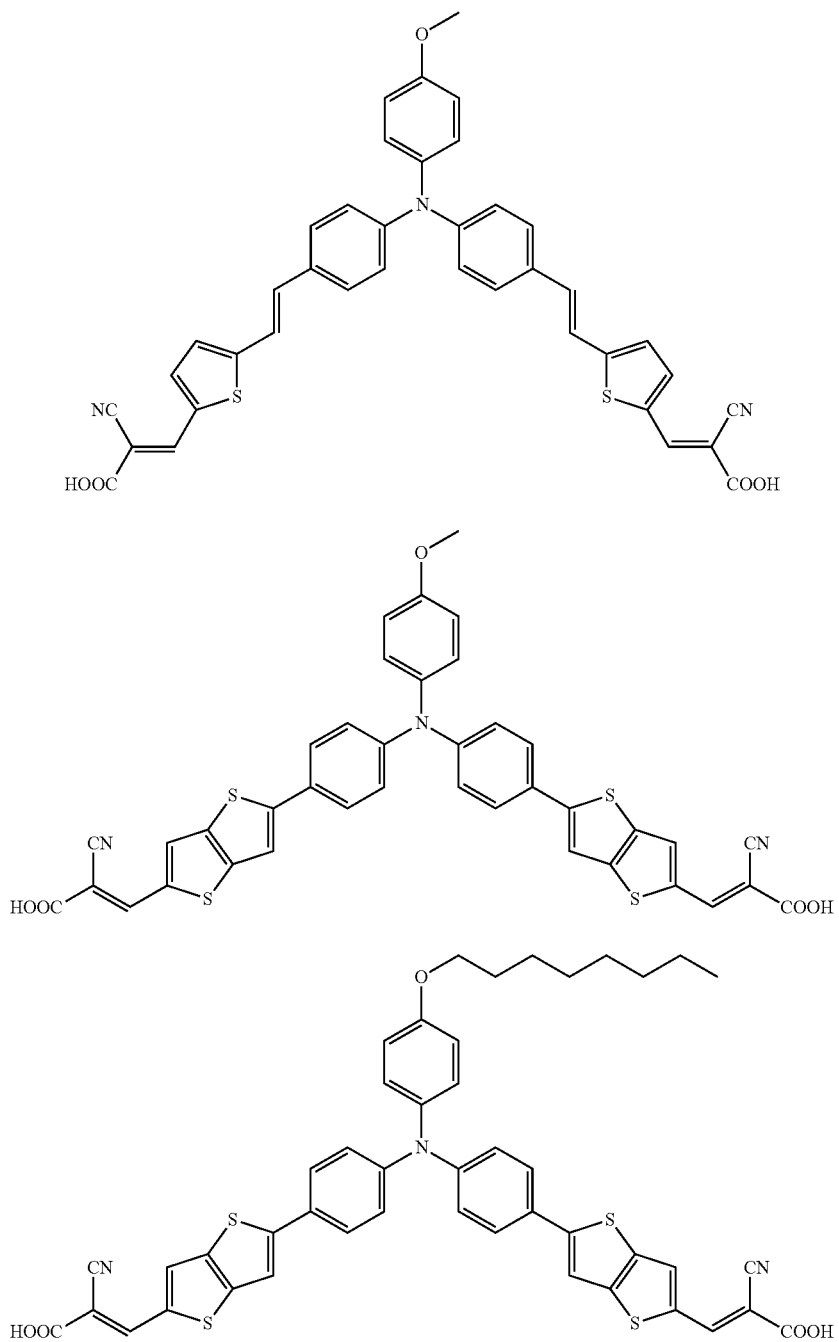

TABLE 1-continued
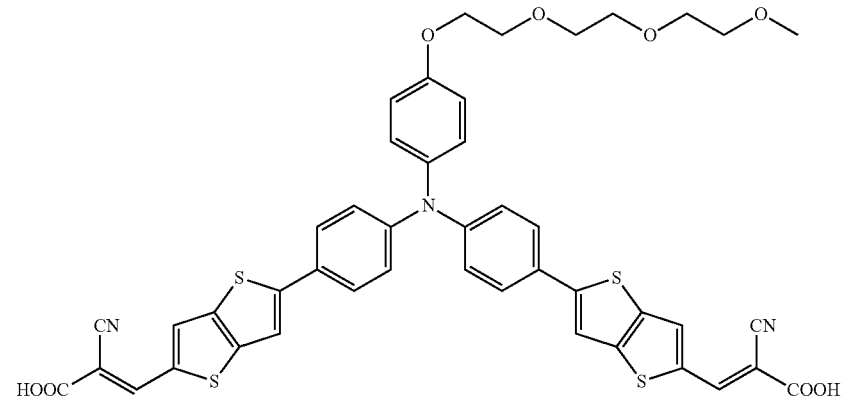 [SMILES: COCCOCCOCCOc1ccc(N(c2ccc(-c3cc4sc(/C=C(\C#N)C(=O)O)cc4s3)cc2)c2ccc(-c3cc4sc(/C=C(\C#N)C(=O)O)cc4s3)cc2)cc1]
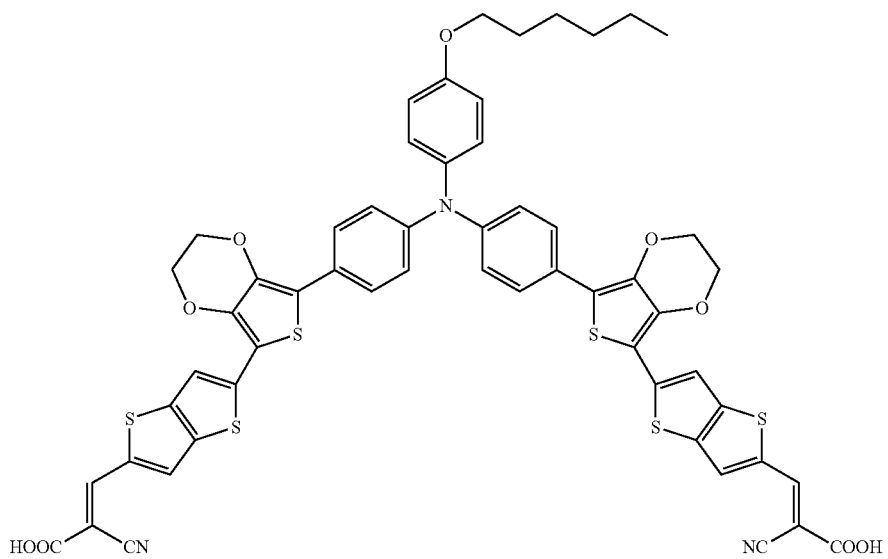 [SMILES: CCCCCCOc1ccc(N(c2ccc(-c3sc(-c4cc5sc(/C=C(\C#N)C(=O)O)cc5s4)c4c3OCCO4)cc2)c2ccc(-c3sc(-c4cc5sc(/C=C(\C#N)C(=O)O)cc5s4)c4c3OCCO4)cc2)cc1]
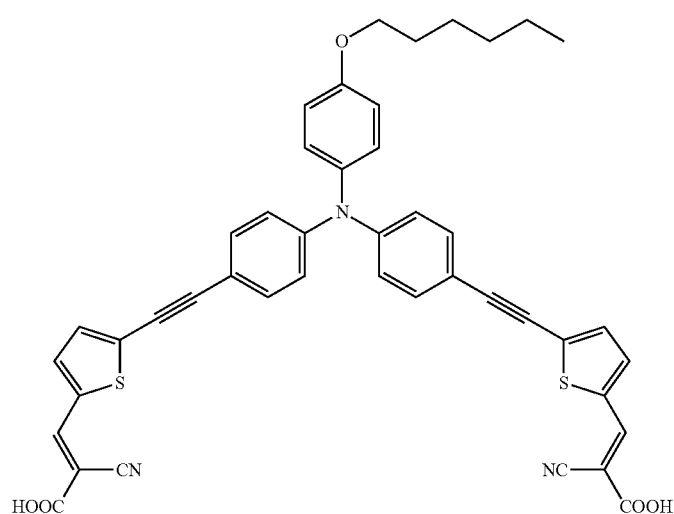 [SMILES: CCCCCCOc1ccc(N(c2ccc(C#Cc3ccc(/C=C(\C#N)C(=O)O)s3)cc2)c2ccc(C#Cc3ccc(/C=C(\C#N)C(=O)O)s3)cc2)cc1]

TABLE 1-continued
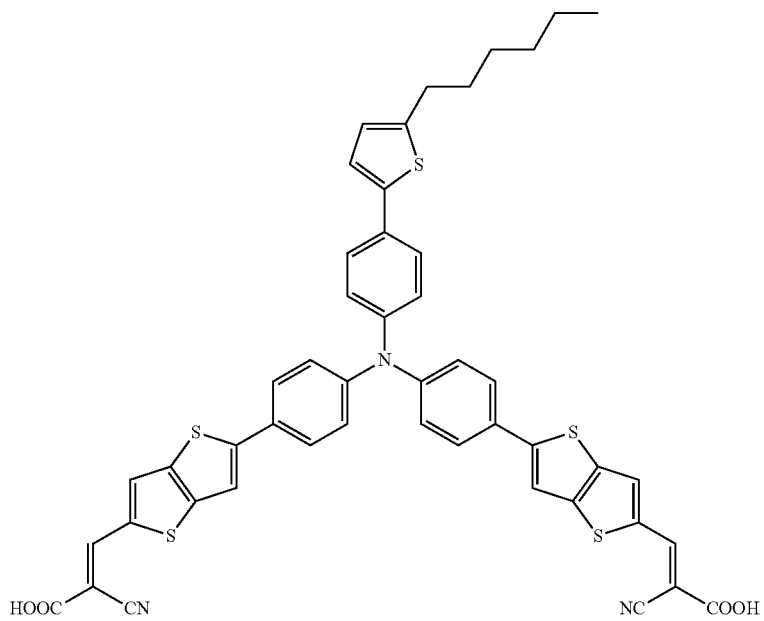 [SMILES: CCCCCCc1ccc(-c2ccc(N(c3ccc(-c4cc5sc(/C=C(\C#N)C(=O)O)cc5s4)cc3)c3ccc(-c4cc5sc(/C=C(\C#N)C(=O)O)cc5s4)cc3)cc2)s1]
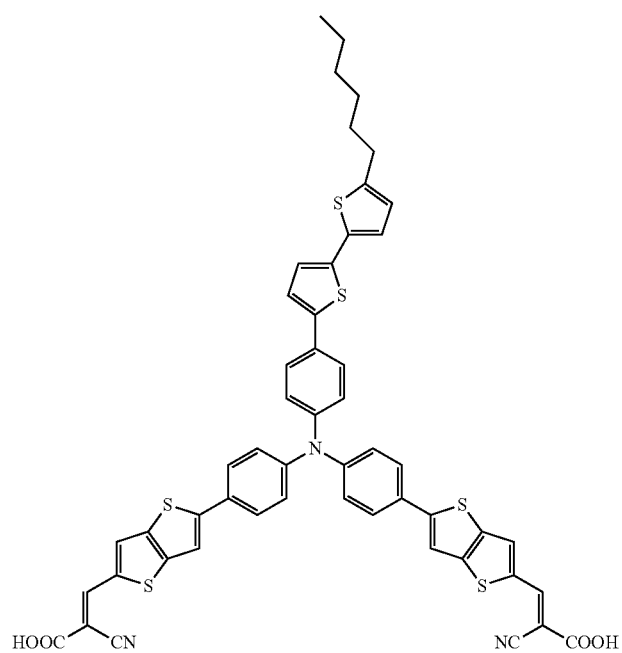 [SMILES: CCCCCCc1ccc(-c2ccc(-c3ccc(N(c4ccc(-c5cc6sc(/C=C(\C#N)C(=O)O)cc6s5)cc4)c4ccc(-c5cc6sc(/C=C(\C#N)C(=O)O)cc6s5)cc4)cc3)s2)s1]

TABLE 1-continued
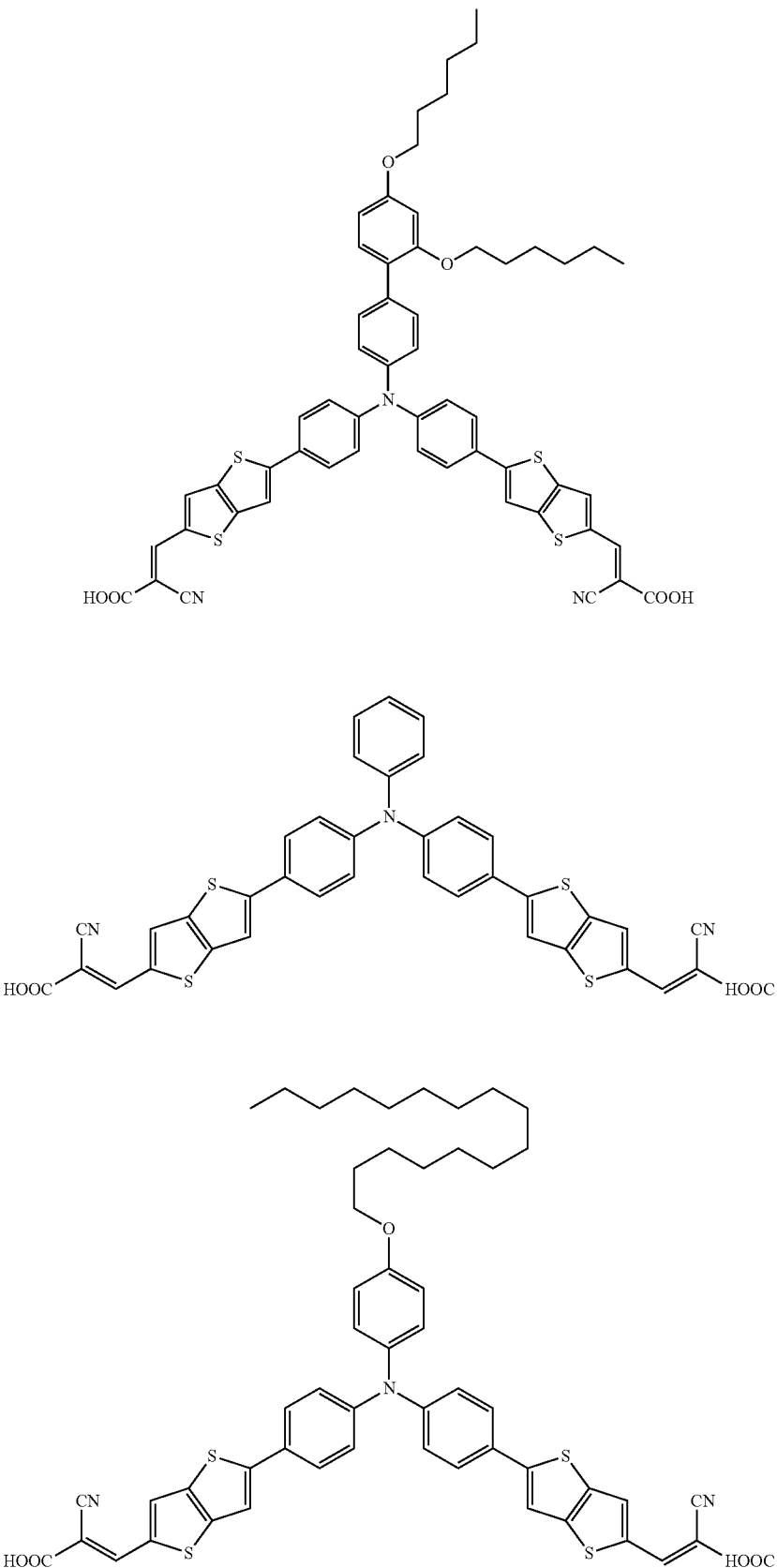

TABLE 1-continued
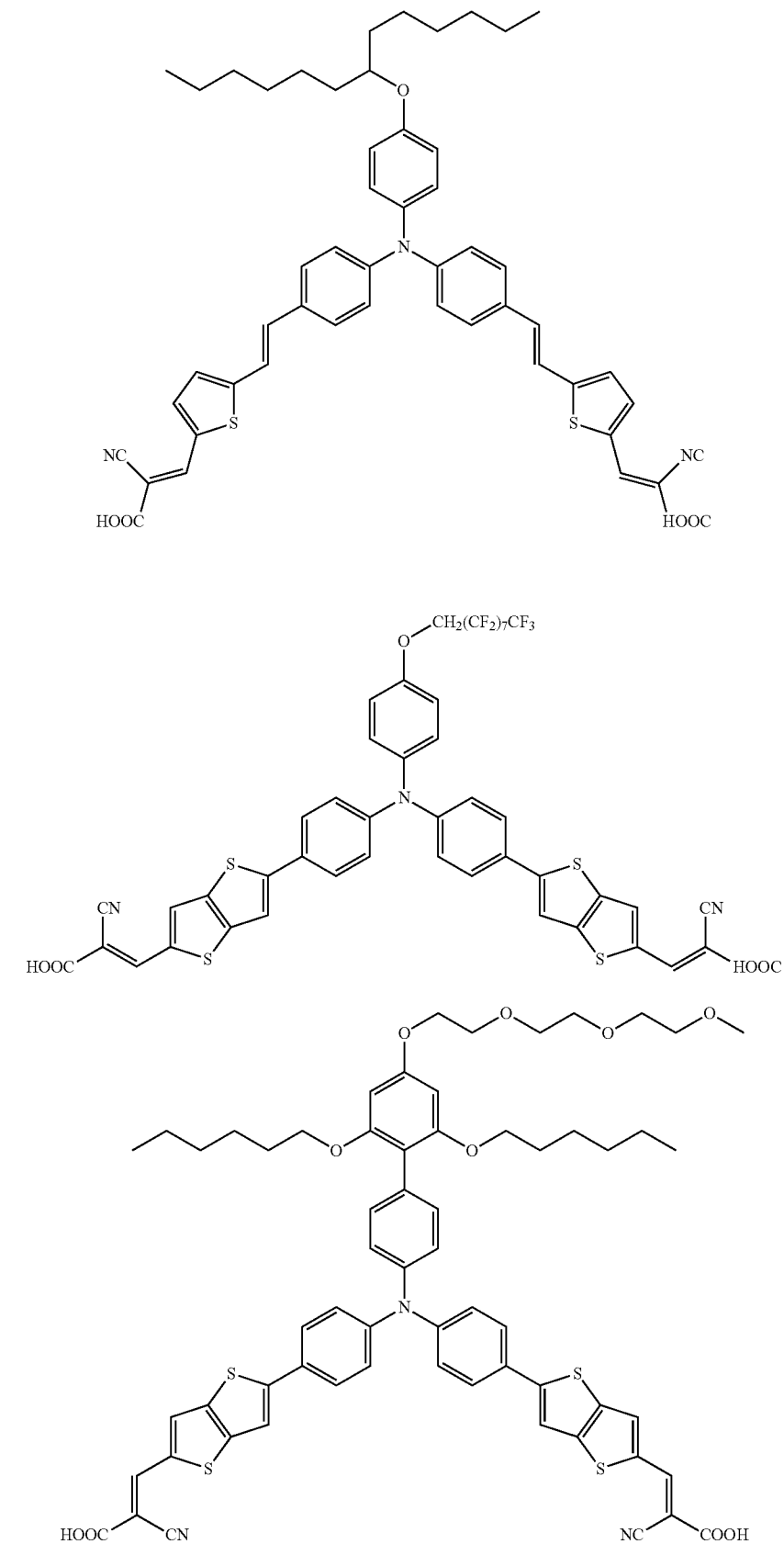

TABLE 1-continued
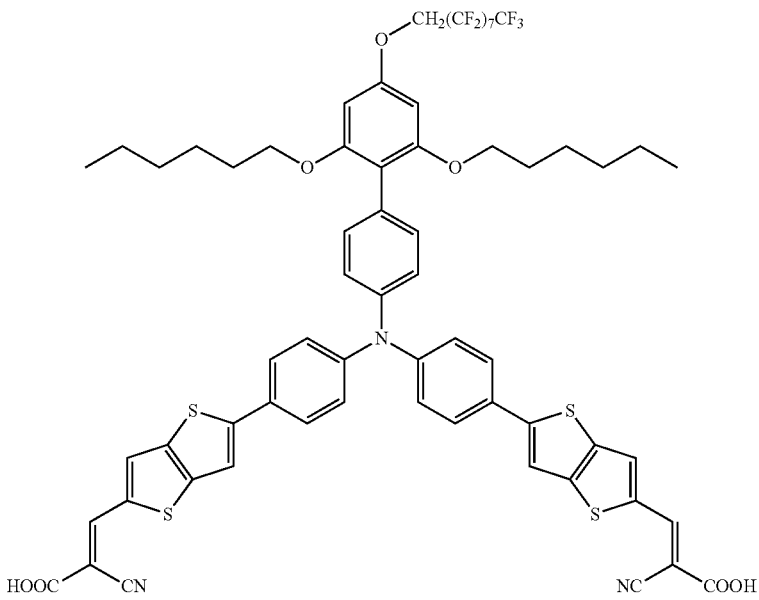
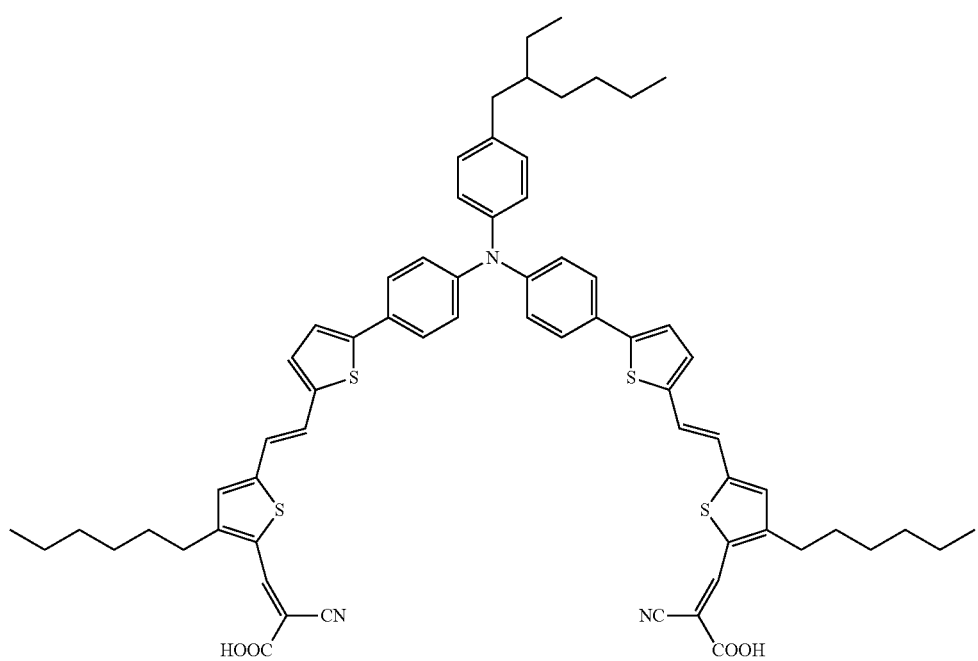 [SMILES: CCCCCCc1cc(/C=C/c2ccc(-c3ccc(N(c4ccc(CC(CC)CCCC)cc4)c4ccc(-c5ccc(/C=C/c6cc(CCCCCC)c(/C=C(\C#N)C(=O)O)s6)s5)cc4)cc3)s2)sc1/C=C(\C#N)C(=O)O]

TABLE 1-continued
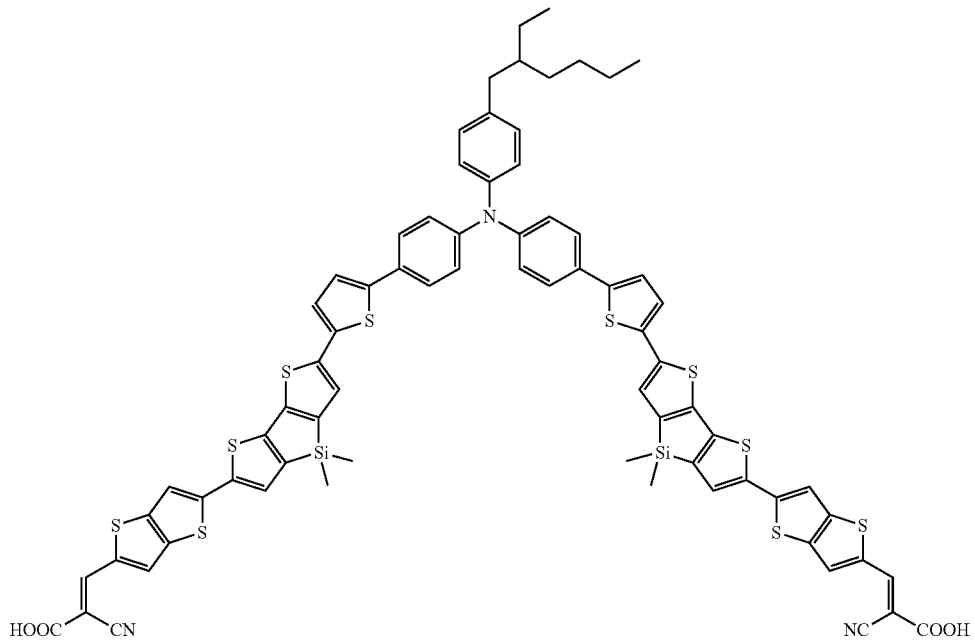 [SMILES: CCCCC(CC)Cc1ccc(N(c2ccc(-c3ccc(-c4cc5c(s4)-c4sc(-c6cc7sc(/C=C(\C#N)C(=O)O)cc7s6)cc4[Si]5(C)C)s3)cc2)c2ccc(-c3ccc(-c4cc5c(s4)-c4sc(-c6cc7sc(/C=C(\C#N)C(=O)O)cc7s6)cc4[Si]5(C)C)s3)cc2)cc1]
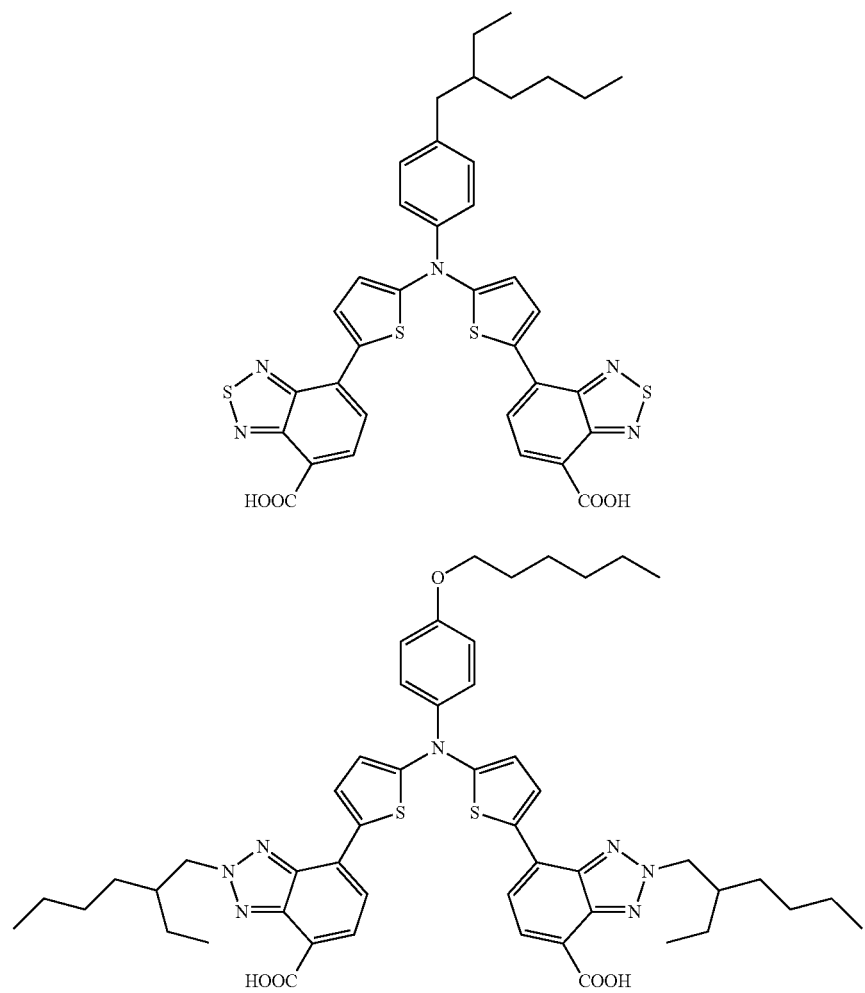

TABLE 1-continued
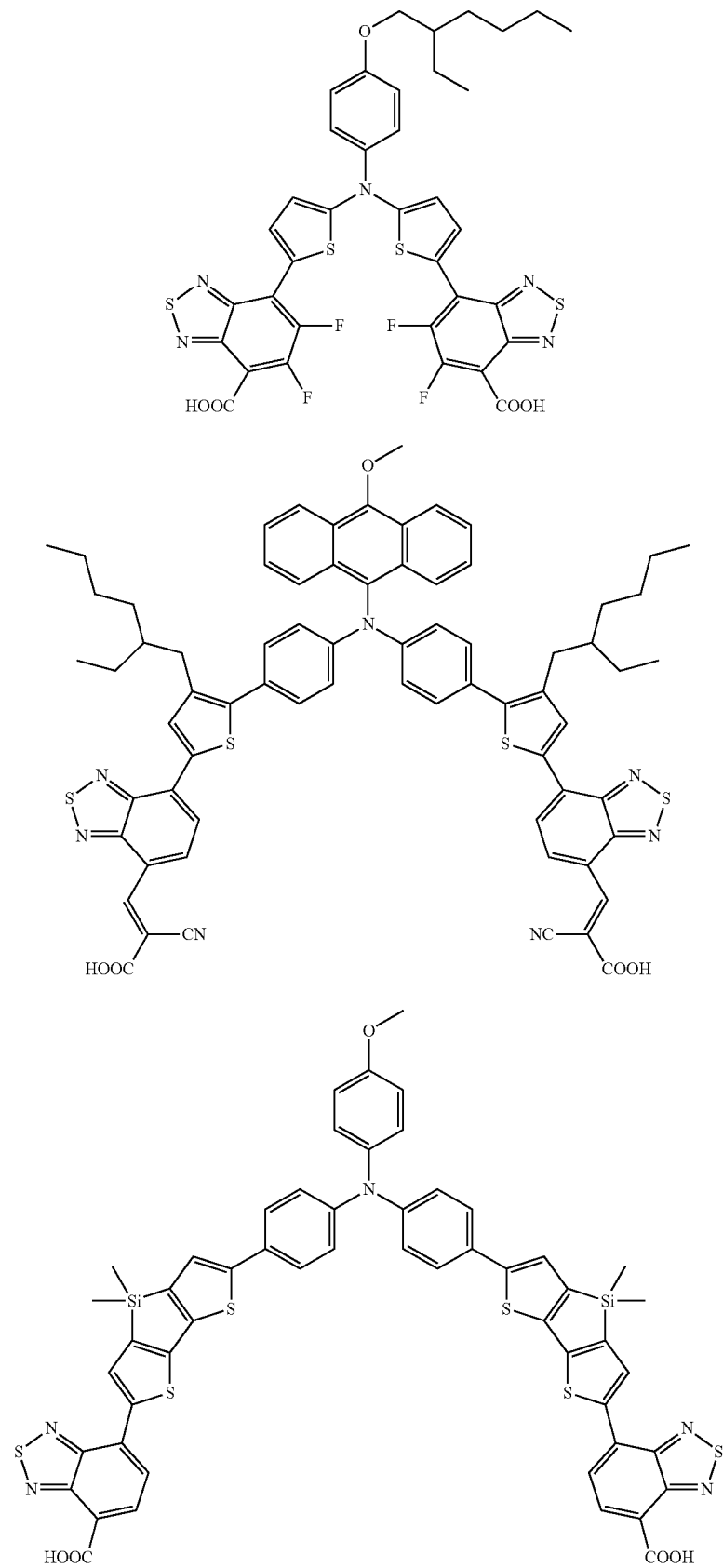

TABLE 1-continued
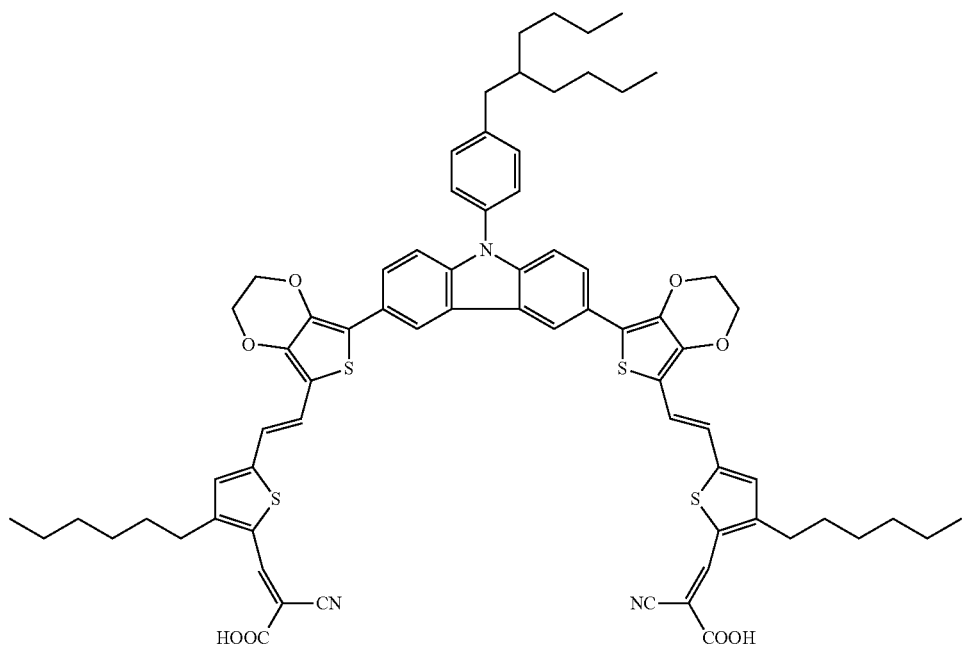 [SMILES: CCCCCCc1cc(/C=C/c2sc(-c3ccc4c(c3)c3cc(-c5sc(/C=C/c6cc(CCCCCC)c(/C=C(\C#N)C(=O)O)s6)c6c5OCCO6)ccc3n4-c3ccc(CC(CCCC)CCCC)cc3)c3c2OCCO3)sc1/C=C(\C#N)C(=O)O]
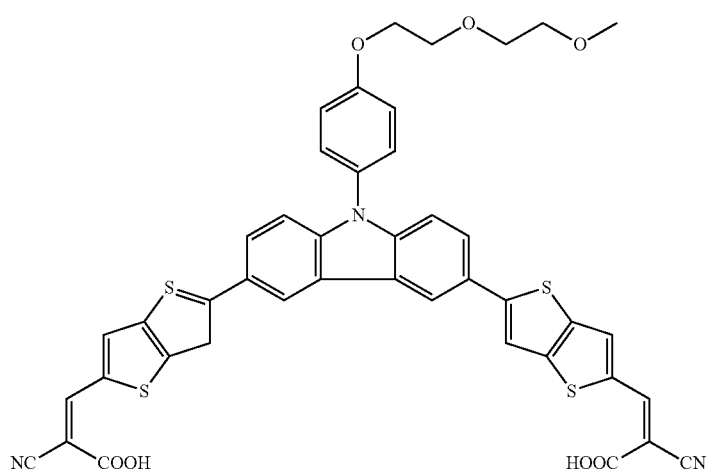

TABLE 1-continued
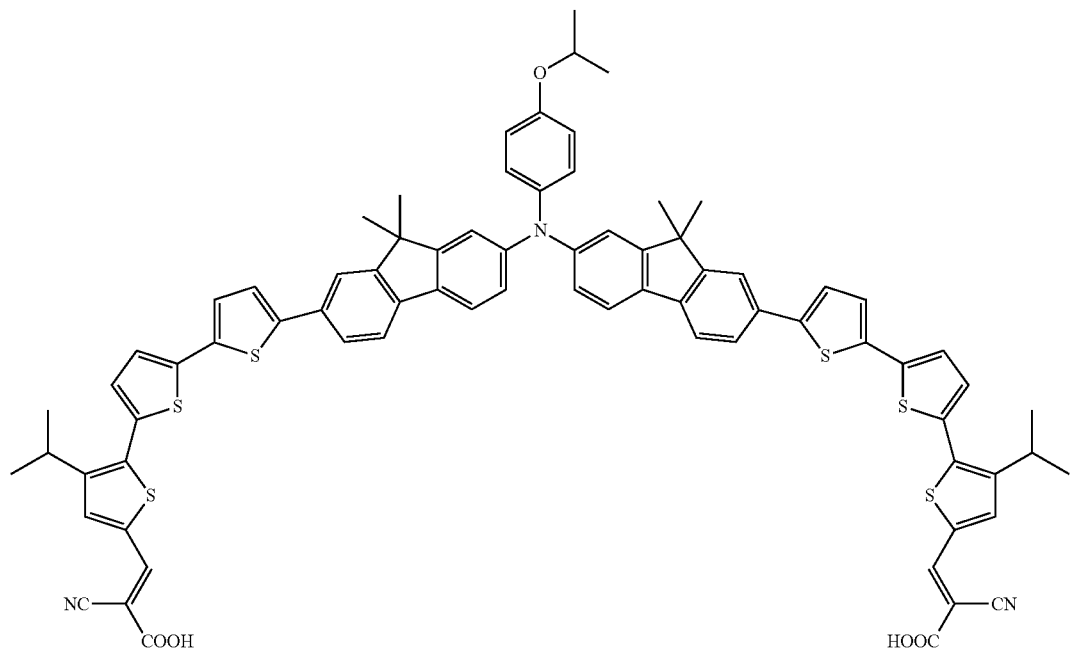 [SMILES: CC(C)Oc1ccc(N(c2ccc3c(c2)C(C)(C)c2cc(-c4ccc(-c5ccc(-c6sc(/C=C(\C#N)C(=O)O)cc6C(C)C)s5)s4)ccc2-3)c2ccc3c(c2)C(C)(C)c2cc(-c4ccc(-c5ccc(-c6sc(/C=C(\C#N)C(=O)O)cc6C(C)C)s5)s4)ccc2-3)cc1]
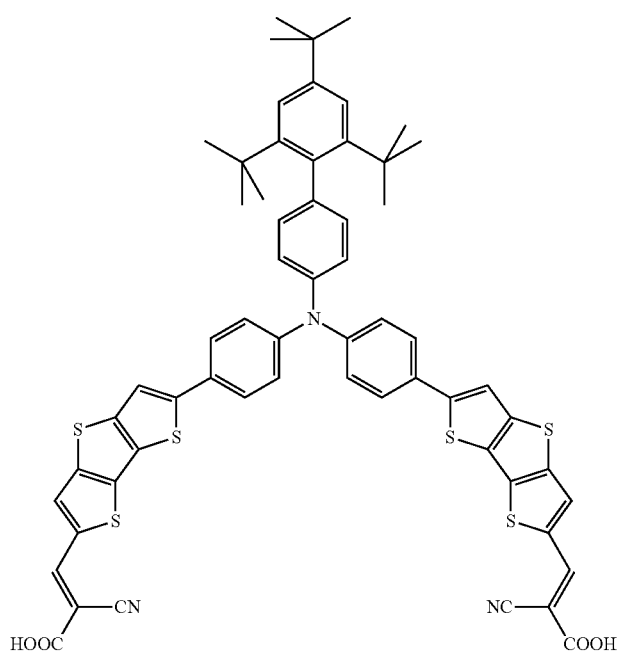 [SMILES: CC(C)(C)c1cc(C(C)(C)C)c(-c2ccc(N(c3ccc(-c4cc5sc6cc(/C=C(\C#N)C(=O)O)sc6c5s4)cc3)c3ccc(-c4cc5sc6cc(/C=C(\C#N)C(=O)O)sc6c5s4)cc3)cc2)c(C(C)(C)C)c1]

TABLE 1-continued
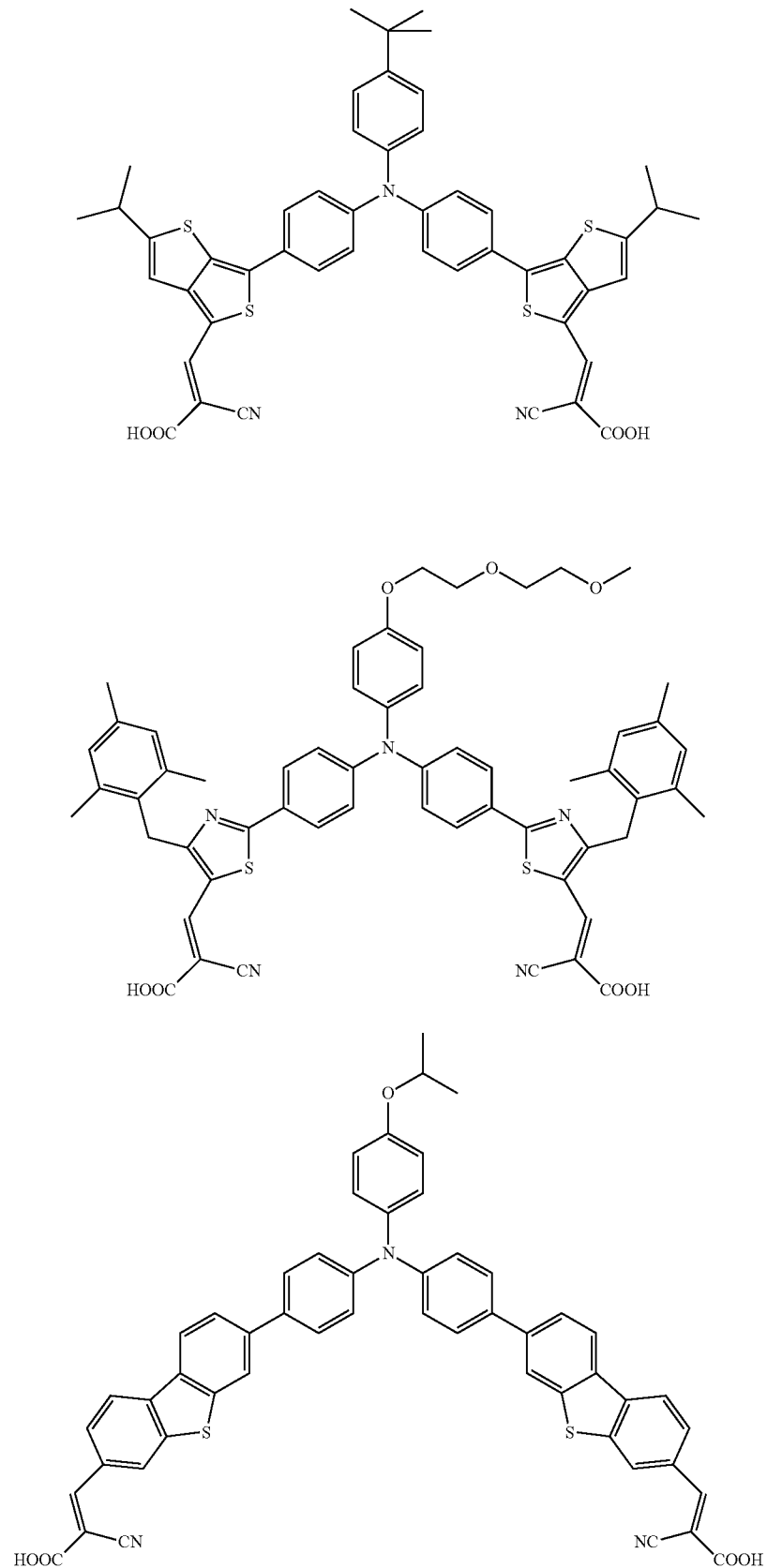

TABLE 1-continued
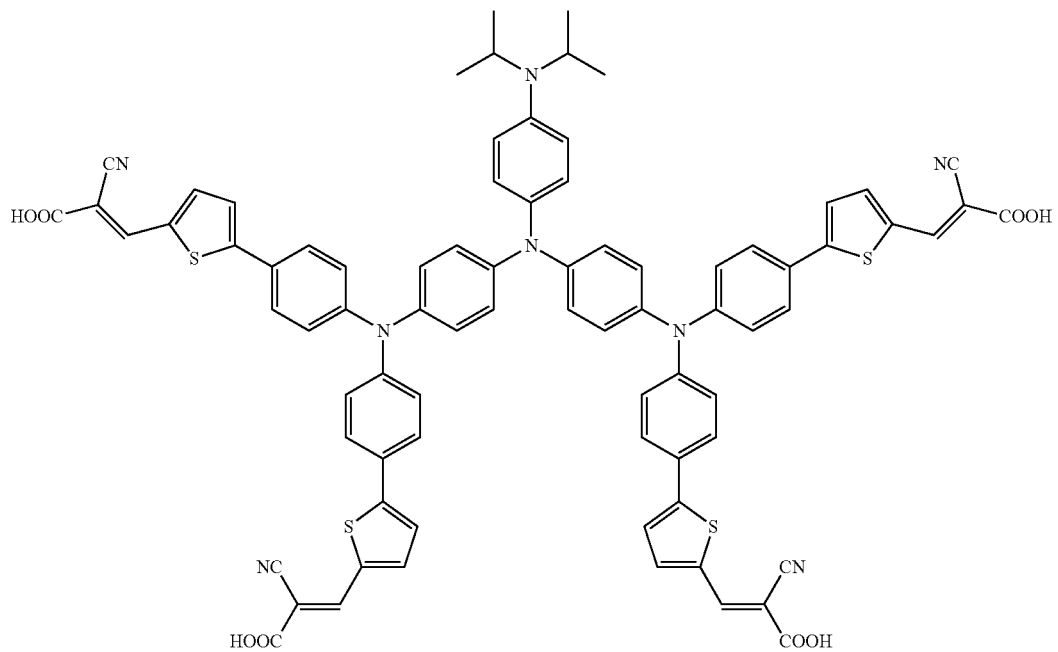 [SMILES: CC(C)N(c1ccc(N(c2ccc(N(c3ccc(-c4ccc(/C=C(\C#N)C(=O)O)s4)cc3)c3ccc(-c4ccc(/C=C(\C#N)C(=O)O)s4)cc3)cc2)c2ccc(N(c3ccc(-c4ccc(/C=C(\C#N)C(=O)O)s4)cc3)c3ccc(-c4ccc(/C=C(\C#N)C(=O)O)s4)cc3)cc2)cc1)C(C)C]
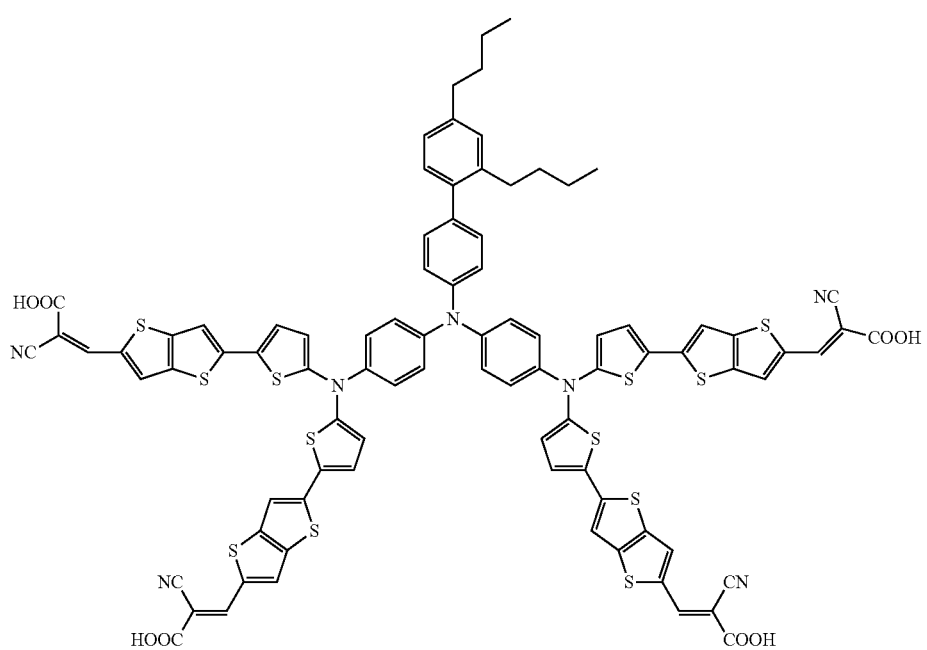 [SMILES: CCCCc1ccc(-c2ccc(N(c3ccc(N(c4ccc(-c5cc6sc(/C=C(/C#N)C(=O)O)cc6s5)s4)c4ccc(-c5cc6sc(/C=C(\C#N)C(=O)O)cc6s5)s4)cc3)c3ccc(N(c4ccc(-c5cc6sc(/C=C(\C#N)C(=O)O)cc6s5)s4)c4ccc(-c5cc6sc(/C=C(\C#N)C(=O)O)cc6s5)s4)cc3)cc2)c(CCCC)c1]

TABLE 1-continued
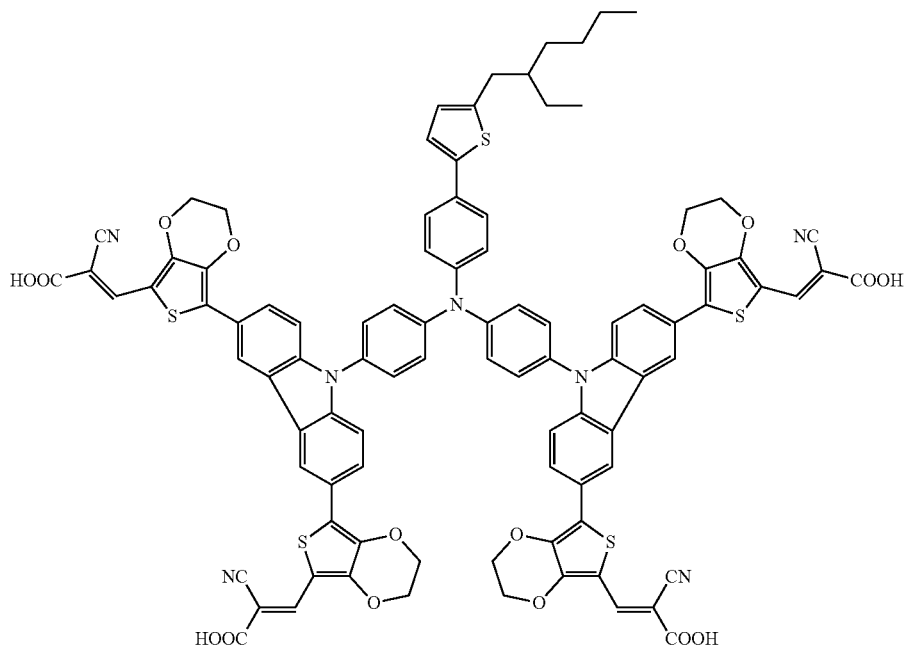 [SMILES: CCCCC(CC)Cc1ccc(-c2ccc(N(c3ccc(-n4c5ccc(-c6sc(/C=C(\C#N)C(=O)O)c7c6OCCO7)cc5c5cc(-c6sc(/C=C(\C#N)C(=O)O)c7c6OCCO7)ccc54)cc3)c3ccc(-n4c5ccc(-c6sc(/C=C(\C#N)C(=O)O)c7c6OCCO7)cc5c5cc(-c6sc(/C=C(\C#N)C(=O)O)c7c6OCCO7)ccc54)cc3)cc2)s1]
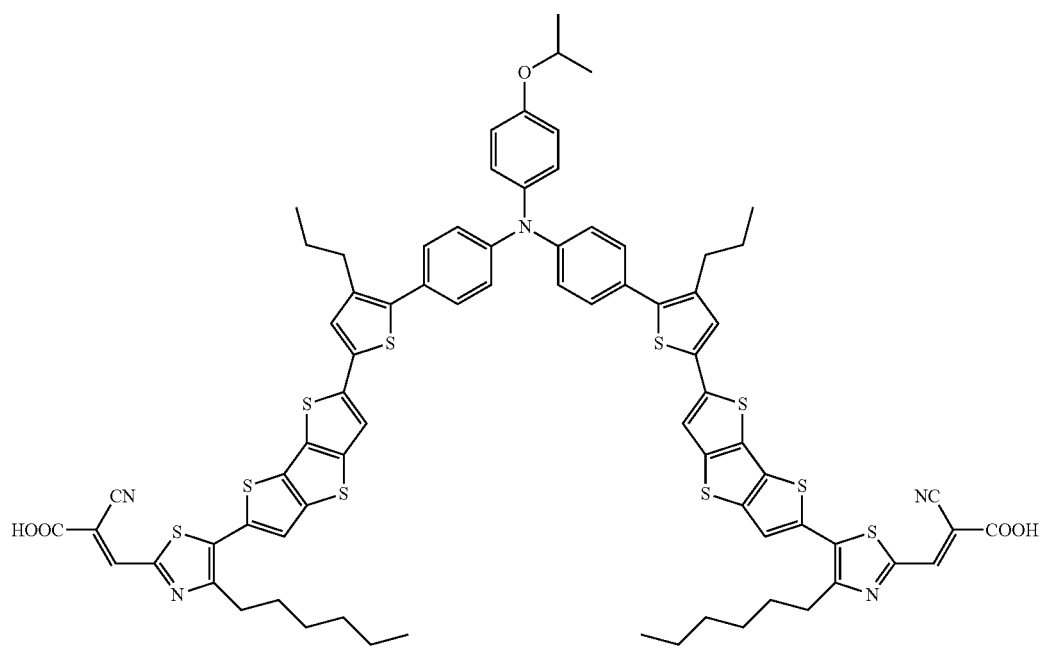 [SMILES: CCCCCCc1nc(/C=C(\C#N)C(=O)O)sc1-c1cc2sc3cc(-c4cc(CCC)c(-c5ccc(N(c6ccc(OC(C)C)cc6)c6ccc(-c7sc(-c8cc9sc%10cc(-c%11sc(/C=C(\C#N)C(=O)O)nc%11CCCCCC)sc%10c9s8)cc7CCC)cc6)cc5)s4)sc3c2s1]

TABLE 1-continued
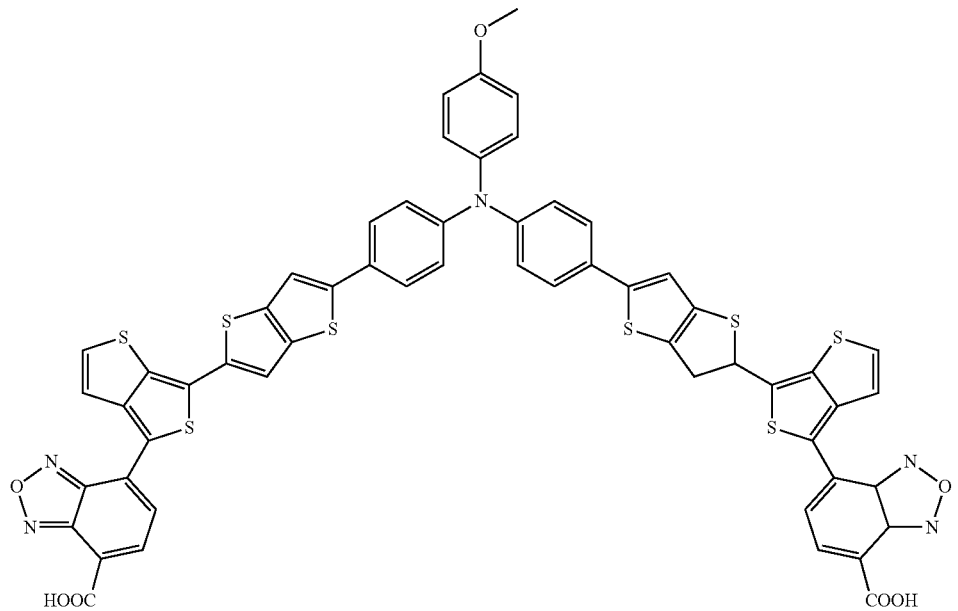 [SMILES: COc1ccc(N(c2ccc(-c3cc4c(s3)CC(c3sc(C5=CC=C(C(=O)O)C6NONC56)c5ccsc35)S4)cc2)c2ccc(-c3cc4sc(-c5sc(-c6ccc(C(=O)O)c7nonc67)c6ccsc56)cc4s3)cc2)cc1]
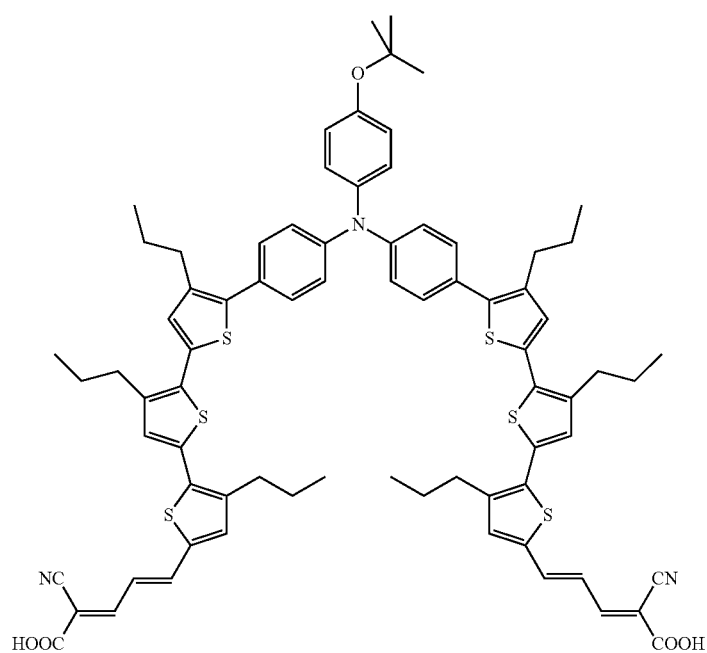 [SMILES: CCCc1cc(-c2sc(-c3sc(/C=C/C=C(\C#N)C(=O)O)cc3CCC)cc2CCC)sc1-c1ccc(N(c2ccc(OC(C)(C)C)cc2)c2ccc(-c3sc(-c4sc(-c5sc(/C=C/C=C(\C#N)C(=O)O)cc5CCC)cc4CCC)cc3CCC)cc2)cc1]

TABLE 1-continued

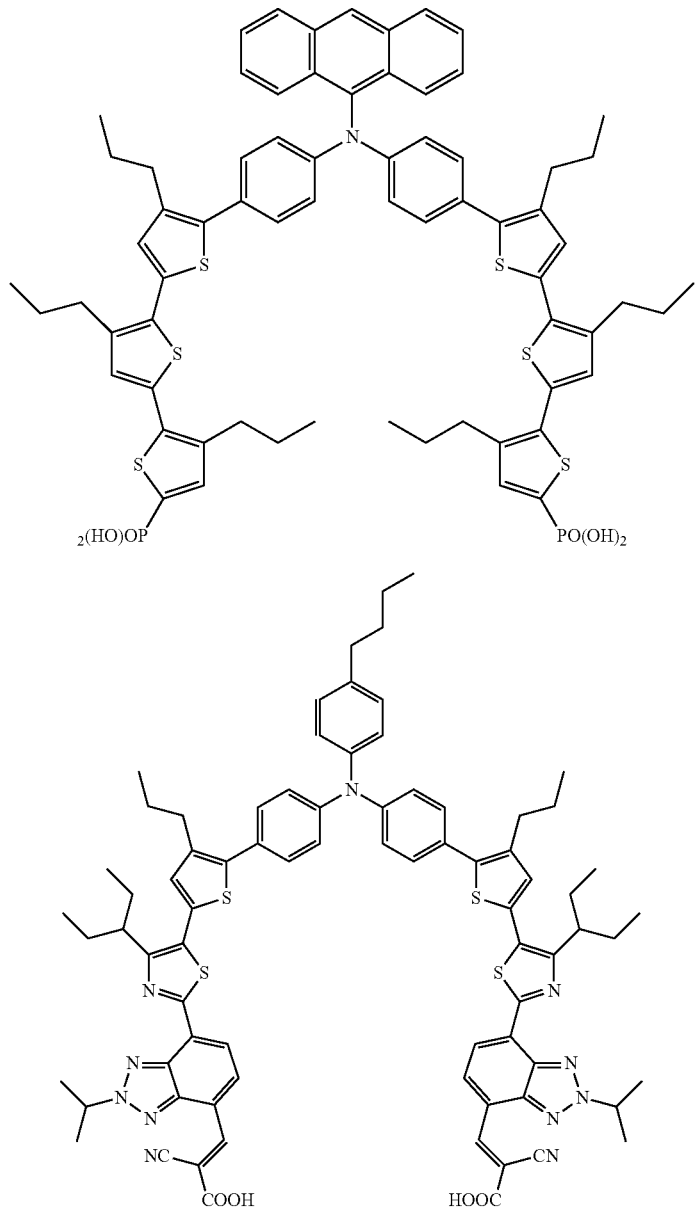

The organic dye having general formula (I), object of the present invention, can be obtained by means of several processes known in the art, such as, for example:
- reactions for the formation of double bonds, as described, for example, by Abbotto A. et al., in "*Energy & Environmental Science*" (2009), Vol. 2, pages 1094-1101;
- reactions for the formation of triple bonds (for example, the "cross-coupling" reaction of Sonogashira);
- reactions for the formation of aryl-aryl bonds (for example, "cross-coupling" reactions catalyzed by a metal, among which the Suzuki reaction or Stille reaction).

Further details relating to the preparation of the above organic dye having general formula (I) are provided in the following examples.

According to a further aspect, the present invention relates to a dye sensitized photoelectric transformation element, comprising at least one organic dye having general formula (I), said dye sensitized photoelectric transformation element being supported on particles of a semiconductor oxide.

The photoelectric transformation element according to the present invention can be prepared by means of a process for the preparation of a dye sensitized photoelectric transformation element for "Dye Sensitized Solar Cells" (DSSCs) according to the known art, except for the use of the organic dye having general formula (I).

The dye sensitized photoelectric transformation element according to the present invention, is preferably prepared by forming a thin film of a semiconductor oxide on a substrate and subsequently supporting at least one organic dye having general formula (I) on said thin film.

The substrate on which the thin film of semiconductor oxide is formed, preferably has a conductive surface, and is available on the market.

Said substrate is preferably selected, for example, from: glass; transparent polymers such as, for example, polyethylene terephthalate (PET), polyethylene naphthalate (PEN), polyethersulfone; or mixtures thereof. Said substrate preferably has a conductivity lower than or equal to 1,000Ω, more preferably lower than 100Ω.

A metal oxide is preferable as semiconductor oxide in the form of small particles. Said semiconductor oxide is preferably selected, for example, from: titanium dioxide, tin oxide, zinc oxide, tungsten oxide, zirconium oxide, gallium oxide, indium oxide, yttrium oxide, niobium oxide, tantalum oxide, vanadium oxide, or mixtures thereof. Titanium dioxide, tin oxide, zinc oxide, niobium oxide, indium oxide, or mixtures thereof, are even more preferably used; titanium dioxide, zinc oxide or tin oxide, or mixtures thereof, are more preferred; titanium dioxide is even more preferred.

The particles of semiconductor oxide preferably have an average diameter ranging from 1 nm to 500 nm, more preferably ranging from 1 nm to 100 nm, and those having a large diameter or a small diameter can be mixed, or used in multilayers.

The thin film of semiconductor oxide can be prepared using various known techniques, such as, for example: by spraying semiconductor oxide particles to form a thin film directly on the substrate; by means of electric deposition of a thin film of particles of semiconductor oxide using a substrate as electrode; by the application of a dispersion or paste of particles of semiconductor oxide, containing particles obtained by the hydrolysis of suitable precursors such as a metal halide or alkoxide, on a substrate (doctor blade technique) and subsequent drying, hardening, or sintering. The paste is preferably applied on a substrate: in this case, the dispersion can be obtained by dispersing the particles of semiconductor oxide, with a particle diameter ranging from 1 nm to 200 nm, in a dispersing medium, using a method known in the art.

Any dispersing medium can be used, provided it is capable of dispersing the particles of semiconductor oxide. Said dispersing medium is preferably selected, for example, from: water; alcohols such as, for example, ethanol; ketones, such as, for example, acetone, acetylacetone; hydrocarbons such as, for example, hexane; or mixtures thereof. Water is preferred as it minimizes the variation in the viscosity of the dispersion. A dispersion stabilizer can be optionally used in order to stabilize the dispersion of the semiconductor oxide particles.

Said dispersion stabilizer is preferably selected, for example, from acids, such as, for example, acetic acid, hydrochloric acid, nitric acid, acrylic acid; ketones such as, for example, acetylacetone; glycols such as, for example, diethyleneglycol, polyethyleneglycol; alcohols such as, for example, ethyl alcohol, polyvinyl alcohol; or mixtures thereof.

The substrate on which the dispersion is applied can be subjected to sintering, and the sintering temperature can be higher than or equal to 100° C., preferably higher than or equal to 200° C. In any case, the upper limit of the sintering temperature can be the melting point or the softening point of the substrate, normally 900° C., preferably 600° C. The sintering time is not necessarily specifically limited, but preferably does not exceed 24 hrs.

The thickness of the thin film on the substrate can range from 0.5 μm to 200 μm, preferably can range from 1 μm to 50 μm. The thin film of the semiconductor oxide can be subjected to a secondary treatment. For example, the thin film can be immersed in a solution of alkoxide, chloride, nitride, or sulfide, of the metal identical to the semiconductor oxide, and dried or sintered again, thus improving the thin film properties. The metal alkoxide can be selected, for example, from: titanium ethoxide, titanium iso-propoxide, titanium t-butoxide, tin n-dibutyl-diethossyl, or mixtures thereof. There are no particular limitations in the choice of solvent in which said metal alkoxide is dissolved, an alcohol solution of said metal alkoxide is preferably used. The metal chloride can be selected, for example, from: titanium tetrachloride, tin tetrachloride, zinc chloride, or mixtures thereof. There are no particular limitations in the choice of solvent in which said metal chloride is dissolved, an aqueous solution of said metal chloride is preferably used. The thin film of semiconductor oxide thus obtained can be composed of particles of semiconductor oxide.

The method for supporting the organic dye on the particles of semiconductor oxide in the form of thin film is not limited to a specific method.

A substrate having the thin film of semiconductor oxide formed on the same can be immersed, for example, in a solution obtained by dissolution of the organic dye having general formula (I) in a solvent capable of dissolving the same, or in a dispersion obtained by dispersing said organic dye having general formula (I). The concentration of the solution or dispersion can be suitably determined. The immersion temperature can range from −60° C. to 100° C., preferably can range from 0° C. to 50° C., it is more preferably room temperature (25° C.), and the immersion time can range from about 1 minute to 7 days, preferably can range from 1 hour to 26 hours. The solvent used for dissolving the organic dye can be selected, for example, from: methanol, ethanol, acetonitrile, methoxypropionitrile, chloroform, dichloromethane, dimethylsulfoxide, dimethylformamide, acetone, tetrahydrofuran, toluene, t-butanol, or mixtures thereof. The concentration of the solution can normally range from $1 \times 10^{-6}$ M to 1 M, preferably can range from $1 \times 10^{-5}$ M to $1 \times 10^{-1}$ M. In this way, a dye sensitized photoelectric transformation element can be obtained, comprising particles of semiconductor oxide on a dye sensitized thin film.

The organic dye having general formula (I) can be optionally mixed with other organic dyes or dyes based on metal complexes. Dyes based on metal complexes which can be mixed, can include, but are not specifically limited to, ruthenium dipyridine complexes, in both neutral and ionic form, phthalocyanines and porphyrins of various metals such as, for example, zinc, copper, cobalt, nickel, iron, ruthenium, platinum, manganese; other metal-free organic dyes which can be mixed can include phthalocyanines, porphyrins, cyanines, merocyanines, oxonols, triphenylmethane dyes, methine dyes such as the acrylated dyes described in european patent application EP 1,311,001, xanthenes, azo, anthraquinones, perylene dyes (as described by Nazeeruddin M. K., in "*Journal of the American Chemical Society*" (1993), Vol. 115, pages 6382-6390). If two or more types of organic dyes are used in combination, they can be absorbed in sequence on a thin layer of semiconductor oxide, or mixed, dissolved and absorbed.

In order to prevent the aggregation of the organic dye on the thin layer of semiconductor oxide, the organic dye having general formula (I) can be optionally mixed with an inclusion compound (co-adsorbent): the mixture obtained can be adsorbed on a thin layer of semiconductor oxide using methods known in the art. The inclusion compound can be selected, for example, from: cholic acids such as deoxycholic acid, dehydrodeoxycholic acid, chenodeoxycholic acid, methyl ester of cholic acid, sodium salt of cholic acid; polyethylene oxides; crown ethers; cyclodextrins; calixarenes, polyethyleneoxides; or mixtures thereof.

After supporting the organic dye, the surface of a semiconductor electrode can be treated with a compound which can be selected from: amine compounds such as, for example, 4-t-butylpyridine; alcohols such as, for example, methanol, ethanol, butanol, or mixtures thereof; organic acids such as, for example, acetic acid, propionic acid, or mixtures thereof. For example, a substrate on which a thin film of semiconductor oxide particles has been formed combined with a dye can be immersed in a solution of an amine in ethanol.

According to a further aspect, the present invention also relates to a Dye Sensitized Solar Cell (DSSC) comprising the dye sensitized photoelectric transformation element described above.

Said Dye Sensitized Solar Cell (DSSC) can be prepared by means of methods known in the art for the preparation of solar cells, using a photoelectric transformation element of the known art, except for the use of a dye sensitized photoelectric transformation element, comprising particles of semiconductor oxide in which the organic dye having general formula (I) is supported. The Dye Sensitized Solar Cell (DSSC) can comprise a photoelectric transformation element as electrode (negative electrode) in which the organic dye having general formula (I) is supported on particles of semiconductor oxide, a counter-electrode (positive electrode), a redox electrolyte, a hole transporting material, or a semiconductor compound of the p type.

The Dye Sensitized Solar Cell (DSSC) according to the present invention is preferably prepared by the deposition of a titanium dioxide paste on a transparent conductive substrate; sintering of the coated substrate to form a thin film of titanium dioxide; immersion of the substrate on which the substrate of thin film of titanium dioxide is formed in a solution in which the organic dye having general formula (I) is dissolved, so as to form an electrode with a film of titanium dioxide with absorbed dye; production of a second transparent conductive substrate on which a counter-electrode is formed; formation of a hole which penetrates through the second transparent conductive substrate and the counter-electrode; laying of a film of thermoplastic polymer between the counter-electrode and the electrode with a film of titanium dioxide with absorbed dye and hot pressure in order to bind the counter-electrode and the electrode with the film of titanium dioxide; injection of the electrolyte into the film of thermoplastic polymer positioned between the counter-electrode and the electrode with the film of titanium dioxide through the hole; and closing of the hole with suitable materials which can be selected, for example, from thermoplastic polymers.

The redox electrolyte, the hole transporting material, or the semiconductive compound of the p type can be in liquid form (for example, ionic liquids), or in coagulated form (gel and gel phase), or even solid. The liquid can be selected, for example, from those obtained by dissolving the redox electrolyte, a dissolved salt, the hole transporting material, or the semiconductive compound of the p type in a solvent, and a salt dissolved at room temperature. The coagulated form (gel and gel phase) can be selected, for example, from those obtained by inclusion of the redox electrolyte, a dissolved salt, the hole transporting material, or the semiconductive compound of the p type in a polymer matrix or in a low-molecular-weight gelling agent. The solid can be selected, for example, from the redox electrolyte, a dissolved salt, the hole transporting material, or the semiconductive compound of the p type.

The hole transporting material can be selected, for example, from: amine derivatives; conductive polymers such as, for example, polyacetylene, polyaniline, polythiophene; or discotic liquid crystalline phases such as, for example, triphenylene. The semi-conductive compound of the p type can be selected, for example, from copper iodide (CuI), copper thiocyanate (CuSCN). As counter-electrode, those having a conductivity and catalytic function on the reduction of the redox electrolyte and, for example, those obtained by the deposition of platinum, carbon, rhodium, ruthenium, on a glass or polymeric film, or by applying conductive particles on the same, are preferably used.

The redox electrolyte used in the Dye Sensitized Solar Cell (DSSC) according to the present invention, can include a redox electrolyte based on a halogen comprising halogenated compounds comprising a halogen ion as counter-ion and a halogen molecule; metal redox electrodes such as ferrocyanide-ferricyanide or ferrocene-ferricinium ion; metal complexes such as cobalt complexes; redox organic electrolytes such as, for example, alkylthio-alkyldisulfide, viologen dye, hydroquinone-quinone. Redox electrolytes based on halogen are preferred. As halogen molecule included in the halogenated redox electrolyte, an iodine molecule is preferred. As halogenated compounds comprising a halogen ion as counter-ion, a halogenated inorganic salt can be used such as, for example, lithium iodide (LiI), sodium iodide (NaI), potassium iodide (KI) caesium iodide (CsI), ammonium iodide [($NH_4$)I], calcium diiodide ($CaI_2$), magnesium diiodide ($MgI_2$), barium diiodide ($BaI_2$), copper iodide (CuI), copper diiodide ($CuI_2$), zinc diiodide ($ZnI_2$), or a halogen of organic ammonium such as, for example, tetra alkyl-ammonium iodide, imidazolium iodide, pyridinium iodide, or iodine ($I_2$).

If the redox electrolyte is in the form of a solution, an electrochemically inert solvent can be used. The following can be used, for example: acetonitrile, propylenecarbonate, ethylenecarbonate, 3-methoxy-propionitrile, methoxy-acetonitrile, valeronitrile, ethyleneglycol, propyleneglycol, diethyleneglycol, triethyleneglycol, butyrolactone, dimethoxyethane, dimethylcarbonate, 1,3-dioxolane, methylformiate, 2-methyltetrahydrofuran, 3-methoxy-oxazolidin-2-one, sulfolane, tetrahydrofuran, water. Acetonitrile, valeronitrile, propylenecarbonate, ethylenecarbonate, 3-methoxy-propionitrile, ethylene-glycol, 3-methoxy-oxazolidin-2-one, butyrolactone, are preferred. Said solvents can be used alone or mixed with each other.

As positive electrolyte in gel phase, those obtained by including the electrolyte or the electrolyte solution in an oligomeric or polymeric matrix, or including the electrolyte or the electrolyte solution in a starch-based gelling agent, can be used.

The concentration of the redox electrolyte preferably ranges from 0.01% by weight to 99% by weight, more preferably ranges from 0.1% by weight to 30% by weight, with respect to the total weight of the solution.

The Dye Sensitized Solar Cell (DSSC) according to the present invention can be obtained by preparing a photoelectric transformation element (negative electrode—anode) in which the organic dye having general formula (I) is supported on particles of semiconductive oxide on a substrate, and a counter-electrode (positive electrode) opposite the same, and inserting a solution containing the redox electrolyte between them.

The present invention will be further illustrated hereunder by the following examples which are provided for purely illustrative and non-limiting purposes of the same invention.

EXAMPLES

Reagents and Materials

The reagents and materials used in the following examples of the invention, their optional pretreatments and their producer, are indicated in the following list:
- tetrahydrofuran (THF) of Aldrich: anhydrified by distillation on lithium aluminium hydride (LiAlH$_4$) in an inert atmosphere;
- potassium t-butoxide (t-BuOK) of Aldrich: used as such;
- dimethylformamide (DMF) of Aldrich: used as such;
- phosphorous oxychloride (POCl$_3$) of Aldrich: used as such;
- 1,2-dichloroethane of Acros: used as such;
- 2-cyanoacetic acid of Aldrich: used as such;
- piperidine of Aldrich: used as such;
- chloroform (CHCl$_3$) of Carlo Erba: used as such;
- dichloromethane (CH$_2$Cl$_2$) of Carlo Erba: used as such;
- ethyl acetate (AcOEt) of Carlo Erba: used as such;
- sodium sulfate (Na$_2$SO$_4$) of Carlo Erba: used as such;
- potassium carbonate (K$_2$CO$_3$) of Aldrich: used as such;
- 1,1'-bis(diphenylphosphine)ferrocene-palladium(II)dichloride [Pd(dppf)Cl$_2$] complexed with dichloromethane of Aldrich: used as such;
- methanol (MeOH) of Carlo Erba: used as such;
- toluene of Carlo Erba: used as such;
- n-hexane of Carlo Erba: used as such;
- sodium acetate (AcONa) of Aldrich: used as such;
- diethyl ether (Et$_2$O) of Carlo Erba: used as such;
- N-bromosuccinimide (NBS) of Aldrich: recrystallized from water;
- ammonium chloride (NH$_4$Cl) of Carlo Erba: used as such;
- trimethylsilylacetylene of Aldrich: used as such;
- bis(triphenylphosphine)palladium(II)dichloride [Pd(PPh$_3$)$_2$Cl$_2$] of Aldrich: used as such;
- triphenylphosphine (PPh$_3$) of Aldrich: used as such;
- copper iodide (CuI) of Aldrich: used as such;
- triethylamine (NEt$_3$) of Aldrich: used as such;
- titanium tetrachloride (TiCl$_4$) of Aldrich: used as such;
- dimethylsulfoxide (DMSO) of Carlo Erba: used as such.
- deuterated chloroform (CDCl$_3$) of Acros: used as such.

The following characterization methods were used in the following examples.

Reactions and Products Obtained

The reactions were carried out by means of thin layer chromatography, on Polygram Sil G/UV254 silica gel having a thickness of 0.20 mm, revealing the spots separated by irradiation of the supports with UV light (254 nm and 365 nm).

The compounds obtained were purified by means of flash chromatography using Merck 9385 silica gel having a particle size ranging from 230 mesh to 400 mesh (40 mm-63 mm) and a pore size equal to 60 Å. Said flash chromatography was carried out as described by Still, W. C. et al. in "*Journal of Organic Chemistry*" (1978), Vol. 43, pages 2923-2925.

NMR Spectra

The NMR spectra of the compounds obtained were carried out using a NMR Bruker ANX-500 spectrometer.

For this purpose, about 10 mg of the sample to be examined were dissolved in about 0.8 ml of a suitable solvent deuterated directly in the glass tube used for the measurement. The scale of the chemical shifts was calibrated in relation to the tetramethylsilane signal set at 0 ppm.

Absorption Spectra

The absorption spectra in a solution of the compounds prepared, in ultraviolet and visible (UV-Vis) (375 nm-800 nm), were acquired in transmission using a Jasco V-570 spectrophotometer.

For this purpose, about 5 mg of the sample to be examined were dissolved in about 10 ml of a suitable solvent: 2 ml of said solution were placed in a quartz cuvette with an optical path of 1 cm.

Example 1

Preparation of the Compound F1

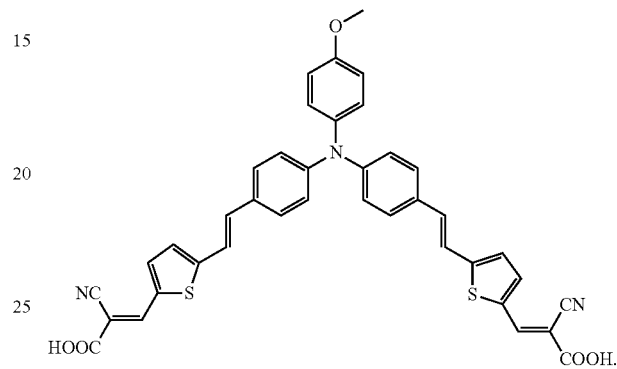

(F1)

The compound F1 was obtained according to the following Scheme 1:

Scheme 1

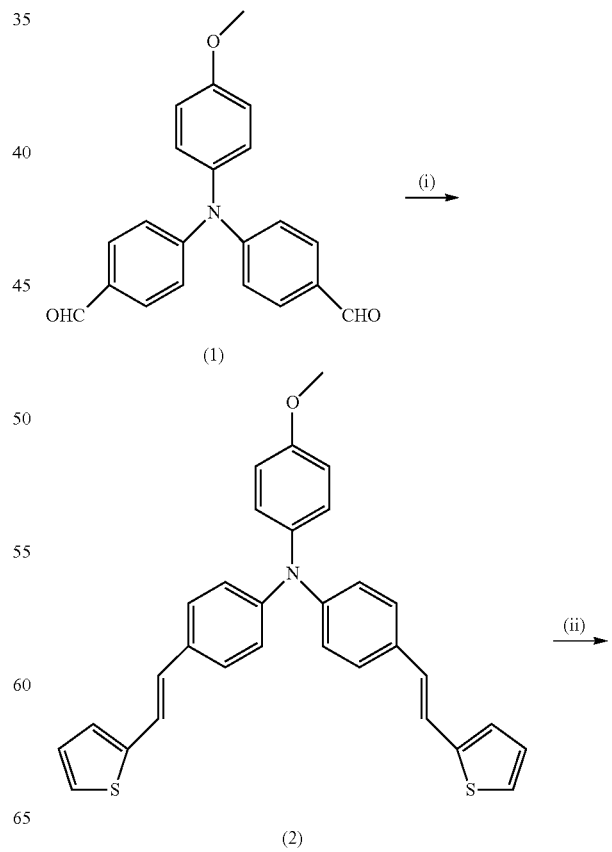

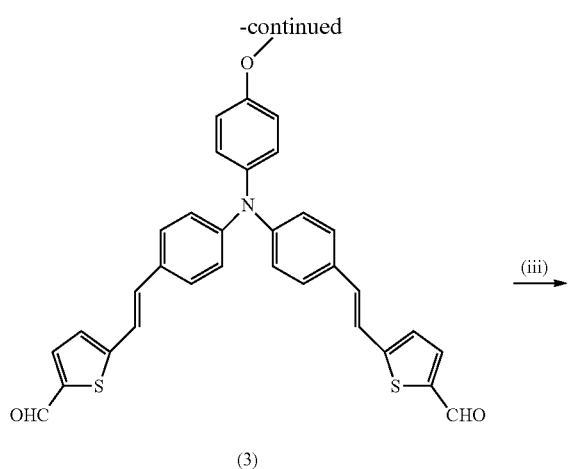

(3)

wherein: (i) indicates diethyl-thiophen-2-yl-methylphosphonate, potassium t-butoxide (t-BuOK), anhydrous tetrahydrofuran (THF); (ii) indicates dimethylformamide (DMF), phosphorous oxychloride (POCl$_3$), 1,2-dichloroethane; (iii) indicates 2-cyanoacetic acid, piperidine, chloroform (CHCl$_3$).

Synthesis of N,N-bis-{4-[(thien-2-yl)vin-2-yl]phenyl}-p-methoxyaniline (2)

0.63 g (1.9 mmoles) of N,N-bis-(4-formylphenyl)aniline (1) [obtained as described by El-Khouly M. E. et al., in "*The Journal of Physical Chemistry B*" (2008), Vol. 112, pages 3910-3917], 1.17 g (5.0 mmoles) of diethyl thiophen-2-yl-methylphosphonate [obtained as described by Wang Z.-S. et al., in "*The Journal of Physical Chemistry C*" (2007), Vol. 111, pages 7224-7230] and 30 ml of anhydrous tetrahydrofuran (THF), were introduced into a 250 ml flask: 0.56 g (5.0 mmoles) of potassium t-butoxide (t-BuOK) were then added, in small portions, to the solution obtained. The reaction mixture obtained was left, under stirring, at room temperature (25° C.), for 16 hours. The reaction was then quenched by adding 30 ml of water and subsequently 30 ml of ethyl acetate (AcOEt) and the whole mixture was left, under stirring, for 1 hour and then extracted with dichloromethane (CH$_2$Cl$_2$) (3×20 ml). The organic phase obtained was washed with water (3×15 ml) and dried on sodium sulfate (Na$_2$SO$_4$). After eliminating the solvent by evaporation at reduced pressure, a brown-coloured residue was obtained, which was purified by means of flash chromatography on silica gel, using dichloromethane (CH$_2$Cl$_2$) as eluent, obtaining 0.43 g (yield 46%) of N,N-bis-{4-[(thien-2-yl)vin-2-yl]phenyl}-p-methoxyaniline (2), as an orange solid, having a melting point of 173° C.-174° C.

Said N,N-bis-{4-[(thien-2-yl)vin-2-yl]phenyl}-p-methoxyaniline (2) was characterized by means of $^1$H-NMR (500 MHz; CDCl$_3$; Me$_4$Si) obtaining the following spectrum: $\delta_H$ 7.32 (4 H, d, J 8.6), 7.16 (2 H, t, J 5.0), 7.11 (2 H, d, J 15.9), 7.09 (2 H, d, J 8.9), 7.04-6.97 (8 H, m), 6.89-6.84 (4 H, m), 3.80 (3 H, s).

Synthesis of N,N-bis-{4-[(5-formylthien-2-yl)vin-2-yl]phenyl}-p-methoxyaniline (3)

0.32 g (4.4 mmoles) of dimethyl formamide (DMF) were introduced into a 100 ml flask, previously anhydrified and maintained under a flow of nitrogen (N$_2$), and subsequently, after cooling to a temperature of −10° C., 0.68 g (4.4 mmoles) of phosphorous oxychloride (POCl$_3$) were slowly added dropwise: the formation of a vitreous white solid was observed and after 30 minutes, 20 ml of 1,2-dichloroethane were added. After the complete dissolution of the reaction mixture, 0.43 g (0.87 mmoles) of N,N-bis-{4-[(thien-2-yl)vin-2-yl]phenyl}-p-methoxyaniline (2), obtained as described above, dissolved in 30 ml of 1,2-dichloroethane, were added. The reaction mixture was left, under stirring, at room temperature (25° C.), for 16 hours. The reaction was then quenched by adding 50 ml of a saturated aqueous solution of potassium carbonate (K$_2$CO$_3$) and the whole mixture was left, under stirring, for 1 hour, and then extracted with dichloromethane (CH$_2$Cl$_2$) (3×20 ml). The organic phase obtained was washed with water (2×15 ml) and dried on sodium sulfate (Na$_2$SO$_4$). After eliminating the solvent by evaporation at reduced pressure, 0.44 g (yield 92%) of N,N-bis-{4-[(5-formylthien-2-yl)vin-2-yl]phenyl}-p-methoxyaniline (3) were obtained, as a dark orange solid.

Said N,N-bis-{4-[(5-formylthien-2-yl)vin-2-yl]-phenyl}-p-methoxyaniline (3) was characterized by means of $^1$H-NMR (500 MHz; CDCl$_3$; Me$_4$Si) obtaining the following spectrum: $\delta_H$ 9.85 (1 H, s), 7.65 (2 H, d, J 3.9), 7.37 (4 H, d, J 8.7), 7.13-7.08 (8 H, m), 7.04 (4 H, d, J 8.7), 6.88 (2 H, d, J 8.9), 3.80 (3 H, s).

Synthesis of the Compound (F1)

0.44 g (0.80 mmoles) of N,N-bis-{4-[(5-formylthien-2-yl)vin-2-yl]phenyl}-p-methoxyaniline (3), obtained as described above, and 30 ml of chloroform (CHCl$_3$), were introduced into a 50 ml flask: 0.41 g (4.8 mmoles) of 2-cyanoacetic acid were then added to the solution obtained. The reaction mixture obtained was cooled to 0° C. with an ice bath and a solution of piperidine (0.54 g, 6.4 mmoles) in 5 ml of chloroform (CHCl$_3$) was subsequently slowly added dropwise. At the end of the dripping, the reaction mixture was heated to the reflux temperature of the solvent, for 8 hours. The reaction mixture was then left to cool to room temperature (25° C.) and the formation of a precipitate was observed, which was recovered by filtration at reduced pressure obtaining a dark red solid which was subsequently dissolved in 20 ml of water and treated with 10 ml of a solution of hydrochloric acid at 10%: in this phase, the formation of a dark precipitate was observed, which was in its turn recovered by filtration at reduced pressure, washed with water (2×15 ml) and dried under vacuum obtaining 0.25 g (yield 56%) of the compound (F1) as a purple solid.

Said compound (F1) was characterized by means of $^1$H-NMR (500 MHz; DMSO-d$_6$; Me$_4$Si) obtaining the following spectrum: $\delta_H$ 8.45 (2H, s), 7.94 (2 H, d, J 4.0), 7.59 (4 H, d, J 8.7), 7.45 (2 H, d, J 16.1), 7.41 (2 H, d, J 4.0), 7.23 (2 H, d, J 16.1), 7.12 (2 H, d, J 8.9), 7.00 (2 H, d, J 9.1), 6.98 (4 H, d, J 8.7), 3.78 (3H, s).

Example 2

Preparation of the Compound F2

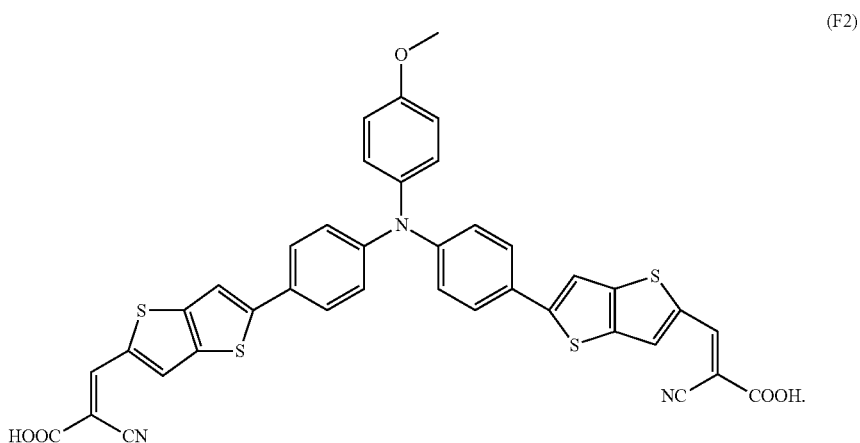 [SMILES: COc1ccc(N(c2ccc(-c3cc4sc(/C=C(\C#N)C(=O)O)cc4s3)cc2)c2ccc(-c3cc4sc(/C=C(\C#N)C(=O)O)cc4s3)cc2)cc1]

The compound F2 was obtained according to the following Scheme 2:

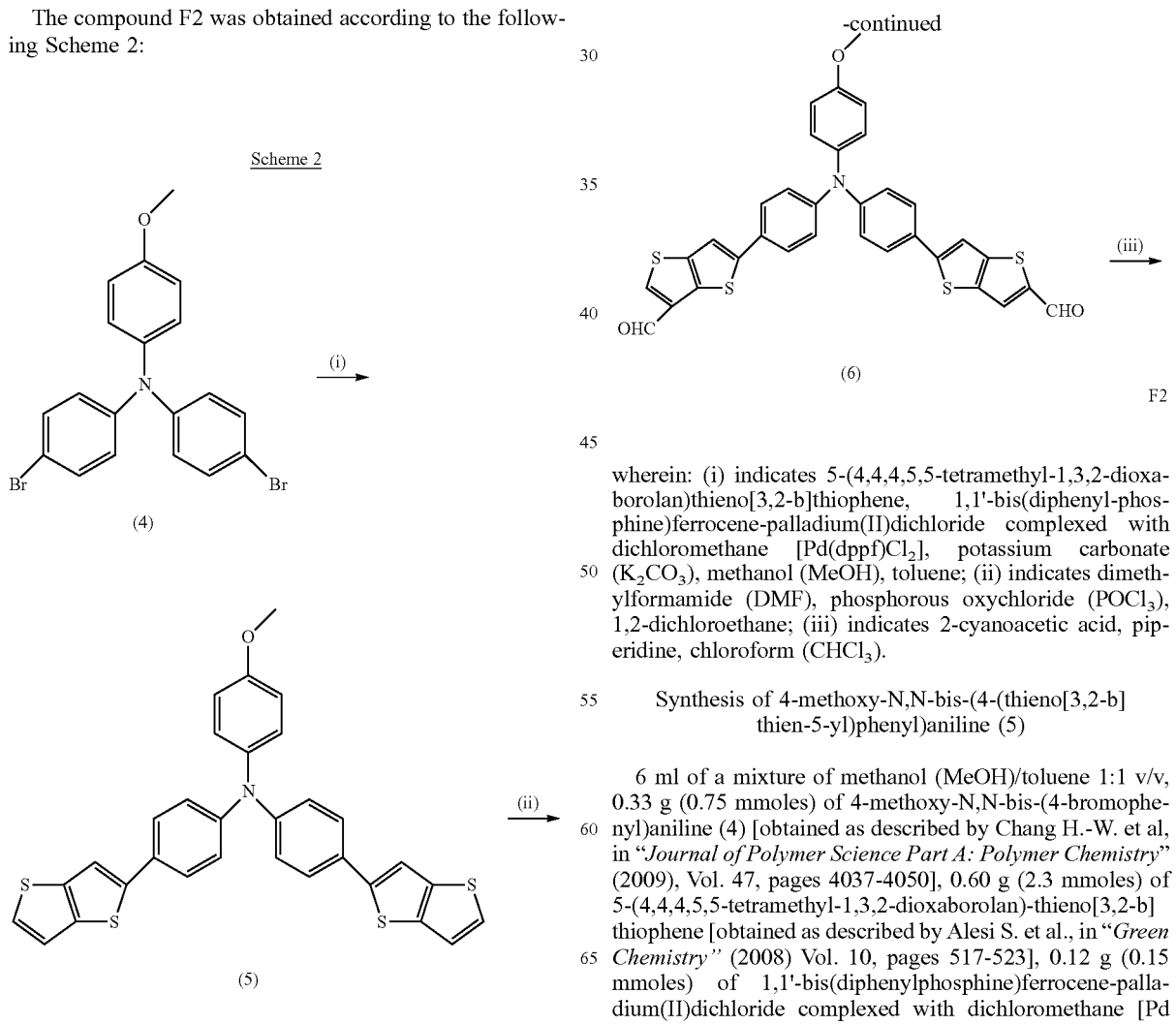

wherein: (i) indicates 5-(4,4,4,5,5-tetramethyl-1,3,2-dioxaborolan)thieno[3,2-b]thiophene, 1,1'-bis(diphenyl-phosphine)ferrocene-palladium(II)dichloride complexed with dichloromethane [Pd(dppf)Cl$_2$], potassium carbonate (K$_2$CO$_3$), methanol (MeOH), toluene; (ii) indicates dimethylformamide (DMF), phosphorous oxychloride (POCl$_3$), 1,2-dichloroethane; (iii) indicates 2-cyanoacetic acid, piperidine, chloroform (CHCl$_3$).

Synthesis of 4-methoxy-N,N-bis-(4-(thieno[3,2-b]thien-5-yl)phenyl)aniline (5)

6 ml of a mixture of methanol (MeOH)/toluene 1:1 v/v, 0.33 g (0.75 mmoles) of 4-methoxy-N,N-bis-(4-bromophenyl)aniline (4) [obtained as described by Chang H.-W. et al, in "*Journal of Polymer Science Part A: Polymer Chemistry*" (2009), Vol. 47, pages 4037-4050], 0.60 g (2.3 mmoles) of 5-(4,4,4,5,5-tetramethyl-1,3,2-dioxaborolan)-thieno[3,2-b]thiophene [obtained as described by Alesi S. et al., in "*Green Chemistry*" (2008) Vol. 10, pages 517-523], 0.12 g (0.15 mmoles) of 1,1'-bis(diphenylphosphine)ferrocene-palladium(II)dichloride complexed with dichloromethane [Pd (dppf)Cl₂] and 1.06 g (8.3 mmoles) of potassium carbonate (K₂CO₃), were introduced into a 50 ml microwave test-tube. The test-tube was then sealed and heated with microwaves to 70° C., 50 W, for 20 minutes. 20 ml of dichloromethane (CH₂Cl₂) were then added and the whole mixture was poured into 50 ml of a saturated aqueous solution of ammonium chloride (NH₄Cl) and extracted with dichloromethane (CH₂Cl₂) (3×20 ml). The organic phase obtained was washed with water (2×15 ml) and dried on sodium sulfate (Na₂SO₄). After eliminating the solvent by evaporation at reduced pressure, a crude oil was obtained, which was purified by means of flash chromatography on silica gel, using as eluent a mixture of n-hexane/dichloromethane (CH₂Cl₂) (1:1, v/v), obtaining 0.36 g (yield 87%) of 4-methoxy-N,N-bis-(4-(thieno[3,2-b]thien-5-yl)phenyl)aniline (5), as a yellow solid, having a melting point of 140° C.-141° C.

Said 4-methoxy-N,N-bis-(4-(thieno[3,2-b]thien-5-yl)phenyl)aniline (5) was characterized by means of ¹H-NMR (500 MHz; CDCl₃; Me₄Si) obtaining the following spectrum: $\delta_H$ 7.77 (2 H, s), 7.65 (2 H, d, J 5.3), 7.61 (4 H, d, J 8.7), 7.44 (2 H, d, J 5.1), 7.13 (2 H, d, J 8.9), 7.04 (4 H, d, J 8.7), 6.99 (2 H, d, J 8.9), 3.80 (3 H, s).

Synthesis of 4-methoxy-N,N-bis-(4-(5'-formyl-thieno-[3,2-b]thien-5-yl)phenyl)aniline (6)

0.11 g (1.4 mmoles) of dimethyl formamide (DMF) were introduced into a 50 ml flask, previously anhydrified and maintained under a flow of nitrogen (N₂), and subsequently, after cooling to a temperature of −10° C., 0.22 g (1.4 mmoles) of phosphorous oxychloride (POCl₃) were slowly added dropwise: the formation of a vitreous white solid was observed and after 30 minutes, 10 ml of 1,2-dichloroethane were added. After the complete dissolution of the reaction mixture, 0.36 g (0.65 mmoles) of 4-methoxy-N,N-bis-(4-(thieno[3,2-b]thien-5-yl)phenyl)aniline (5), obtained as described above, dissolved in 15 ml of 1,2-dichloroethane, were added. The reaction mixture was left, under stirring, at 70° C., for 4 hours. The reaction was then quenched by adding 20 ml of a saturated aqueous solution of sodium acetate (AcONa) and the whole mixture was left, under stirring, for 1 hour, and then extracted with dichloromethane (CH₂Cl₂) (3×15 ml). The organic phase obtained was washed with water (2×15 ml) and dried on sodium sulfate (Na₂SO₄). After eliminating the solvent by evaporation at reduced pressure, 0.13 g (yield 34%) of 4-methoxy-N,N-bis-(4-(5'-formyl-thieno-[3,2-b]thien-5-yl)phenyl)aniline (6) were obtained, as a dark orange solid, having a melting point of 225° C.-226° C.

Said 4-methoxy-N,N-bis-(4-(5'-formyl-thieno-[3,2-b]thien-5-yl)phenyl)aniline (6) was characterized by means of ¹H-NMR (500 MHz; CDCl₃; Me₄Si) obtaining the following spectrum: $\delta_H$ 9.96 (2 H, s), 8.40 (2 H, s), 7.92 (2 H, s), 7.70 (4 H, d, J 8.5), 7.15 (2 H, d, J 8.6), 7.10 (4 H, d, J 8.5), 7.02 (2 H, d, J 8.6), 3.80 (3 H, s).

Synthesis of the Compound F2

0.13 g (0.22 mmoles) of 4-methoxy-N,N-bis-(4-(thieno[3,2-b]thien-5-yl)phenyl)aniline (5), obtained as described above, and 10 ml of chloroform (CHCl₃) were introduced into a 50 ml flask: 0.19 g (2.2 mmoles) of 2-cyanoacetic acid were then added to the solution obtained. The reaction mixture obtained was cooled to 0° C. with an ice bath and a solution of piperidine (0.21 g, 2.5 mmoles) in 5 ml of chloroform (CHCl₃) was subsequently slowly added dropwise. At the end of the dripping, the reaction mixture was heated to the reflux temperature of the solvent, for 8 hours. The reaction mixture was then left to cool to room temperature (25° C.) and the solvent was eliminated by evaporation at reduced pressure, obtaining a dark orange crude oil. The crude oil obtained was subsequently dissolved in 10 ml of water and treated with 5 ml of an aqueous solution of hydrochloric acid at 10%: in this phase, the formation of a dark precipitate was observed, which was recovered by filtration at reduced pressure, washed with water (2×15 ml) and dried under vacuum obtaining 0.07 g (yield 41%) of the compound (F2) as a purple solid having a melting point >250° C.

Said compound (F2) was characterized by means of ¹H-NMR (500 MHz; DMSO-d₆; Me₄Si) obtaining the following spectrum: $\delta_H$ 8.56 (2H, s), 8.31 (2H, s), 7.95 (2 H, 5), 7.69 (4 H, d, J 8.6), 7.16 (2 H, d, J 8.8), 7.09 (4 H, d, J 8.7), 7.01 (2 H, d, J 8.8), 3.80 (3H, s).

Example 3

Preparation of the Compound (F3)

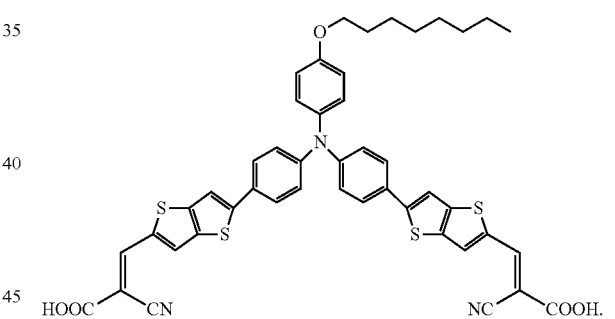

(F3)

The compound (F3) was obtained according to the following Scheme 3:

Scheme 3

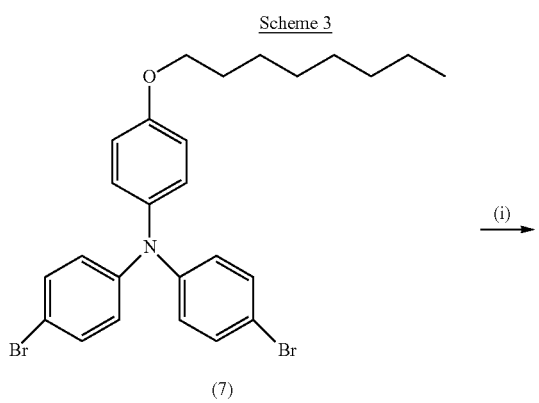

(7)

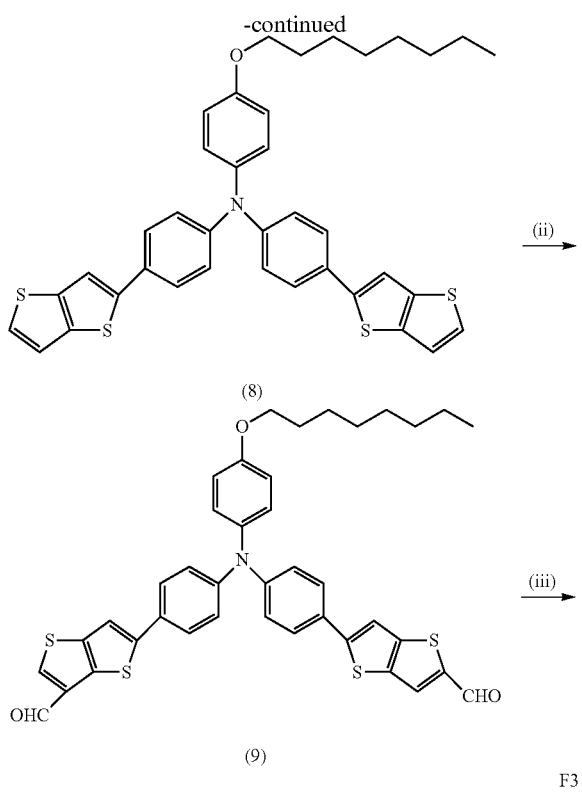

wherein: (i) indicates 5-(4,4,4,5,5-tetramethyl-1,3,2-dioxaborolan)thieno[3,2-b]thiophene, 1,1'-bis(diphenyl-phosphine)ferrocene-palladium(II)dichloride complexed with dichloromethane [Pd(dppf)Cl$_2$], potassium carbonate (K$_2$CO$_3$), methanol (MeOH), toluene; (ii) indicates dimethylformamide (DMF), phosphorous oxychloride (POCl$_3$); (iii) indicates 2-cyanoacetic acid, piperidine, chloroform (CHCl$_3$).

Synthesis of 4-octyloxy-N,N-bis-(4-(thieno[3,2-b]thien-5-yl)phenyl)aniline (8)

12 ml of a mixture of methanol (MeOH)/toluene 1:1 v/v, 0.70 g (1.3 mmoles) of 4-octyloxy-N,N-bis-(4-bromophenyl)aniline (7) [obtained as described by Blankenburg L. et al., "Journal of Applied Polymer Science" (2009), Vol. 111, pages 1850-1861], 1.05 g (3.9 mmoles) of 5-(4,4,4,5,5-tetramethyl-1,3,2-dioxaborolan)thieno[3,2-b]thiophene [obtained as described by Alesi S. et al., in "Green Chemistry" (2008) Vol. 10, pages 517-523], 0.22 g (0.27 mmoles) of 1,1'-bis(diphenylphosphine)ferrocene-palladium(II)dichloride complexed with dichloromethane [Pd(dppf)Cl$_2$] and 1.86 g (14.5 mmoles) of potassium carbonate (K$_2$CO$_3$), were introduced into a 50 ml microwave test-tube. The test-tube was then sealed and heated with microwaves to 70° C., 50 W, for 10 minutes. 20 ml of dichloromethane (CH$_2$Cl$_2$) were then added and the whole mixture was poured into 50 ml of a saturated aqueous solution of ammonium chloride (NH$_4$Cl) and extracted with dichloromethane (CH$_2$Cl$_2$) (3×20 ml). The organic phase obtained was washed with water (2×15 ml) and dried on sodium sulfate (Na$_2$SO$_4$). After eliminating the solvent by evaporation at reduced pressure, a crude oil was obtained, which was purified by means of flash chromatography on silica gel, using as eluent a mixture of n-hexane/diethyl ether (Et$_2$O) (8:2, v/v), obtaining 0.71 g (yield 92%) of 4-octyloxy-N,N-bis-(4-(thieno[3,2-b]thien-5-yl)phenyl)aniline (8), as a yellow solid.

Said 4-octyloxy-N,N-bis-(4-(thieno[3,2-b]thien-5-yl)phenyl)aniline (8) was characterized by means of $^1$H-NMR (500 MHz; CDCl$_3$; Me$_4$Si) obtaining the following spectrum: $\delta_H$ 7.77 (2 H, s), 7.65 (2 H, d, J 5.3), 7.61 (4 H, d, J 8.7), 7.44 (2 H, d, J 5.1), 7.13 (2 H, d, J 8.9), 7.04 (4 H, d, J 8.7), 6.99 (2 H, d, J 8.9), 3.98 (2 H, t, J 6.4), 1.73 (2 H, quintet, J 7.0), 1.66 (2 H, quintet, J 7.1), 1.37-1.22 (8 H, m), 0.88 (3 H, t, J 6.7).

Synthesis of 4-octyloxy-N,N-bis-(4-(5'-formyl-thieno-[3,2-b]thien-5-yl)phenyl)aniline (9)

0.28 g (3.9 mmoles) of dimethyl formamide (DMF) were introduced into a 100 ml flask, previously anhydrified and maintained under a flow of nitrogen (N$_2$), and subsequently, after cooling to a temperature of −10° C., 0.59 g (3.9 mmoles) of phosphorous oxychloride (POCl$_3$) were slowly added dropwise: the formation of a vitreous white solid was observed and after 30 minutes, 10 ml of dimethylformamide (DMF) were added. After the complete dissolution of the reaction mixture, 0.71 g (1.3 mmoles) of 4-octyloxy-N,N-bis-(4-(thieno[3,2-b]thien-5-yl)phenyl)aniline (8), obtained as described above, dissolved in 25 ml of dimethylformamide, were added. The reaction mixture was left, under stirring, at 70° C., for 4 hours. The reaction was then quenched by adding 40 ml of a saturated aqueous solution of sodium acetate (AcONa) and the whole mixture was left, under stirring, for 1 hour and then extracted with dichloromethane (CH$_2$Cl$_2$) (3×15 ml). The organic phase obtained was washed with water (2×15 ml) and dried on sodium sulfate (Na$_2$SO$_4$). After eliminating the solvent by evaporation at reduced pressure, a crude oil was obtained, which was purified by means of flash chromatography on silica gel using as eluent, a mixture of n-hexane/diethyl ether (Et$_2$O) (8:2, v/v), obtaining 0.20 g (yield 22%) of 4-octyloxy-N,N-bis-(4-(5'-formyl-thieno-[3,2-b]thien-5-yl)phenyl)-aniline (9), as a dark orange oil.

Said 4-octyloxy-N,N-bis-(4-(5'-formyl-thieno-[3,2-b]thien-5-yl)phenyl)aniline (9) was characterized by means of $^1$H-NMR (500 MHz; CDCl$_3$; Me$_4$Si) obtaining the following spectrum: $\delta_H$ 9.87 (2 H, s), 8.39 (2 H, s), 7.92 (2 H, s), 7.69 (4 H, d, J 8.6), 7.14 (2 H, d, J 8.8), 7.08 (4 H, d, J 8.6), 7.00 (2 H, d, J 8.8), 3.98 (2 H, t, J 6.4), 1.73 (2 H, quintet, J 7.0), 1.66 (2 H, quintet, J 7.1), 1.37-1.22 (8 H, m), 0.88 (3 H, t, J 6.7).

Synthesis of the Compound F3

0.20 g (0.28 mmoles) of 4-octyloxy-N,N-bis-(4-(5'-formyl-thieno-[3,2-b]thien-5-yl)phenyl)aniline (9), obtained as described above, and 10 ml of chloroform (CHCl$_3$), were introduced into a 50 ml flask: 0.24 g (2.8 mmoles) of 2-cyanoacetic acid were then added to the solution obtained. The reaction mixture obtained was cooled to 0° C. with an ice bath and a solution of piperidine (0.25 g, 3.0 mmoles) in 5 ml of chloroform (CHCl$_3$) was subsequently slowly added dropwise. At the end of the dripping, the reaction mixture was heated to the reflux temperature of the solvent, for 16 hours. The reaction mixture was then left to cool to room temperature (25° C.) and the solvent was eliminated by evaporation at reduced pressure, obtaining a dark orange crude oil. The crude oil obtained was subsequently dissolved in 10 ml of water and treated with 5 ml of an aqueous solution of hydrochloric acid at 10%: in this phase, the formation of a dark precipitate was observed, which was recovered by filtration at reduced pressure, washed with water (2×15 ml) and dried under vacuum obtaining 0.17 g (yield 71%) of the compound (F3) as a purple solid having a melting point >250° C.

Said compound (F3) was characterized by means of $^1$H-NMR (500 MHz; DMSO-$d_6$; Me$_4$Si) obtaining the following spectrum: $\delta_H$ 8.57 (2H, s), 8.32 (2H, s), 7.95 (2 H, s), 7.69 (4 H, d, J 8.7), 7.14 (2 H, d, J 8.8), 7.08 (4 H, d, J 8.7), 6.99 (2 H, d, J 8.9), 3.98 (2 H, t, J 6.4), 1.73 (2 H, quintet, J 7.0), 1.66 (2 H, quintet, J 7.1), 1.37-1.22 (8 H, m), 0.88 (3 H, t, J 6.7).
Example 4
Preparation of the Compound (F4)
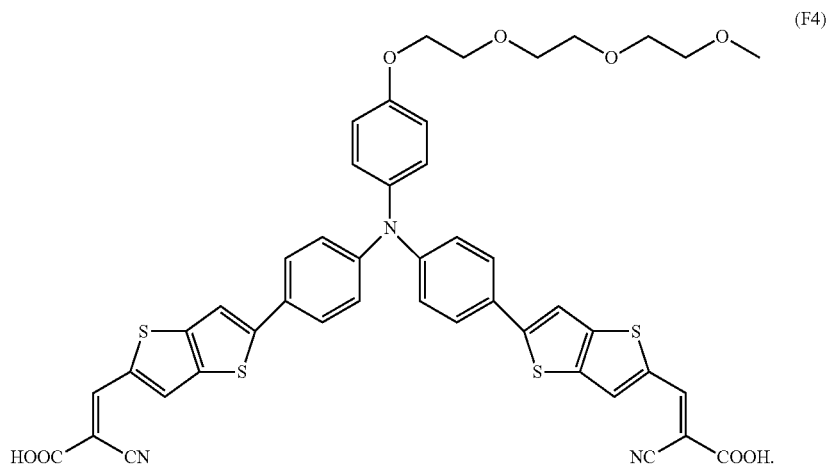 [SMILES: COCCOCCOCCOc1ccc(N(c2ccc(-c3cc4sc(/C=C(\C#N)C(=O)O)cc4s3)cc2)c2ccc(-c3cc4sc(/C=C(\C#N)C(=O)O)cc4s3)cc2)cc1]
The compound (F4) was obtained according to the following Scheme 4:
Scheme 4
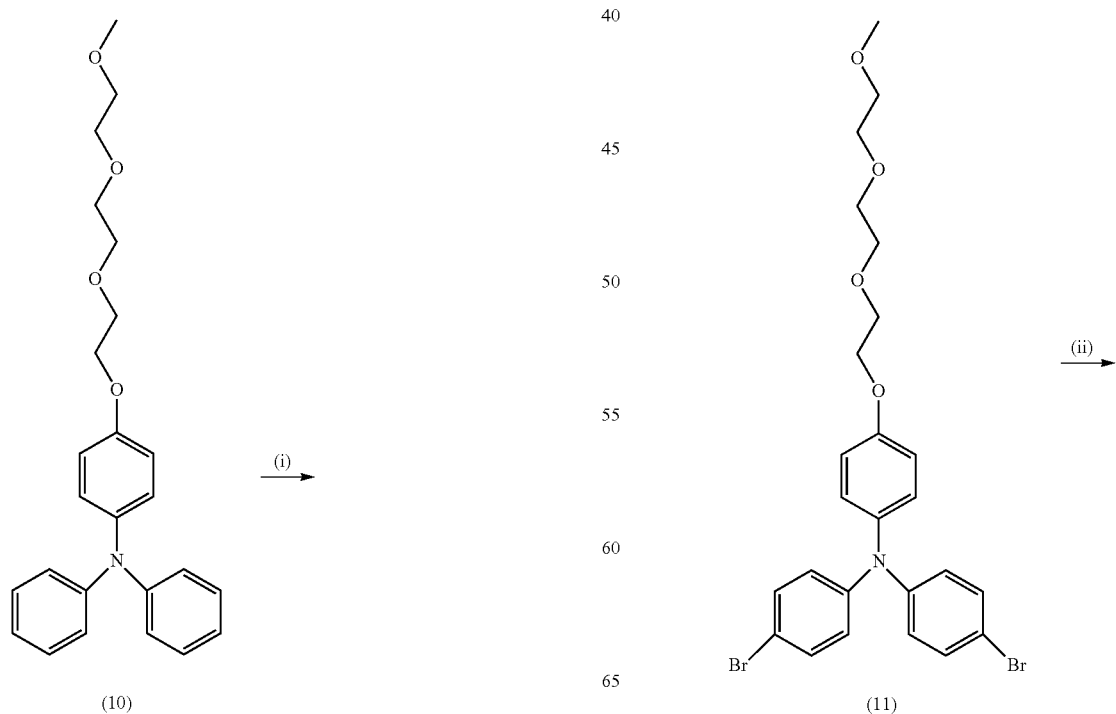

-continued

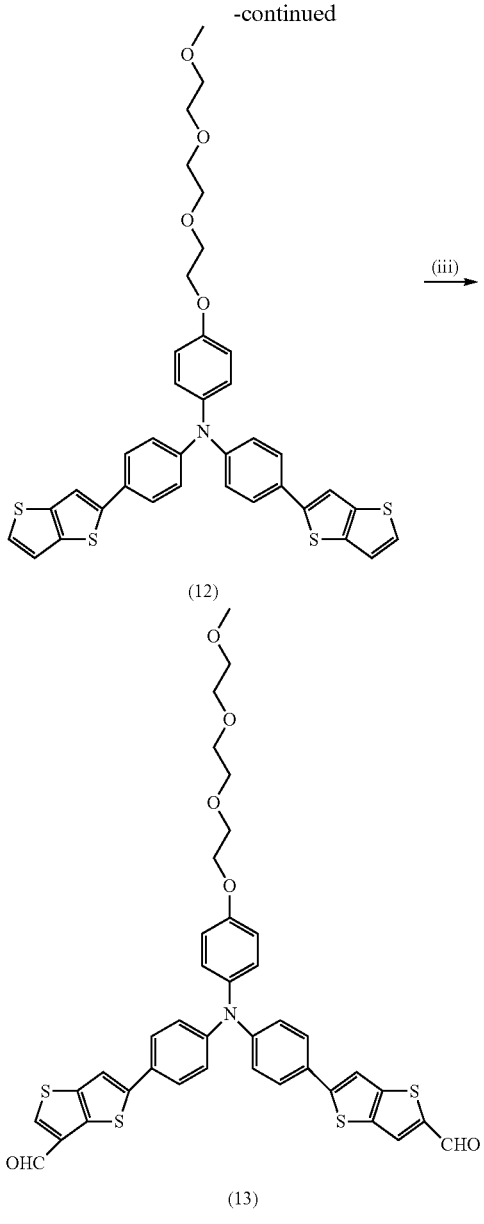

wherein: (i) indicates N-bromosuccinimide (NBS), dimethylformamide (DMF); (ii) indicates 5-(4,4,4,5,5-tetramethyl-1,3,2-dioxaborolan)thieno[3,2-b]thiophene, 1,1'-bis(diphenyl-phosphine)ferrocene-palladium(II)-dichloride complexed with dichloromethane [Pd(dppf)Cl$_2$], potassium carbonate (K$_2$CO$_3$), methanol (MeOH), toluene; (iii) indicates dimethylformamide (DMF), phosphorous oxychloride (POCl$_3$); (iv) indicates 2-cyanoacetic acid, piperidine, chloroform (CHCl$_3$).

Synthesis of 4-(1-{2-[2-(2-methoxyethoxy)ethoxy]-ethoxy})-N,N-bis-(4-bromophenyl)aniline (11)

0.38 g (0.93 mmoles) of 4-(1-{2-[2-(2-methoxy-ethoxy)ethoxy]})-N,N-bis-(phenyl)aniline (10), [obtained as described by Willinger K. et al., in "*Journal of Materials Chemistry*" (2009), Vol. 19, pages 5364-5376], and 10 ml of dimethylformamide (DMF), were introduced into a 50 ml flask, and a solution of N-bromosuccinimide (NBS) (0.33 g, 1.9 mmoles) in 5 ml of dimethylformamide (DMF) was then slowly added dropwise, after cooling the solution to 0° C. with an ice bath. At the end of the dripping, the reaction mixture was heated to room temperature (25° C.) and kept, under stirring, for 16 hours. The reaction mixture was then poured into a 250 ml flask containing 75 ml of water and 20 ml of diethyl ether (Et$_2$O) and was extracted with diethyl ether (Et$_2$O) (3×15 ml). The organic phase obtained was dried on sodium sulfate (Na$_2$SO$_4$) and the solvent was eliminated by evaporation at reduced pressure, obtaining 0.37 g (yield 71%) of 4-(1-{2-[2-(2-methoxyethoxy)ethoxy]ethoxy})-N,N-bis-(4-bromophenyl)aniline (11) as a brown oil.

Said 4-(1-{2-[2-(2-methoxyethoxy)ethoxy]ethoxy})-N,N-bis-(4-bromophenyl)aniline (11) was characterized by means of $^1$H-NMR (500 MHz; CDCl$_3$; Me$_4$Si) obtaining the following spectrum: $\delta_H$ 7.29 (4 H, d, J 8.8), 7.00 (2 H, d, J 8.9), 6.87 (4 H, d, J 8.8), 6.85 (2 H, d, J 8.9), 4.11 (2 H, t, J 5.1), 3.85 (2 H, t, J 4.7), 3.78-3.74 (2 H, m), 3.72-3.66 (4 H, m), 3.58-3.54 (2 H, s), 3.37 (3 H, s)

Synthesis of 4-(1-{2-[2-(2-methoxyethoxy)ethoxy]-ethoxy})-N,N-bis-(4-(thieno[3,2-b]thien-5-yl)phenyl)-aniline (12)

12 ml of a mixture of methanol (MeOH)/toluene (1:1 v/v), 0.37 g (0.66 mmoles) of 4-(1-{2-[2-(2-methoxyethoxy)ethoxy]ethoxy})-N,N-bis-(4-bromophenyl)-aniline (11) [obtained as described above], 0.53 g (0.66 mmoles) of 5-(4,4,4,5,5-tetramethyl-1,3,2-dioxaborolan)-thieno[3,2-b]thiophene [obtained as described by Alesi S. et al., in "*Green Chemistry*" (2008), Vol. 10, pages 517-523], 0.05 g (0.06 mmoles) of 1,1'-bis(diphenylphosphine)ferrocene-palladium(II)dichloride complexed with dichloromethane [Pd(dppf)Cl$_2$] and 1.0 g (7.3 mmoles) of potassium carbonate (K$_2$CO$_3$), were introduced into a 50 ml microwave test-tube. The test-tube was then sealed and heated with microwaves to 70° C., 50 W, for 20 minutes. 20 ml of ethyl acetate (AcOEt) were then added and the whole mixture was poured into a 100 ml flask containing 40 ml of a saturated aqueous solution of ammonium chloride (NH$_4$Cl) and subsequently extracted with ethyl acetate (AcOEt) (3×20 ml). The organic phase obtained was dried on sodium sulfate (Na$_2$SO$_4$) and the solvent was eliminated by evaporation at reduced pressure. A crude oil was obtained, which was purified by means of flash chromatography on silica gel, using as eluent a mixture of diethyl ether (Et$_2$O)/ethyl acetate (AcOEt) (8:2, v/v), obtaining 0.32 g (yield 71%) of 4-(1-{2-[2-(2-methoxyethoxy)ethoxy]ethoxy})-N,N-bis-(4-(thieno[3,2-b]thien-5-yl)phenyl)aniline (12), as a yellow solid.

Said 4-(1-{2-[2-(2-methoxyethoxy)ethoxy]ethoxy})-N,N-bis-(4-(thieno[3,2-b]thien-5-yl)phenyl)aniline (12) was characterized by means of $^1$H-NMR (500 MHz; CDCl$_3$; Me$_4$Si) obtaining the following spectrum: $\delta_H$ 7.48 (4 H, d, J 8.7), 7.39 (2 H, s), 7.32 (2 H, d, J 5.2), 7.23 (2 H, d, J 5.2), 7.12 (2 H, d, J 8.9), 7.08 (4 H, d, J 8.7), 6.90 (2 H, d, J 8.9), 4.14 (2 H, t, J 4.7), 3.87 (2 H, t, J 4.7), 3.78-3.74 (2 H, m), 3.70-3.63 (4 H, m), 3.58-3.54 (2 H, s), 3.39 (3 H, s).

Synthesis of 4-(1-{2-[2-(2-methoxyethoxy)ethoxy]-ethoxy})-N,N-bis-(4-(5'-formyl-thieno[3,2-b]thien-5-yl)phenyl)aniline (13)

0.08 g (1.1 mmoles) of dimethyl formamide (DMF) were introduced into a 100 ml flask, previously anhydrified and maintained under a flow of nitrogen (N$_2$), and subsequently, after cooling to a temperature of −10° C., 0.17 g (1.1 mmoles) of phosphorous oxychloride (POCl$_3$) were slowly added dropwise: the formation of a vitreous white solid was observed and after 30 minutes, 5 ml of dimethylformamide (DMF) were added. After the complete dissolution of the reaction mixture, 0.32 g (0.47 mmoles) of 4-(1-{2-[2-(2-methoxyethoxy)ethoxy]ethoxy})-N,N-bis-(4-(thieno[3,2-b]thien-5-yl)phenyl)aniline (12), obtained as described above, dissolved in 20 ml of dimethylformamide, were added. The reaction mixture was left, under stirring, at 70° C., for 4 hours. The reaction was then quenched in a saturated aqueous solution of sodium acetate (AcONa) and the whole mixture was left, under stirring, for 1 hour and then extracted with dichloromethane (CH$_2$Cl$_2$) (3×30 ml). The organic phase obtained was washed with water (2×20 ml) and dried on sodium sulfate (Na$_2$SO$_4$). After eliminating the solvent by evaporation at reduced pressure, a crude oil was obtained, which was purified by means of flash chromatography on silica gel using as eluent, a mixture of diethyl ether (Et$_2$O)/dichloromethane (CH$_2$Cl$_2$) (2:1 v/v), obtaining 0.17 g (yield 49%) of 4-(1-{2-[2-(2-methoxyethoxy)ethoxy]-ethoxy})-N,N-bis-(4-(5'-formyl-thieno[3,2-b]thien-5-yl)phenyl)aniline (13), as a dark orange solid.

Said 4-(1-{2-[2-(2-methoxyethoxy)ethoxy]ethoxy})-N,N-bis-(4-(5'-formyl-thieno[3,2-b]thien-5-yl)phenyl)-aniline (13) was characterized by means of $^1$H-NMR (500 MHz; DMSO-d$_6$; Me$_4$Si) obtaining the following spectrum: δ$_H$ 9.96 (2 H, s), 8.38 (2 H, s), 7.90 (2 H, s), 7.67 (2 H, d, J 8.7), 7.13 (4 H, d, J 8.9), 7.07 (2 H, d, J 8.7), 7.02 (4 H, d, J 8.9), 4.12 (2 H, t, J 4.7), 3.76 (2 H, t, J 4.5), 3.62-3.58 (2 H, m), 3.57-3.50 (4 H, m), 3.46-3.42 (2 H, s), 3.25 (3 H, s).

Synthesis of the compound (F4)

0.17 g (0.23 mmoles) of 4-(1-{2-[2-(2-methoxyethoxy)ethoxy]ethoxy})-N,N-bis-(4-(5'-formyl-thieno[3,2-b]thien-5-yl)phenyl)aniline (13), obtained as described above, and 10 ml of chloroform (CHCl$_3$) were introduced into a 50 ml flask: 0.19 g (2.3 mmoles) of 2-cyanoacetic acid were then added to the solution obtained. The reaction mixture was cooled to 0° C. with an ice bath and a solution of piperidine (0.22 g, 2.6 mmoles) in 5 ml of chloroform (CHCl$_3$) was subsequently slowly added dropwise. At the end of the dripping, the reaction mixture was heated to the reflux temperature of the solvent, for 10 hours. The reaction mixture was then left to cool to room temperature (25° C.) and the solvent was eliminated by evaporation at reduced pressure, obtaining a dark orange crude oil which was dissolved in 50 ml of water and treated with 20 ml of an aqueous solution of hydrochloric acid at 10%: in this phase, the formation of a dark precipitate was observed, which was recovered by filtration at reduced pressure, washed with water (2×15 ml) and dried under vacuum obtaining 0.12 g (yield 61%) of the compound (F4) as a purple solid, having a melting point >250° C.

Said compound (F4) was characterized by means of $^1$H-NMR (500 MHz; DMSO-d$_6$; Me$_4$Si) obtaining the following spectrum: δ$_H$ 8.50 (2 H, s), 8.27 (2 H, s), 7.93 (2 H, s), 7.67 (4 H, d, J 8.7), 7.14 (2 H, d, J 9.0), 7.08 (4 H, d, J 8.7), 7.02 (2 H, d, J 9.0), 4.12 (2 H, t, J 4.7), 3.76 (2 H, t, J 4.5), 3.62-3.58 (2 H, m), 3.56-3.50 (4 H, m), 3.46-3.42 (2 H, s), 3.25 (3 H, s).

Said compound (F4) was also characterized by means of $^{13}$C-NMR (125,77 MHz; DMSO-d$_6$; Me$_4$Si) obtaining the following spectrum: δ$_C$ 164.16, 156.67, 152.22, 148.09, 147.50, 147.09, 139.04, 137.81, 137.23, 132.26, 128.58, 127.56, 123.01, 117.43, 116.43, 116.24, 71.78, 70.44, 70.31, 70.11, 69.43, 67.91, 58.55.

Example 5

Preparation of the Compound (F5)

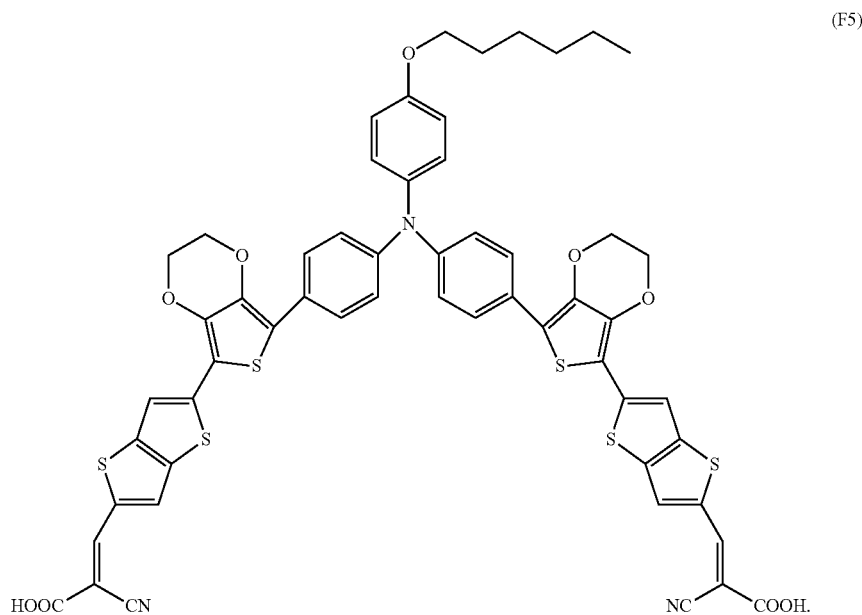 [SMILES: CCCCCCOc1ccc(N(c2ccc(-c3sc(-c4cc5sc(/C=C(\C#N)C(=O)O)cc5s4)c4c3OCCO4)cc2)c2ccc(-c3sc(-c4cc5sc(/C=C(\C#N)C(=O)O)cc5s4)c4c3OCCO4)cc2)cc1]

(F5)

The compound (F5) was prepared according to the following Scheme 5:

Scheme 5
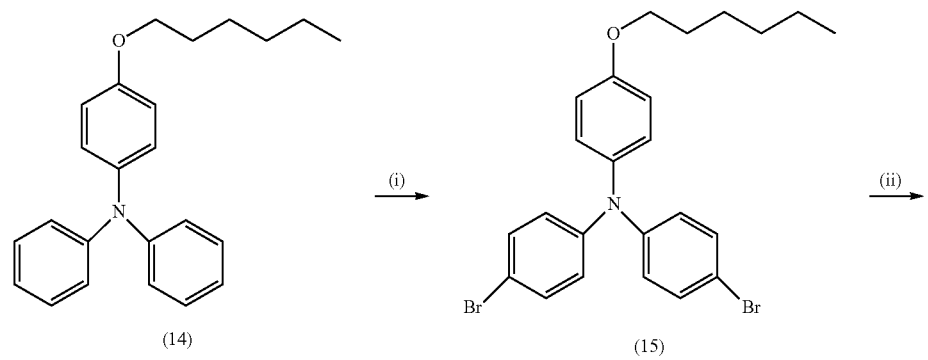
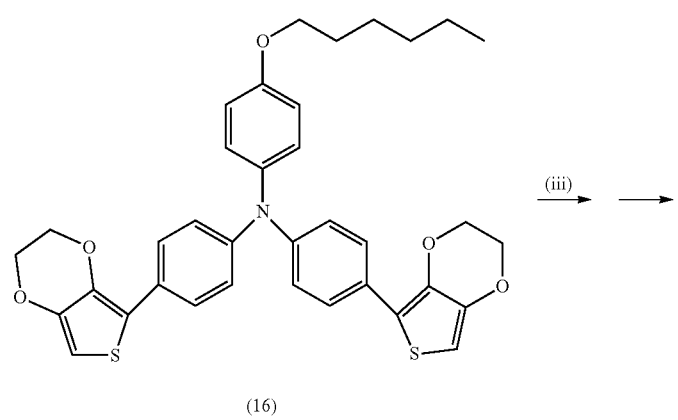
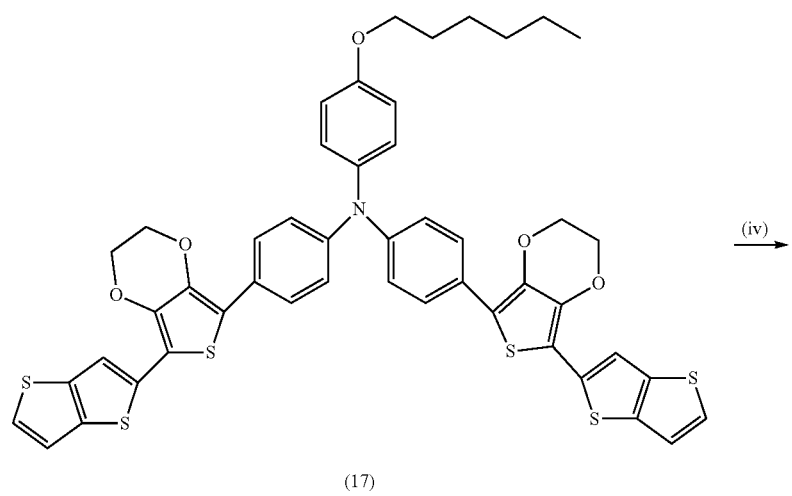

-continued

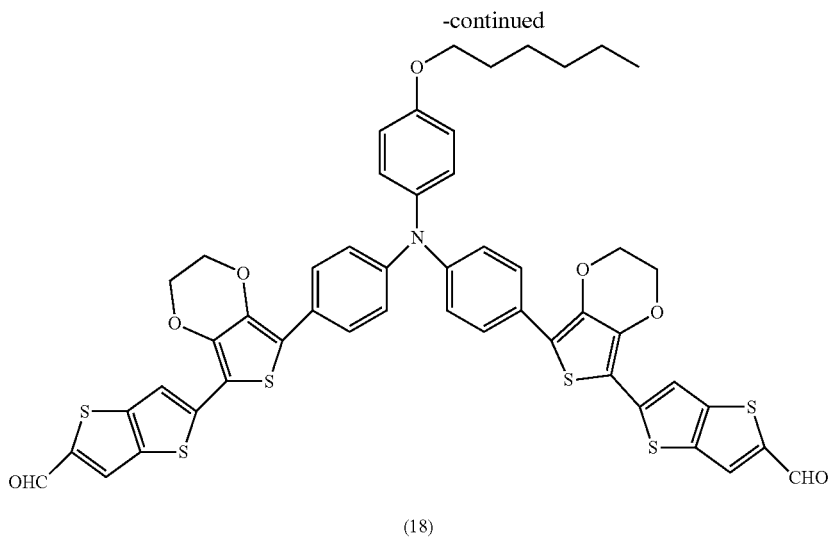

(18)

wherein: (i) indicates N-bromosuccinimide (NBS), dimethylformamide (DMF); (ii) indicates 5-(4,4,4,5,5-tetramethyl-1,3,2-dioxaborolan-2-yl)-2,3-dihydro-thieno[3,4-b][1,4]dioxin, 1,1'-bis(diphenylphosphine)-ferrocene-palladium(II)-dichloride complexed with dichloromethane [Pd(dppf)Cl$_2$], potassium carbonate (K$_2$CO$_3$), methanol (MeOH), toluene; (iii) indicates N-bromosuccinimide (NBS), dimethylformamide (DMF), 5-(4,4,4,5,5-tetramethyl-1,3,2-dioxaborolan)thieno[3,2-b]thiophene, 1,1'-bis(diphenylphosphine)ferrocene-palladium(II)dichloride complexed with dichloromethane [Pd(dppf)Cl$_2$], potassium carbonate (K$_2$CO$_3$), methanol (MeOH), toluene; (iv) indicates dimethylformamide (DMF), phosphorous oxychloride (POCl$_3$); (v) indicates 2-cyanoacetic acid, piperidine, chloroform (CHCl$_3$).

Synthesis of 4-hexyloxy-N,N-bis-(4-bromophenyl)aniline (15)

0.83 g (2.4 mmoles) of 4-hexyloxy-N,N-bis-(phenyl)aniline (14), [obtained as described by Li Z. A. et al., in "*Journal of Polymer Science Part A: Polymer Chemistry*" (2011), Vol. 49, pages 1977-1987], and 10 ml of dimethylformamide (DMF) (10 ml), were introduced into a 50 ml flask. The solution obtained was cooled to 0° C. with an ice bath and a solution of N-bromosuccinimide (NBS) (0.434 g, 2.4 mmoles) in 5 ml of dimethylformamide (DMF) was then slowly added dropwise. At the end of the dripping, the reaction mixture was heated to room temperature (25° C.) and left, under stirring, for 16 hours. The reaction mixture was then poured into a 250 ml flask containing 75 ml of water and 20 ml of diethyl ether (Et$_2$O) and extracted with diethyl ether (Et$_2$O) (3×15 ml). The organic phase obtained was dried on sodium sulfate (Na$_2$SO$_4$) and the solvent was eliminated by evaporation at reduced pressure, obtaining 1.10 g (yield 92%) of 4-hexyloxy-N,N-bis-(4-bromophenyl)aniline (15), as a colourless oil.

Said 4-hexyloxy-N,N-bis-(4-bromophenyl)aniline (15) was characterized by means of $^1$H-NMR (500 MHz; CDCl$_3$; Me$_4$Si) obtaining the following spectrum: $\delta_H$ 7.30 (4 H, d, J 8.8), 7.01 (2 H, d, J 8.9), 6.89 (4 H, d, J 8.9), 6.84 (2 H, d, J 8.9), 3.94 (2 H, t, J 6.5), 1.82-1.74 (2 H, m), 1.50-1.42 (2 H, m), 1.38-1.32 (4 H, m), 0.91 (3 H, t, J 7.1).

Synthesis of 4-hexyloxy-N,N-bis-(4-(3,4-ethylenedioxy-thien-5-yl)aniline (16)

30 ml of a mixture of methanol (MeOH)/toluene (1:1 v/v), 1.10 g (2.2 mmoles) of 4-hexyloxy-N,N-bis-(4-bromophenyl)aniline (15) [obtained as described above], 2.30 g (8.7 mmoles) of 5-(4,4,5,5-tetramethyl-1,3,2-dioxaborolan-2-yl)-2,3-dihydrothieno-[3,4-b][1,4]dioxin [obtained as described by A. Zulauf A. et al., in "*European Journal of Organic Chemistry*" (2008), Vol. 2008, pages 2118-2129], 0.13 g (0.11 mmoles) of 1,1'-bis(diphenylphosphine)ferrocene-palladium(II)dichloride complexed with dichloromethane [Pd(dppf)Cl$_2$] and 2.70 g (22 mmoles) of potassium carbonate (K$_2$CO$_3$), were introduced into a 100 ml microwave test-tube, previously anhydrified and maintained under a flow of nitrogen (N$_2$). The test-tube was then sealed and heated with microwaves to 70° C., 50 W, for 20 minutes. 50 ml of ethyl acetate (AcOEt) were then added and the whole mixture was poured into a 250 ml flask containing 100 ml of a saturated aqueous solution of ammonium chloride (NH$_4$Cl) and subsequently extracted with ethyl acetate (AcOEt) (3×30 ml). The organic phase obtained was dried on sodium sulfate (Na$_2$SO$_4$) and the solvent was eliminated by evaporation at reduced pressure. A crude oil was obtained, which was purified by means of flash chromatography on silica gel, using as eluent a mixture of dichloromethane (CH$_2$Cl$_2$)/ethyl phosphate (ETP) (6:4, v/v), obtaining 0.50 g (yield 36%) of 4-hexyloxy-N,N-bis-(4-(3,4-ethylenedioxythien-5-yl)aniline (16), as a yellow solid.

Said 4-hexyloxy-N,N-bis-(4-(3,4-ethylenedioxy-thien-5-yl)aniline (16) was characterized by means of $^1$H-NMR (500 MHz; CDCl$_3$; Me$_4$Si) obtaining the following spectrum: $\delta_H$ 7.54 (4 H, d, J 8.8), 7.07 (2 H, d, J 8.9), 7.03 (4 H, d, J 8.8), 6.83 (2 H, d, J 8.9), 6.24 (2 H, s), 4.31-4.27 (4 H, m), 4.26-4.22 (4 H, m), 3.94 (2 H, t, J 6.5), 1.82-1.74 (2 H, m), 1.50-1.42 (2 H, m), 1.38-1.32 (4 H, m), 0.91 (3 H, t, J 7.1).

Synthesis of 4-hexyloxy-N,N-bis-(4-((3,4-ethylene-dioxythien-5-yl)thieno[3,2-b]thien-5-yl)phenyl)aniline (17)

0.50 g (0.80 mmoles) of 4-hexyloxy-N,N-bis-(4-(3,4-ethylenedioxythien-5-yl)aniline (16) obtained as described above and 10 ml of dimethylformamide (DMF), were introduced into a 50 ml flask. The solution obtained was cooled to 0° C. with an ice bath and a solution of N-bromosuccinimide (NBS) (0.28 g, 1.6 mmoles) in 5 ml of dimethylformamide (DMF) was then slowly added dropwise. At the end of the dripping, the reaction mixture was heated to room temperature (25° C.) and left under stirring, for 30 minutes. The reaction mixture was then poured into 75 ml of water obtaining the precipitation of a yellow solid which was recovered by filtration at reduced pressure and immediately transferred into a 50 ml microwave test-tube, previously anhydrified and maintained under a flow of nitrogen (N$_2$) into which 20 ml of a mixture of methanol (MeOH)/toluene (1:1 v/v), 0.86 g (3.2 mmoles) of 5-(4,4,4,5,5-tetramethyl-1,3,2-dioxaborolane)-thieno[3,2-b]thiophene [obtained as described by Alesi S. et al., in "*Green Chemistry*" (2008), Vol. 10, pages 517-523], 0.092 g (0.08 mmoles) of 1,1'-bis(diphenyl-phosphine)ferrocene-palladium(II)-dichloride complexed with dichloromethane [Pd(dppf)Cl$_2$] and 1.10 g (8.0 mmoles) of potassium carbonate (K$_2$CO$_3$), were subsequently added. The test-tube was then sealed and heated with microwaves to 70° C., 50 W, for 20 minutes. 20 ml of dichloromethane (CH$_2$Cl$_2$) were then added and the whole mixture was poured into a 250 ml flask containing 100 ml of a saturated aqueous solution of ammonium chloride (NH$_4$Cl) and extracted with dichloromethane (CH$_2$Cl$_2$) (3×20 ml). The organic phase obtained was dried on sodium sulfate (Na$_2$SO$_4$) and the solvent was eliminated by evaporation at reduced pressure. A crude oil was obtained, which was purified by means of flash chromatography on silica gel, using as eluent a mixture of ethyl phosphate (ETP)/dichloromethane (CH$_2$Cl$_2$) (95:5, v/v), obtaining 0.135 g (yield 19%) of 4-hexyloxy-N,N-bis-(4-((3,4-ethylene-dioxythien-5-yl)thieno[3,2-b]thien-5-yl)-phenyl)aniline (17), as a yellow solid.

Said 4-hexyloxy-N,N-bis-(4-((3,4-ethylene-dioxy-thien-5-yl)thieno[3,2-b]thien-5-yl)-phenyl)aniline (17) was characterized by means of $^1$H-NMR (500 MHz; DMSO-d$_6$; Me$_4$Si) obtaining the following spectrum: $\delta_H$ 7.63 (2 H, d, J 5.2), 7.59 (4 H, d, J 8.8), 7.59 (2 H, s), 7.42 (2 H, d, J 5.2), 7.07 (2 H, d, J 8.9), 7.02 (4 H, d, J 8.8), 6.96 (2 H, d, J 8.9), 4.48-4.44 (4 H, m), 4.43-4.39 (4 H, m), 3.97 (2 H, t, J 6.4), 1.76-1.69 (2 H, m), 1.47-1.40 (2 H, m), 1.36-1.30 (4 H, m), 0.90 (3 H, t, J 7.1).

Synthesis of 4-hexyloxy-N,N-bis-(4-(5'-formyl-(3,4-ethylenedioxythien-5-yl)thieno[3,2-b]thien-5-yl)phenyl)aniline (18)

0.076 g (1.0 mmoles) of dimethyl formamide (DMF) were introduced into a 100 ml flask, previously anhydrified and maintained under a flow of nitrogen (N$_2$), and subsequently, after cooling to a temperature of −10° C., 0.15 g (1.0 mmole) of phosphorous oxychloride (POCl$_3$) were slowly added dropwise: the formation of a vitreous white solid was observed and after 30 minutes, 5 ml of dimethylformamide (DMF) were added. After the complete dissolution of the reaction mixture, 0.135 g (0.15 mmoles) of 4-hexyloxy-N,N-bis-(4-((3,4-ethylene-dioxy-thien-5-yl)thieno[3,2-b]thien-5-yl)-phenyl)aniline (17), obtained as described above, dissolved in 20 ml of dimethylformamide (DMF), were added. The reaction mixture was left under stirring, at 70° C., for 4 hours. The reaction was then quenched by adding 40 ml of a saturated aqueous solution of potassium carbonate (K$_2$CO$_3$) and the whole mixture was left, under stirring, for 1 hour and then extracted with ethyl acetate (AcOEt) (3×30 ml). The organic phase obtained was washed with water (2×20 ml) and dried on sodium sulfate (Na$_2$SO$_4$). After eliminating the solvent by evaporation at reduced pressure, a crude oil was obtained, which was purified by means of flash chromatography on silica gel using as eluent, a mixture of dichloromethane (CH$_2$Cl$_2$)/ethyl acetate (AcOEt) (95:5 v/v), obtaining 0.13 g (yield 87%) of 4-hexyloxy-N,N-bis-(4-(5'-formyl-(3,4-ethylenedioxythien-5-yl)thieno-[3,2-b]thien-5-yl)phenyl)aniline (18), as a dark orange solid.

Said 4-hexyloxy-N,N-bis-(4-(5'-formyl-(3,4-ethylenedioxythien-5-yl)thieno-[3,2-b]thien-5-yl)-phenyl)aniline (18) was characterized by means of $^1$H-NMR (500 MHz; DMSO-d$_6$; Me$_4$Si) obtaining the following spectrum: $\delta_H$ 9.94 (2 H, s), 8.34 (2 H, s), 7.69 (2 H, s), 7.62 (4 H, d, J 8.8), 7.08 (2 H, d, J 8.9), 7.03 (4 H, d, J 8.8), 6.96 (2 H, d, J 8.9), 4.53-4.48 (4 H, m), 4.45-4.41 (4 H, m), 3.97 (2 H, t, J 6.4), 1.76-1.69 (2 H, m), 1.47-1.40 (2 H, m), 1.36-1.30 (4 H, m), 0.90 (3 H, t, J 7.1).

Synthesis of the Compound (F5)

0.130 g (0.13 mmoles) of 4-hexyloxy-N,N-bis-(4-(5'-formyl-(3,4-ethylenedioxythien-5-yl)thieno-[3,2-b]-thien-5-yl)phenyl)aniline (18), obtained as described above, and 10 ml of chloroform (CHCl$_3$) were introduced into a 50 ml flask: 0.11 g (1.3 mmoles) of 2-cyanoacetic acid were then added to the solution obtained. The reaction mixture was cooled to 0° C. with an ice bath and a solution of piperidine (0.13 g, 1.5 mmoles) in 5 ml of chloroform (CHCl$_3$) was subsequently slowly added dropwise. At the end of the dripping, the reaction mixture was heated to the reflux temperature of the solvent, for 10 hours. The reaction mixture was then left to cool to room temperature (25° C.) and the solvent was eliminated by evaporation at reduced pressure, obtaining a dark orange crude oil which was dissolved in 50 ml of water and treated with 20 ml of an aqueous solution of hydrochloric acid at 10%: in this phase, the formation of a dark precipitate was observed, which was recovered by filtration at reduced pressure, washed with water (2×15 ml) and dried under vacuum obtaining 0.07 g (yield 46%) of the compound (F5) as a purple solid, having a melting point >250° C.

Said compound (F5) was characterized by means of $^1$H-NMR (500 MHz; DMSO-d$_6$; Me$_4$Si) obtaining the following spectrum: $\delta_H$ 8.19 (2 H, s), 8.02 (2 H, s), 7.68 (2 H, s), 7.62 (4 H, d, J 8.8), 7.08 (2 H, d, J 8.9), 7.03 (4 H, d, J 8.8), 6.97 (2 H, d, J 8.9), 4.53-4.47 (4 H, m), 4.45-4.39 (4 H, m), 3.97 (2 H, t, J 6.4), 1.76-1.69 (2 H, m), 1.47-1.40 (2 H, m), 1.36-1.30 (4 H, m), 0.90 (3 H, t, J 7.1).

Example 6

Preparation of the Compound F6

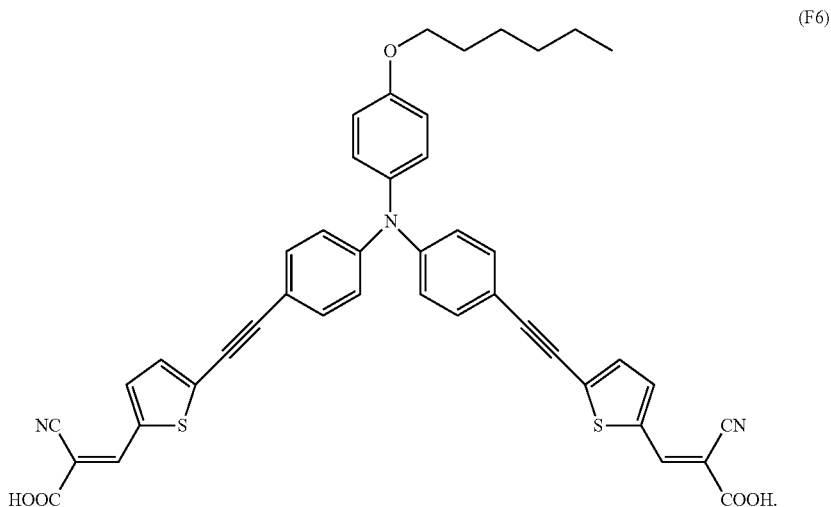 [SMILES: CCCCCCOc1ccc(N(c2ccc(C#Cc3ccc(/C=C(\C#N)C(=O)O)s3)cc2)c2ccc(C#Cc3ccc(/C=C(\C#N)C(=O)O)s3)cc2)cc1]

(F6)

The compound (F6) was synthesized according to the following Scheme 6:

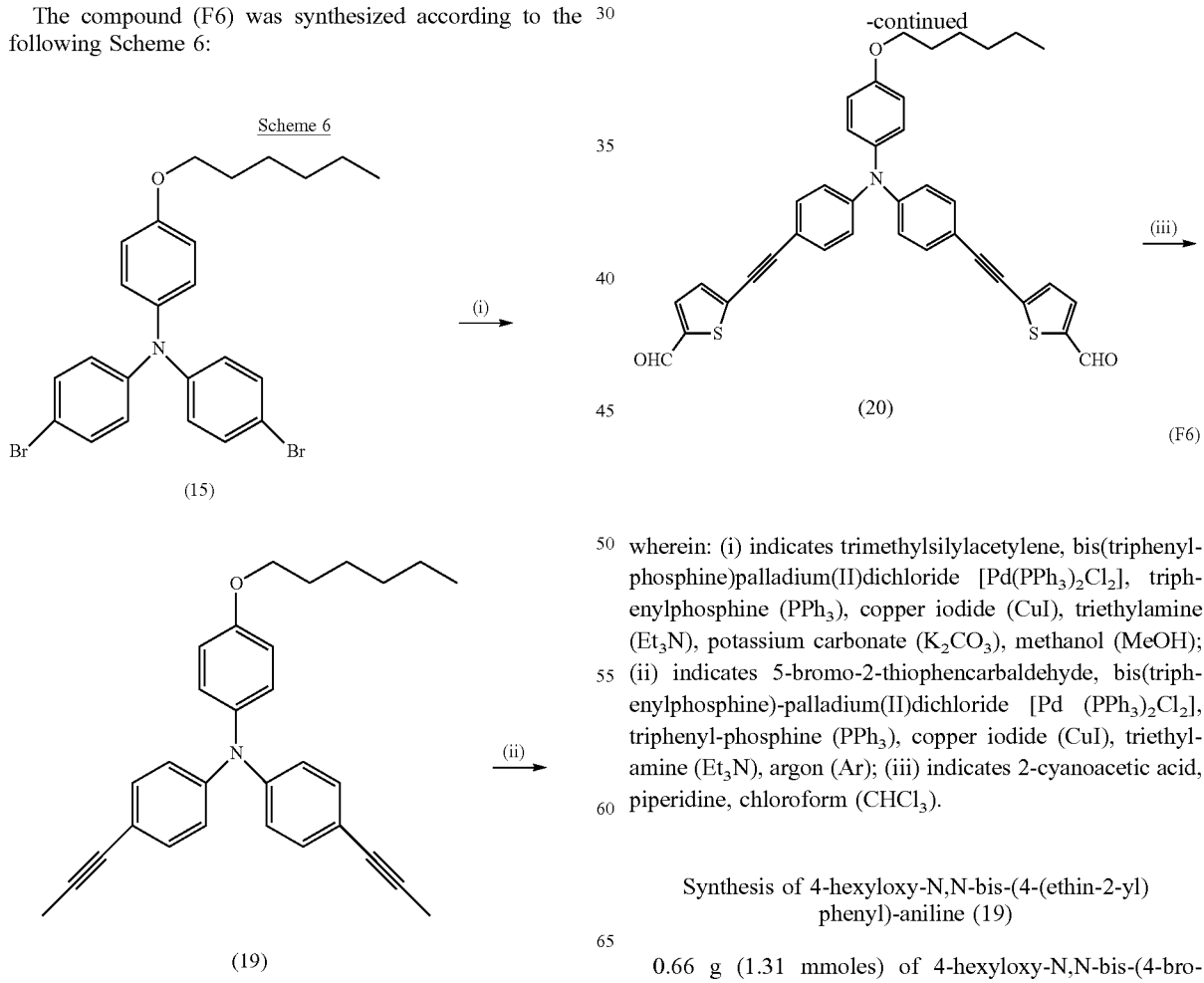

wherein: (i) indicates trimethylsilylacetylene, bis(triphenylphosphine)palladium(II)dichloride [Pd(PPh$_3$)$_2$Cl$_2$], triphenylphosphine (PPh$_3$), copper iodide (CuI), triethylamine (Et$_3$N), potassium carbonate (K$_2$CO$_3$), methanol (MeOH); (ii) indicates 5-bromo-2-thiophencarbaldehyde, bis(triphenylphosphine)-palladium(II)dichloride [Pd (PPh$_3$)$_2$Cl$_2$], triphenyl-phosphine (PPh$_3$), copper iodide (CuI), triethylamine (Et$_3$N), argon (Ar); (iii) indicates 2-cyanoacetic acid, piperidine, chloroform (CHCl$_3$).

Synthesis of 4-hexyloxy-N,N-bis-(4-(ethin-2-yl)phenyl)-aniline (19)

0.66 g (1.31 mmoles) of 4-hexyloxy-N,N-bis-(4-bromophenyl)aniline (15) obtained as described in Example 5, 2.57 g (26.2 mmoles) of trimethylsilylacetylene, 0.09 g (0.13 mmoles) of bis(triphenylphosphine)palladium(II)dichloride [$Pd(PPh_3)_2Cl_2$], 0.03 g (0.13 mmoles) of triphenylphosphine ($PPh_3$), 0.025 g (0.13 mmoles) of copper iodide (CuI) and 10 ml of triethylamine ($Et_3N$), were introduced into a 100 ml flask, previously anhydrified and maintained under a flow of nitrogen ($N_2$). The reaction mixture was put under stirring and heated to 75° C., for 29 hours. The reaction was then quenched by adding 50 ml of diethyl ether ($Et_2O$) and the whole mixture was poured into a 500 ml flask containing 150 ml of a saturated aqueous solution of ammonium chloride ($NH_4Cl$). The whole mixture was kept under magnetic stirring, for 30 minutes, at room temperature (25° C.) and then extracted with diethyl ether ($Et_2O$) (4×100 ml). The organic phase obtained was dried on sodium sulfate ($Na_2SO_4$) and the solvent was eliminated by evaporation at reduced pressure, obtaining a dark yellow liquid which was treated with 100 ml of a saturated solution of potassium carbonate ($K_2CO_3$) in methanol (MeOH): the whole mixture was kept, under stirring, at room temperature (25° C.), for 24 hours, and then subjected to filtration. The organic phase obtained was washed with water (4×200 ml) and dried on sodium sulfate ($Na_2SO_4$) and the solvent was eliminated by evaporation. A crude oil was obtained which was purified by flash chromatography on silica gel, using as eluent a mixture of ethyl phosphate (ETP)/dichloromethane ($CH_2Cl_2$) (95:5 v/v), obtaining 0.075 g (yield 15%) of 4-hexyloxy-N,N-bis-(4-(ethin-2-yl)phenyl)aniline (19), as a colourless oil.

Said 4-hexyloxy-N,N-bis-(4-(ethin-2-yl)phenyl)-aniline (19) was characterized by means of $^1$H-NMR (500 MHz; $CDCl_3$; $Me_4Si$) obtaining the following spectrum: $\delta_H$ 7.33 (4 H, d, J 8.7), 7.04 (2 H, d, J 8.9), 6.96 (4 H, d, J 8.7), 6.85 (2 H, d, J 8.9), 3.94 (2 H, t, J 6.6), 3.02 (2 H, s), 1.82-1.75 (2 H, m), 1.51-1.43 (2 H, m), 1.37-1.32 (4 H, m), 0.91 (3 H, t, J 7.0).

Synthesis of 4-hexyloxy-N,N-bis-{4-[(5-formylthieno-2-yl)ethin-2-yl]phenyl}aniline (20)

0.11 g (0.28 mmoles) of 4-hexyloxy-N,N-bis-(4-(ethin-2-yl)phenyl)aniline (19) obtained as described above, 0.57 g (5.60 mmoles) of 5-bromo-2-thiophencarbaldehyde [obtained as described by Zhan H. et al., in "*Macromolecules*" (2011), Vol. 44, pages 5155-5167], 0.02 g (0.03 mmoles) of bis(triphenylphosphine)palladium(II)dichloride [$Pd(PPh_3)_2Cl_2$], 0.007 g (0.03 mmoles) of triphenylphosphine ($PPh_3$), 0.005 g (0.03 mmoles) of copper iodide (CuI) and 10 ml of triethylamine ($Et_3N$), were introduced into a 100 ml flask, previously anhydrified and maintained under a flow of nitrogen ($N_2$): the reaction mixture appeared orange-coloured and was kept, under stirring, at room temperature (25° C.), for 24 hours. The reaction was then quenched by adding 10 ml of water and subsequently 70 ml of diethyl ether ($Et_2O$) and the whole mixture was poured into a 500 ml flask containing 150 ml of a saturated aqueous solution of ammonium chloride ($NH_4Cl$): the whole mixture was kept, under stirring, at room temperature (25° C.), for 24 hours and then subjected to filtration. The organic phase obtained was washed with water (4×200 ml) and dried on sodium sulfate ($Na_2SO_4$) and the solvent was eliminated by evaporation at reduced pressure. A crude oil was obtained which was purified by flash chromatography on silica gel, using as eluent a mixture of ethyl phosphate (ETP)/dichloromethane ($CH_2Cl_2$) (1:9 v/v), obtaining 0.10 g (yield 57%) of 4-hexyloxy-N,N-bis-{4-[(5-formylthieno-2-yl)ethin-2-yl]phenyl}aniline (20) as an orange oil.

Said 4-hexyloxy-N,N-bis-{4-[(5-formylthieno-2-yl)-ethin-2-yl]phenyl}aniline (20) was characterized by means of $^1$H-NMR (500 MHz; $CDCl_3$; $Me_4Si$) obtaining the following spectrum: $\delta_H$ 9.85 (2 H, s), 7.66 (2 H, d, J 3.9), 7.39 (2 H, d, J 8.8), 7.27 (2 H, d, J 3.9), 7.07 (2 H, d, J 8.9), 7.03 (2 H, d, J 8.8), 6.89 (2 H, d, J 8.9), 3.95 (2 H, t, J 6.7), 1.82-1.75 (2 H, m), 1.51-1.43 (2 H, m), 1.37-1.32 (4 H, m), 0.91 (3 H, t, J 7.0).

Synthesis of the Compound (F6)

0.10 g (0.16 mmoles) of 4-hexyloxy-N,N-bis-{4-[(5-formylthieno-2-yl)-ethin-2-yl]phenyl}aniline (20) obtained as described above and 10 ml of chloroform ($CHCl_3$), where introduced in a 50 ml flask, previously anhydrified and maintained under a flow of nitrogen ($N_2$): a solution of cyanoacetic acid (0.28 g, 3.26 mmoles) and piperidine (0.03 g, 3.59 mmoles) in 5 ml of chloroform ($CHCl_3$) was then slowly added dropwise to the solution obtained. At the end of the dripping, the reaction mixture was heated to the reflux temperature of the solvent, for 12 hours: in this phase, the solution passed from light orange to a dark red colour. The reaction mixture was then quenched by adding 1 ml of water and the solvent was eliminated by evaporation at reduced pressure, obtaining a dark red solid which was then suspended in 10 ml of water. After cooling the suspension obtained to 0° C. with an ice bath, 10 ml of an aqueous solution of hydrochloric acid (HCl) at 10% were added: the whole mixture was kept at 0° C., under stirring, for 1 hour. The solid formed was subsequently recovered by filtration with a Hirsh filter, washed with water (3×10 ml) and dried under vacuum obtaining 0.08 g (yield 69%) of the compound (F6), as a dark purple solid.

Said compound (F6) was characterized by means of $^1$H-NMR (500 MHz; DMSO-$d_6$; $Me_4Si$) obtaining the following spectrum: $\delta_H$ 8.45 (2 H, s), 7.95 (2 H, d, J 3.9), 7.53 (2 H, d, J 3.9), 7.52 (4 H, d, J 8.9), 7.13 (2 H, d, J 8.9), 7.04-6.98 (6 H, m), 3.98 (2 H, t, J 6.4), 1.77-1.67 (2 H, m), 1.47-1.37 (2 H, m), 1.34-1.29 (4 H, m), 0.89 (3 H, t, J=7.1).

Said compound (F6) was also characterized by means of $^{13}$C-NMR obtaining the following spectrum: $\delta_C$ (125.77 MHz; DMSO-$d_6$; $Me_4Si$) 138.25, 137.04, 133.36, 130.74, 129.17, 122.33, 117.23, 116.48, 114.52, 99.09, 82.22, 68.22, 31.46, 29.15, 25.66, 22.54, 14.37.

Example 7
Preparation of the Compound (F7)
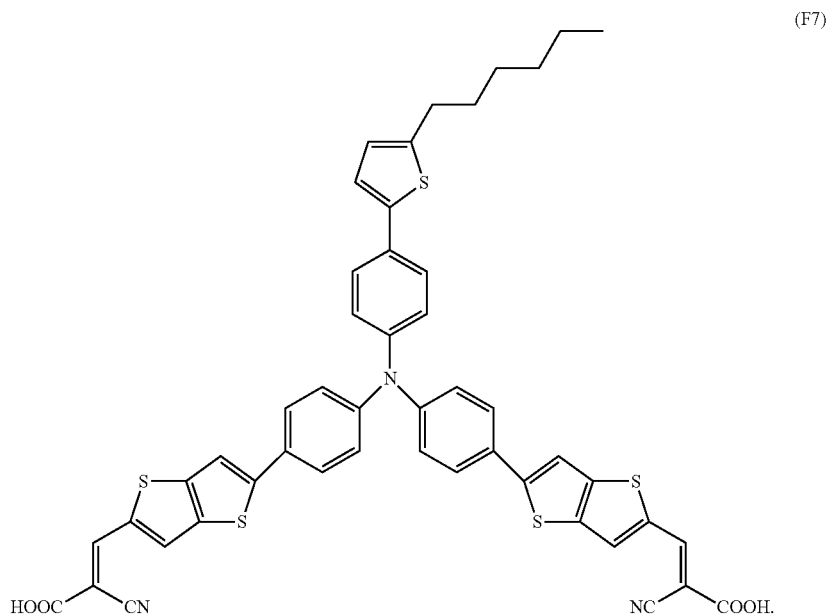 [SMILES: CCCCCCc1ccc(-c2ccc(N(c3ccc(-c4cc5sc(/C=C(\C#N)C(=O)O)cc5s4)cc3)c3ccc(-c4cc5sc(/C=C(\C#N)C(=O)O)cc5s4)cc3)cc2)s1]
The compound (F7) was synthesized according to the following Scheme 7:
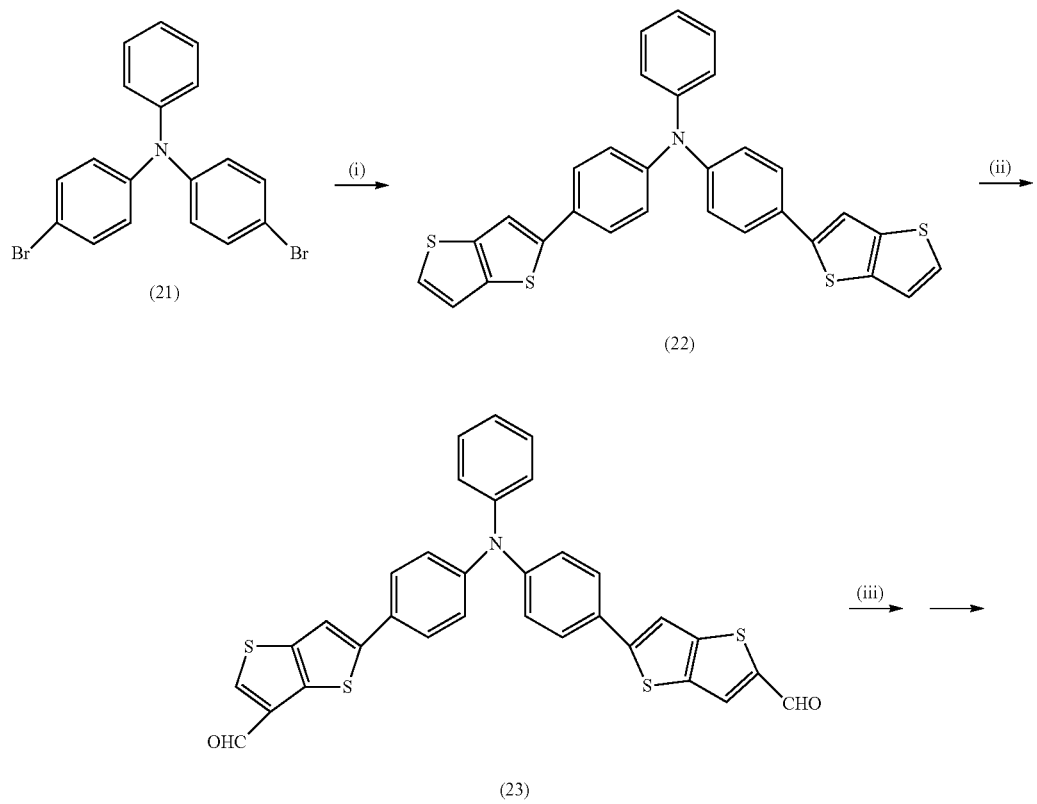

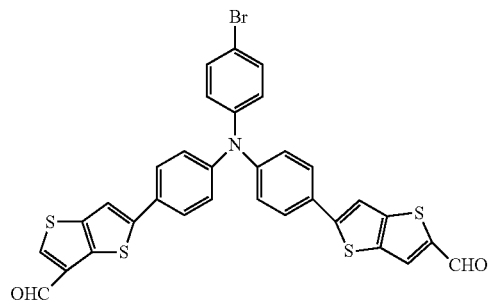

(24)

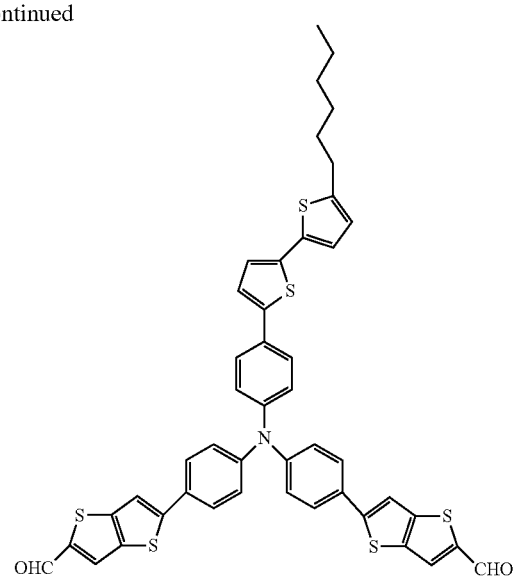

(25)

(F7)

wherein: (i) indicates 5-(4,4,4,5,5-tetramethyl-1,3,2-dioxaborolan)thieno[3,2-b]thiophene, 1,1'-bis(diphenyl-phosphine)ferrocene-palladium(II)dichloride complexed with dichloromethane [Pd(dppf)Cl$_2$], potassium carbonate (K$_2$CO$_3$), methanol (MeOH), toluene; (ii) indicates dimethylformamide (DMF), phosphorous oxychloride (POCl$_3$); (iii) indicates N-bromosuccinimide (NBS), dimethylformamide (DMF), (iv) indicates 5-hexyl-2-thiophene boronic acid pinacol ester, 1,1'-bis(diphenyl-phosphine)ferrocene-palladium(II)dichloride complexed with dichloromethane [Pd(dppf)Cl$_2$], potassium carbonate (K$_2$CO$_3$), methanol (MeOH), toluene; (v) indicates 2-cyanoacetic acid, piperidine, chloroform (CHCl$_3$).

Synthesis of N,N-bis-(4-(thieno[3,2-b]thien-5-yl)-phenyl)aniline (22)

6 ml of a mixture of methanol (MeOH)/toluene (1:1 v/v), 0.44 g (1.0 mmoles) of N,N-bis-(4-bromophenyl)aniline (21) [obtained as described by D. Sahu et al., in "*Journal of Materials Chemistry*" (2012), Vol. 22, pages 7945-7953], 0.67 g (2.5 mmoles) of 5-(4,4,4,5,5-tetramethyl-1,3,2-dioxaborolane)-thieno[3,2-b]thiophene [obtained as described by Alesi S. et al., in "Green Chemistry" (2008), Vol. 10, pages 517-523], 0.08 g (0.10 mmoles) of 1,1'-bis(diphenylphosphine)ferrocene-palladium(II)dichloride complexed with dichloromethane [Pd(dppf)Cl$_2$] and 0.69 g (5.0 mmoles) of potassium carbonate (K$_2$CO$_3$), were introduced into a 30 ml microwave test-tube.

The test-tube was then sealed and heated with microwaves to 70° C., 50 W, for 40 minutes. 20 ml of dichloromethane (CH$_2$Cl$_2$) were then added and the whole mixture was poured into 50 ml of a saturated aqueous solution of ammonium chloride (NH$_4$Cl) and extracted with dichloromethane (CH$_2$Cl$_2$) (3×20 ml). The organic phase obtained was washed with water (2×15 ml) and dried on sodium sulfate (Na$_2$SO$_4$). After eliminating the solvent by evaporation at reduced pressure, a crude oil was obtained, which was purified by means of flash chromatography on silica gel, using as eluent a mixture of n-hexane/dichloromethane (CH$_2$Cl$_2$) (7:3, v/v), obtaining 0.20 g (yield 40%) of N,N-bis-(4-(thieno[3,2-b]thien-5-yl)-phenyl)aniline (22), as a yellow solid.

Said N,N-bis-(4-(thieno[3,2-b]thien-5-yl)-phenyl)-aniline (22) was characterized by means of $^1$H-NMR (500 MHz; CDCl$_3$; Me$_4$Si) obtaining the following spectrum: $\delta_H$ 7.51 (4 H, d, J 8.6), 7.41 (2 H, s), 7.34 (2 H, d, J 5.2), 7.30 (1 H, t, J 8.0), 7.24 (2 H, d, J 5.2), 7.17 (2 H, t, J 8.3), 7.13 (4 H, d, J 8.6).

Synthesis of N,N-bis-(4-(5'-formyl-thieno[3,2-b]thien-5-yl)phenyl)aniline (23)

0.07 g (0.90 mmoles) of dimethyl formamide (DMF) were introduced into a 100 ml flask, previously anhydrified and maintained under a flow of nitrogen (N$_2$), and subsequently, after cooling to a temperature of −10° C., 0.14 g (0.90 mmoles) of phosphorous oxychloride (POCl$_3$) were slowly added dropwise: the formation of a vitreous white solid was observed and after 30 minutes, 10 ml of dimethylformamide (DMF) were added. After the complete dissolution of the reaction mixture, 0.20 g (0.39 mmoles) of N,N-bis-(4-(thieno[3,2-b]thien-5-yl)-phenyl)-aniline (22), obtained as described above, dissolved in 15 ml of dimethylformamide (DMF), were added. The reaction mixture was left, under stirring, at 70° C., for 4 hours. The reaction was then quenched by adding 20 ml of a saturated aqueous solution of sodium acetate (AcONa) and the whole mixture was left, under stirring, for 1 hour and then extracted with dichloromethane (CH$_2$Cl$_2$) (3×15 ml). The organic phase obtained was washed with water (2×15 ml) and dried on sodium sulfate (Na$_2$SO$_4$). After eliminating the solvent by evaporation at reduced pressure, 0.16 g (yield 72%) of N,N-bis-(4-(5'-formyl-thieno[3,2-b]thien-5-yl)phenyl)aniline (23) were obtained, as a dark orange solid.

Said N,N-bis-(4-(5'-formyl-thieno[3,2-b]thien-5-yl)-phenyl)aniline (23) was characterized by means of $^1$H-NMR (500 MHz; CDCl$_3$; Me$_4$Si) obtaining the following spectrum: $\delta_H$ 9.97 (2 H, s), 8.39 (2 H, s), 7.94 (2 H, s), 7.76 (1 H, t, J 8.5), 7.72 (4 H, d, J 8.7), 7.42 (2 H, t, J 8.1), 7.18 (2 H, d, J 7.5), 7.13 (4 H, d, J 8.7).

Synthesis of 4-bromo-N,N-bis-(4-(5'-formyl-thieno [3,2-b]thien-5-yl)phenyl)aniline (24)

0.16 g (0.28 mmoles) of N,N-bis-(4-(5'-formyl-thieno[3,2-b]thien-5-yl)phenyl)aniline (23) obtained as described above and 10 ml of dimethylformamide (DMF), were introduced into a 50 ml flask and, after cooling, the solution to 0° C. with an ice bath, a solution of N-bromosuccinimide (NBS) (0.10 g, 0.56 mmoles) in 5 ml of dimethylformamide (DMF) were then slowly added dropwise. At the end of the dripping, the reaction mixture was heated to room temperature (25° C.) and kept, under stirring, for 16 hours. The reaction mixture was then poured into a 250 ml flask containing 75 ml of water and 20 ml of diethyl ether (Et$_2$O) and was extracted with diethyl ether (Et$_2$O) (3×15 ml). The organic phase obtained was dried on sodium sulfate (Na$_2$SO$_4$) and the solvent was eliminated by evaporation at reduced pressure, obtaining 0.14 g (yield 84%) of 4-bromo-N,N-bis-(4-(5'-formyl-thieno[3,2-b]thien-5-yl)phenyl)aniline (24) as a brown solid.

Said 4-bromo-N,N-bis-(4-(5'-formyl-thieno[3,2-b]thien-5-yl)phenyl)aniline (24) was characterized by means of $^1$H-NMR (500 MHz; CDCl$_3$; Me$_4$Si) obtaining the following spectrum: $\delta_H$ 9.95 (2 H, s), 7.91 (2 H, s), 7.56 (4 H, d, J 8.2), 7.47 (2 H, s), 7.44 (2 H, d, J 8.6), 7.15 (4 H, d, J 8.5), 7.06 (2 H, d, J 8.7).

Synthesis of 4-(5-hexyl-2-thieno)-N,N-bis-(4-(5'-formyl-thieno[3,2-b]thien-5-il)phenyl)aniline (25)

6 ml of a mixture of methanol (MeOH)/toluene (1:1 v/v), 0.10 g (0.15 mmoles) of 4-bromo-N,N-bis-(4-(5'-formyl-thieno[3,2-b]thien-5-yl)phenyl)aniline (24) obtained as described above, 0.09 g (0.30 mmoles) of 5-hexyl-2-thio-phene boronic acid pinacol ester, 0.03 g (0.03 mmoles) of 1,1'-bis(diphenylphosphine)ferrocene-palladium(II)dichloride complexed with dichloromethane [Pd(dppf)Cl$_2$] and 0.11 g (0.80 mmoles) of potassium carbonate (K$_2$CO$_3$), were introduced into a 50 ml microwave test-tube. The test-tube was then sealed and heated with microwaves to 70° C., 50 W, for 40 minutes. 20 ml of dichloromethane (CH$_2$Cl$_2$) were then added and the whole mixture was poured into 50 ml of a saturated aqueous solution of ammonium chloride (NH$_4$Cl) and extracted with dichloromethane (CH$_2$Cl$_2$) (3×20 ml). The organic phase obtained was washed with water (2×15 ml) and dried on sodium sulfate (Na$_2$SO$_4$). After eliminating the solvent by evaporation at reduced pressure, a crude oil was obtained, which was purified by means of flash chromatography on silica gel, using as eluent a mixture of dichloromethane (CH$_2$Cl$_2$), obtaining 0.05 g (yield 46%) of 4-(5-hexyl-2-thieno)-N,N-bis-(4-(5'-formyl-thieno[3,2-b]thien-5-il)phenyl)-aniline (25) as an orange solid.

Said 4-(5-hexyl-2-thieno)-N,N-bis-(4-(5'-formyl-thieno [3,2-b]thien-5-il)phenyl)-aniline (25) was characterized by means of $^1$H-NMR (500 MHz; CDCl$_3$; Me$_4$Si) obtaining the following spectrum: $\delta_H$ 9.94 (2 H, s), 7.84 (2 H, s), 7.56 (4 H, d, J 8.6), 7.52 (2 H, d, J 8.5), 7.46 (2 H, s), 7.18 (4 H, d, J 8.6), 7.15 (2 H, d, J 8.5), 7.09 (1 H, d, J 3.5), 6.74 (1 H, d, J 3.0), 2.82 (2 H, t, J 7.6), 1.70 (2 H, quintet, J 7.5), 1.39 (2 H, quintet, J 6.3), 1.35-1.30 (4 H, m), 0.90 (3 H, t, J 6.7).

Synthesis of the Compound (F7)

0.05 g (0.07 mmoles) of 4-(5-hexyl-2-thieno)-N,N-bis-(4-(5'-formyl-thieno[3,2-b]thien-5-il)phenyl)-aniline (25) obtained as described above and 10 ml of chloroform (CHCl$_3$) where introduced into a 50 ml flask, previously anhydrified and maintained under a flow of nitrogen (N$_2$): a solution of cyanoacetic acid (0.06 g, 0.70 mmoles) and piperidine (0.07 g, 0.80 mmoles) in 5 ml of chloroform (CHCl$_3$) were then slowly added dropwise to the solution obtained. At the end of the dripping, the reaction mixture was heated to the reflux temperature of the solvent, for 12 hours: in this phase, the solution passed from light orange to a dark red colour. The reaction mixture was quenched by adding 1 ml of water and the solvent was eliminated by evaporation at reduced pressure, obtaining a dark red solid which was then suspended in 10 ml of water. After cooling the suspension obtained to 0° C. with an ice bath, 10 ml of an aqueous solution of hydrochloric acid (HCl) at 10% were added: the whole mixture was kept at 0° C., under stirring, for 1 hour. The solid formed was subsequently recovered by filtration with a Hirsh filter, washed with water (3×10 ml) and dried under vacuum obtaining 0.04 g (yield 65%) of the compound (F7), as a dark purple solid.

Said compound (F7) was characterized by means of $^1$H-NMR (500 MHz; DMSO-d$_6$; Me$_4$Si) obtaining the following spectrum: $\delta_H$ 8.47 (2 H, s), 8.25 (2 H, s), 7.97 (2 H, s), 7.72 (4 H, d, J 8.7), 7.59 (2 H, d, J 8.6), 7.27 (1 H, d, J 3.5), 7.16 (4 H, d, J 8.7), 7.15 (2 H, d, J 8.5), 6.84 (1 H, d, J 3.5), 2.79 (2 H, t, J 7.5), 1.65 (2 H, quintet, J 7.5), 1.35 (2 H, quintet, J 6.3), 1.32-1.28 (4 H, m), 0.87 (3 H, t, J 6.7).

Example 8
Preparation of the Compound (F8)
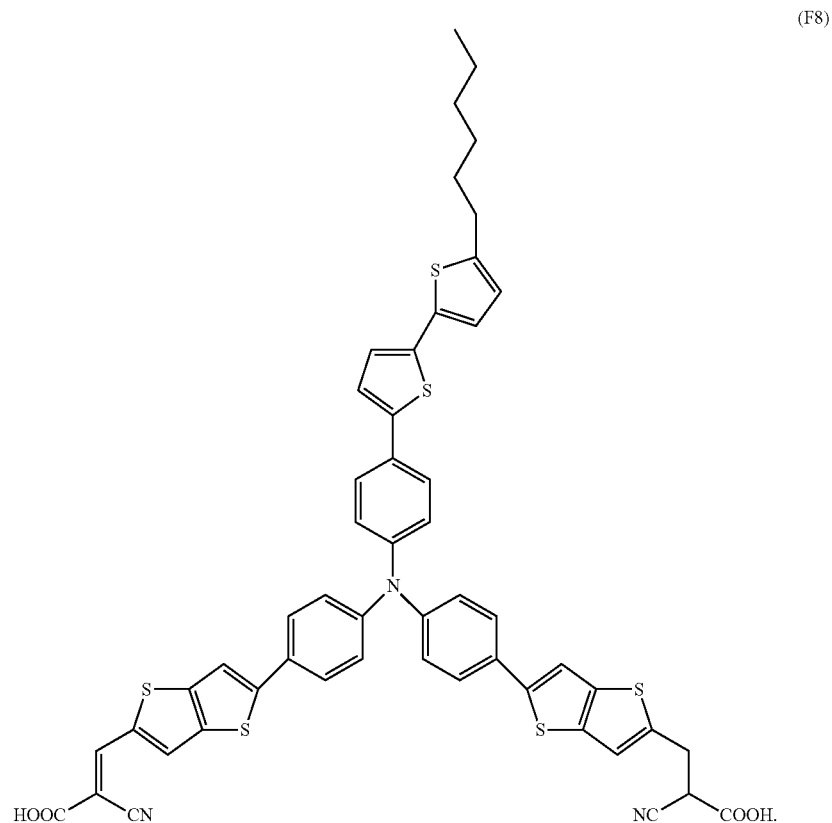 [SMILES: CCCCCCc1ccc(-c2ccc(-c3ccc(N(c4ccc(-c5cc6sc(/C=C(\C#N)C(=O)O)cc6s5)cc4)c4ccc(-c5cc6sc(CC(C#N)C(=O)O)cc6s5)cc4)cc3)s2)s1]
The compound (F8) was synthesized according to the following Scheme 8:
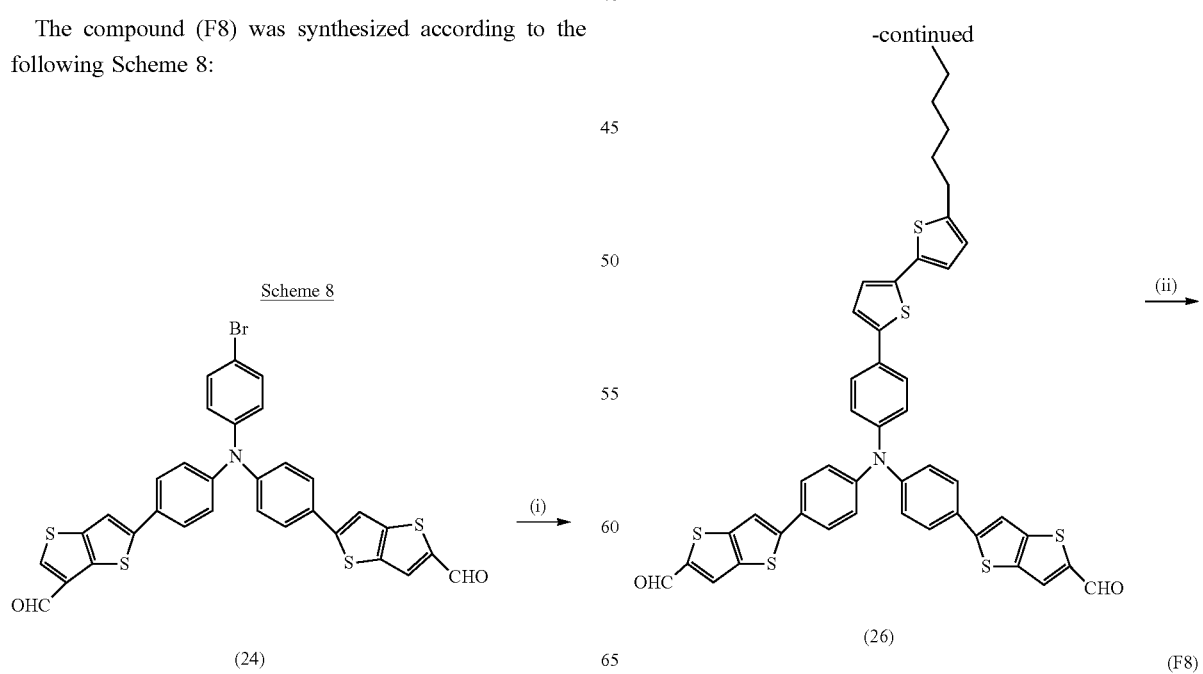

wherein: (i) indicates 5'-hexyl-2,2'-bithiophene-5 boronic acid pinacol ester, 1,1'-bis(diphenyl-phosphine)ferrocene-palladium(II)dichloride complexed with dichloromethane [Pd(dppf)Cl$_2$], potassium carbonate (K$_2$CO$_3$), methanol (MeOH), toluene; (ii) indicates 2-cyanoacetic acid, piperidine, chloroform (CHCl$_3$).

Synthesis of 4-(5'-hexyl-2,2'-bithien-5-yl)-N,N-bis-(4-(5'-formyl-thieno[3,2-b]thien-5-yl)phenyl)aniline (26)

6 ml of a mixture of methanol (MeOH)/toluene (1:1 v/v), 0.05 g (0.08 mmoles) of 4-bromo-N,N-bis-(4-(5'-formyl-thieno[3,2-b]thien-5-yl)phenyl)aniline (24) obtained as described in Example 7, 0.07 g (0.30 mmoles) of 5'-hexyl-2,2'-bithiophene-5 boronic acid pinacol ester, 0.01 g (0.01 mmoles) of 1,1'-bis(diphenylphosphine)ferrocene-palladium(II)dichloride complexed with dichloromethane [Pd(dppf)Cl$_2$] and 0.05 g (0.40 mmoles) of potassium carbonate (K$_2$CO$_3$), were introduced into a 50 ml microwave test-tube. The test-tube was then sealed and heated with microwaves to 70° C., 50 W, for 40 minutes. 20 ml of dichloromethane (CH$_2$Cl$_2$) were then added and the whole mixture was poured into 50 ml of a saturated aqueous solution of ammonium chloride (NH$_4$Cl) and extracted with dichloromethane (CH$_2$Cl$_2$) (3×20 ml). The organic phase obtained was washed with water (2×15 ml) and dried on sodium sulfate (Na$_2$SO$_4$). After eliminating the solvent by evaporation at reduced pressure, a crude oil was obtained, which was purified by means of flash chromatography on silica gel, using as eluent a mixture of dichloromethane (CH$_2$Cl$_2$), obtaining 0.03 g (yield 50%) of 4-(5'-hexyl-2,2'-bithien-5-yl)-N,N-bis-(4-(5'-formyl-thieno[3,2-b]thien-5-yl)phenyl)aniline (26) as a dark orange solid.

Said 4-(5'-hexyl-2,2'-bithien-5-yl)-N,N-bis-(4-(5'-formyl-thieno[3,2-b]thien-5-yl)phenyl)aniline (26) was characterized by means of $^1$H-NMR (500 MHz; CDCl$_3$; Me$_4$Si) obtaining the following spectrum: δ$_H$ 9.95 (2 H, s), 7.90 (2 H, s), 7.57 (4 H, d, J 8.7), 7.54 (2 H, d, J 8.7), 7.47 (2 H, s), 7.19 (4 H, d, J 8.7), 7.16 (1 H, d, J 3.7), 7.15 (2 H, d, J 8.7), 7.06 (1 H, d, J 3.6), 7.00 (1 H, d, J 3.5), 6.69 (1 H, d, J 3.5), 2.79 (2 H, t, J 7.6), 1.69 (2 H, quintet, J 7.5), 1.42-1.36 (2 H, m), 1.34-1.29 (4 H, m), 0.89 (3 H, t, J 7.0).

Synthesis of the Compound (F8)

0.03 g (0.04 mmoles) of 4-(5'-hexyl-2,2'-bithien-5-yl)-N,N-bis-(4-(5'-formyl-thieno[3,2-b]thien-5-yl)-phenyl)aniline (26) obtained as described above and 10 ml of chloroform (CHCl$_3$), where introduced into a 50 ml flask, previously anhydrified and maintained under a flow of nitrogen (N$_2$): a solution of cyanoacetic acid (0.03 g, 0.40 mmoles) and piperidine (0.04 g, 0.50 mmoles) in 5 ml of chloroform (CHCl$_3$) was then slowly added dropwise to the solution obtained. At the end of the dripping, the reaction mixture was heated to the reflux temperature of the solvent, for 12 hours: in this phase, the solution passed from light orange to a dark red colour. The reaction mixture was quenched by adding 1 ml of water and the solvent was eliminated by evaporation at reduced pressure, obtaining a dark red solid which was then suspended in 10 ml of water. After cooling the suspension obtained to 0° C. with an ice bath, 10 ml of an aqueous solution of hydrochloric acid (HCl) at 10% were added: the whole mixture was kept at 0° C., under stirring for 1 hour. The solid formed was subsequently recovered by filtration with a Hirsh filter, washed with water (3×10 ml) and dried under vacuum obtaining 0.03 g (yield 65%) of the compound (F8), as a dark purple solid.

Said compound (F8) was characterized by means of $^1$H-NMR (500 MHz; DMSO-d$_6$; Me$_4$Si) obtaining the following spectrum: δ$_H$ 8.56 (2 H, s), 8.31 (2 H, s), 7.99 (2 H, s), 7.74 (4 H, d, J 8.6), 7.66 (2 H, d, J 8.6), 7.42 (1 H, d, J 3.7), 7.22 (1 H, d, J 3.7), 7.20-7.12 (7 H, m), 6.82 (1 H, d, J 3.4), 2.79 (2 H, t, J 7.5), 1.65 (2 H, quintet, J 7.5), 1.35 (2 H, quintet, J 6.3), 1.32-1.28 (4 H, m), 0.87 (3 H, t, J 6.7).

Example 9

Synthesis of the Compound (F9)

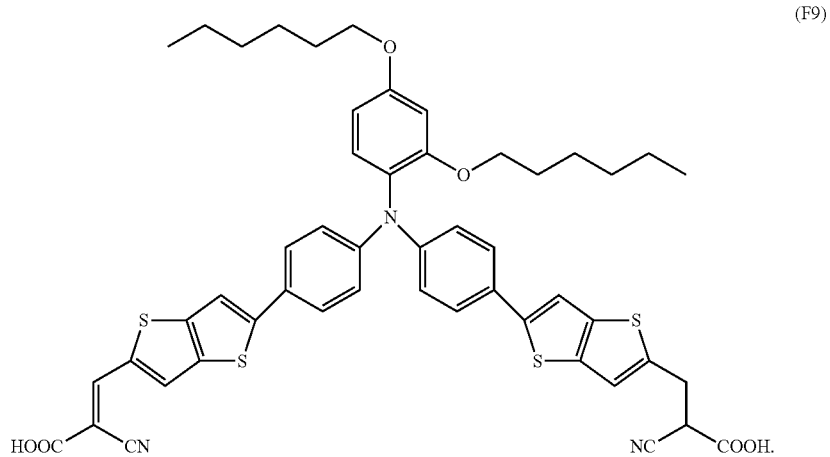 [SMILES: CCCCCCOc1ccc(N(c2ccc(-c3cc4sc(/C=C(\C#N)C(=O)O)cc4s3)cc2)c2ccc(-c3cc4sc(CC(C#N)C(=O)O)cc4s3)cc2)c(OCCCCCC)c1]

(F9)

The compound (F9) was synthesized according to the following Scheme 9:

Scheme 9

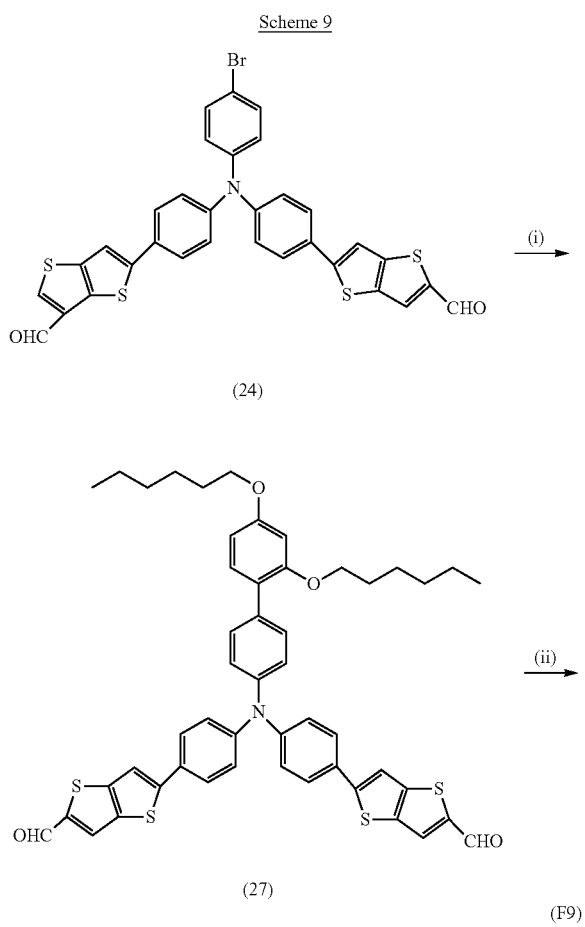

wherein: (i) indicates 4,4,5,5-tetramethyl-2-(2,4-dihexyloxyphenyl)-1,3,2-dioxaborolane, 1,1'-bis(diphenylphosphine)ferrocene-palladium(II)dichloride complexed with dichloromethane [Pd(dppf)Cl$_2$], potassium carbonate (K$_2$CO$_3$), methanol (MeOH), toluene; (ii) indicates 2-cyanoacetic acid, piperidine, chloroform (CHCl$_3$).

Synthesis of 4-(2',4'-dihexyloxyphenyl)-N,N-bis-(4-(5'-formyl-thieno[3,2-b]thien-5-yl)phenyl)aniline (27)

6 ml of a mixture of methanol (MeOH)/toluene (1:1 v/v), 0.10 g (0.15 mmoles) of 4-bromo-N,N-bis-(4-(5'-formyl-thieno[3,2-b]thien-5-yl)phenyl)aniline (24) obtained as described in Example 7, 0.12 g (0.30 mmoles) of 4,4,5,5-tetramethyl-2-(2,4-dihexyloxyphenyl)-1,3,2-dioxaborolane [obtained as described by Tsao H. N. et al., in "ChemSusChem" (2011), Vol. 4, pages 591-594], 0.03 g (0.03 mmoles) of 1,1'-bis(diphenylphosphine)ferrocene-palladium(II)dichloride complexed with dichloromethane [Pd(dppf)Cl$_2$] and 0.11 g (0.80 mmoles) of potassium carbonate (K$_2$CO$_3$), were introduced into a 50 ml microwave test-tube. The test-tube was then sealed and heated with microwaves to 70° C., 50 W, for 40 minutes. 20 ml of dichloromethane (CH$_2$Cl$_2$) were then added and the whole mixture was poured into 50 ml of a saturated aqueous solution of ammonium chloride (NH$_4$Cl) and extracted with dichloromethane (CH$_2$Cl$_2$) (3×20 ml). The organic phase obtained was washed with water (2×15 ml) and dried on sodium sulfate (Na$_2$SO$_4$). After eliminating the solvent by evaporation at reduced pressure, a crude oil was obtained, which was purified by means of flash chromatography on silica gel, using as eluent a mixture of dichloromethane (CH$_2$Cl$_2$), obtaining 0.09 g (yield 66%) of 4-(2',4'-dihexyloxyphenyl)-N,N-bis-(4-(5'-formyl-thieno[3,2-b]thien-5-yl)phenyl)aniline (27) as a dark orange solid.

Said 4-(2',4'-dihexyloxyphenyl)-N,N-bis-(4-(5'-formyl-thieno[3,2-b]thien-5-yl)phenyl)aniline (27) was characterized by means of $^1$H-NMR (500 MHz; CDCl$_3$; Me$_4$Si) obtaining the following spectrum: $\delta_H$ 9.95 (2 H, s), 7.90 (2 H, s), 7.56 (4 H, d, J 8.7), 7.52 (2 H, d, J 8.6), 7.47 (2 H, s), 7.28 (1 H, s), 7.21 (4 H, d, J 8.7), 7.18 (2 H, d, J 8.6), 6.58-6.54 (2 H, m), 4.02-3.95 (4 H, m), 1.81 (2 H, quintet, J 7.9), 1.76 (2 H, quintet, J 7.9) 1.52-1.45 (2 H, m), 1.52-1.45 (2 H, m), 1.44-1.39 (2 H, m), 1.38-1.34 (4 H, m), 1.33-1.28 (4 H, m), 0.92 (3 H, t, J 6.9), 0.88 (3 H, t, J 7.0).

Synthesis of the Compound (F9)

0.09 g (0.10 mmoles) of 4-(2',4'-dihexyloxyphenyl)-N,N-bis-(4-(5'-formyl-thieno[3,2-b]thien-5-yl)phenyl)aniline (27) obtained as described above and 10 ml of chloroform (CHCl$_3$), where introduced into a 50 ml flask, previously anhydrified and maintained under a flow of nitrogen (N$_2$): a solution of cyanoacetic acid (0.09 g, 1.0 mmole) and piperidine (0.09 g, 1.1 mmoles) in 5 ml of chloroform (CHCl$_3$) were then slowly added dropwise to the solution obtained. At the end of the dripping, the reaction mixture was heated to the reflux temperature of the solvent, for 12 hours: in this phase, the solution passed from light orange to a dark red colour. The reaction mixture was then quenched by adding 1 ml of water and the solvent was eliminated by evaporation at reduced pressure, obtaining a dark red solid which was then suspended in 10 ml of water. After cooling the suspension obtained to 0° C. with an ice bath, 10 ml of an aqueous solution of hydrochloric acid (HCl) at 10% were added: the whole mixture was kept at 0° C., under stirring, for 1 hour. The solid formed was subsequently recovered by filtration with a Hirsh filter, washed with water (3×10 ml) and dried under vacuum obtaining 0.06 g (yield 59%) of the compound (F9), as a dark purple solid.

Said compound (F9) was characterized by means of $^1$H-NMR (500 MHz; DMSO-d$_6$; Me$_4$Si) obtaining the following spectrum: $\delta_H$ 8.46 (2 H, s), 8.23 (2 H, s), 7.95 (2 H, s), 7.69 (4 H, d, J 8.5), 7.49 (2 H, d, J 8.4), 7.23 (1 H, d, J 8.2), 7.16-7.08 (7 H, m), 6.56-6.48 (1 H, m), 4.02-3.95 (4 H, m), 1.81 (2 H, quintet, J 7.9), 1.76 (2 H, quintet, J 7.9) 1.52-1.45 (2 H, m), 1.52-1.45 (2 H, m), 1.44-1.39 (2 H, m), 1.38-1.34 (4 H, m), 1.33-1.28 (4 H, m), 0.92 (3 H, t, J 6.9), 0.88 (3 H, t, J 7.0).

Example 10

Synthesis of the Compound (F10)

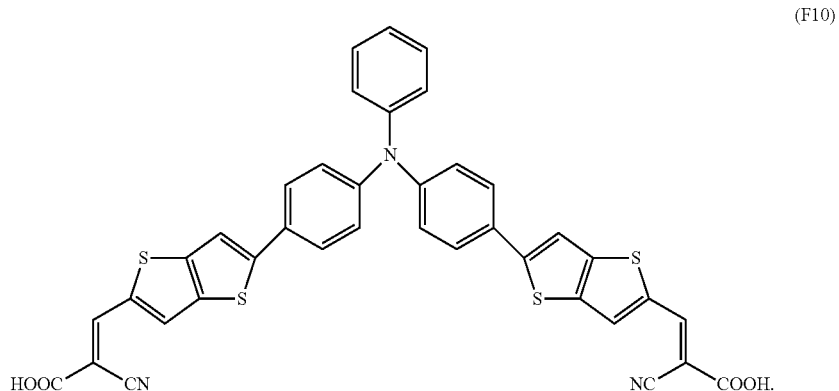 [SMILES: N#C/C(=C\c1cc2sc(-c3ccc(N(c4ccccc4)c4ccc(-c5cc6sc(/C=C(\C#N)C(=O)O)cc6s5)cc4)cc3)cc2s1)C(=O)O]

(F10)

The compound (F10) was synthesized according to the following Scheme 10:

Scheme 10

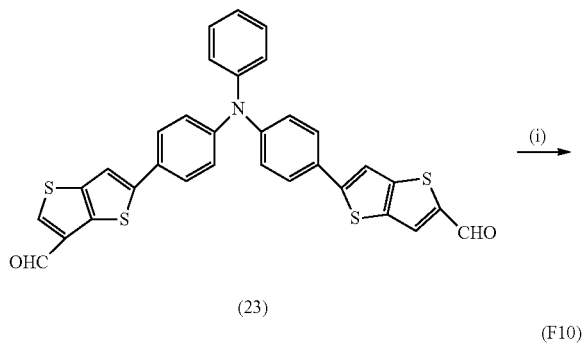

wherein: (i) indicates 2-cyanoacetic acid, piperidine, chloroform ($CHCl_3$).

Synthesis of the Compound (F10)

0.29 g (0.50 mmoles) of N,N-bis-(4-(5'-formyl-thieno[3,2-b]thien-5-yl)phenyl)aniline (23), obtained as described in Example 7, and 10 ml of chloroform ($CHCl_3$), where introduced into a 50 ml flask, previously anhydrified and maintained under a flow of nitrogen ($N_2$): a solution of cyanoacetic acid (0.43 g, 5.0 mmole) and piperidine (0.47 g, 5.5 mmoles) in 5 ml of chloroform ($CHCl_3$) were then slowly added dropwise to the solution obtained. At the end of the dripping, the reaction mixture was heated to the reflux temperature of the solvent, for 8 hours: in this phase, the solution passed from light orange to a dark red colour. The reaction mixture was then quenched by adding 1 ml of water and the solvent was eliminated by evaporation at reduced pressure, obtaining a dark red solid which was then suspended in 10 ml of water. After cooling the suspension obtained to 0° C. with an ice bath, 10 ml of an aqueous solution of hydrochloric acid (HCl) at 10% were added: the whole mixture was kept at 0° C., under stirring, for 1 hour. The solid formed was subsequently recovered by filtration with a Hirsh filter, washed with water (3×10 ml) and dried under vacuum obtaining 0.12 g (yield 32%) of the compound (F10), as a dark purple solid.

Said compound (F9) was characterized by means of $^1$H-NMR (500 MHz; DMSO-$d_6$; $Me_4Si$) obtaining the following spectrum: $\delta_H$ 8.57 (2 H, s), 8.33 (2 H, s), 7.98 (2 H, s), 7.71 (4 H, d, J 8.6), 7.69 (1 H, t, J 8.5), 7.42 (2 H, t, J 8.1), 7.19 (2 H, d, J 7.5), 7.14 (4 H, d, J 8.7).

Example 11

Preparation of a Dye Sensitized Solar Cell (DSSC)

The titanium dioxide ($TiO_2$) electrodes were prepared by the deposition (doctor blade technique) of a colloidal paste containing titanium dioxide ($TiO_2$) having a dimension of 20 nm ($TiO_2$ paste DSL 18NR-T—Dyesol) on FTO conductive glass (Hartford Glass Co., TEC 8, having a thickness of 2.3 mm and a sheet resistance of 6 $\Omega/cm^2$-9 $\Omega/cm^2$), previously cleaned with water and ethanol, treated with a plasma cleaner, at 100 W, for 10 minutes, immersed in a freshly prepared aqueous solution of titanium tetrachloride ($TiCl_4$) ($4.5 \times 10^{-2}$ M), at 70° C., for 30 minutes, and finally washed with ethanol.

After a first drying at 125° C., for 15 minutes, a diffusion reflecting layer containing particles of titanium dioxide ($TiO_2$) with dimensions >100 nm (Ti-Nanoxide R/SP—Solaronix), was deposited (doctor blade technique) on the first layer of titanium dioxide ($TiO_2$) and sintered at 500° C., for 30 minutes. The glass coated with the film of titanium dioxide ($TiO_2$) was cooled to room temperature (25° C.) and immersed again in a freshly prepared aqueous solution of titanium tetrachloride ($TiCl_4$) ($4.5 \times 10^{-2}$ M), at 70° C., for 30 minutes, and finally washed with ethanol and sintered again at 500° C., for 30 minutes, obtaining a final thickness of the electrode ranging from 8 μm to 12 μm.

After sintering, the glass coated with titanium dioxide ($TiO_2$) film, was cooled to about 80° C.-100° C. and immediately immersed in a solution in dichloromethane ($CH_2Cl_2$) ($5 \times 10^{-4}$ M) of the compound (F1) obtained as described in Example 1, at room temperature (25° C.), for 24 hours. The glass coated with coloured titania was washed with ethanol and dried at room temperature (25° C.), under a flow of nitrogen ($N_2$).

A Surlyn spacer having a thickness of 50 μm (TPS 065093-50—Dyesol) was used for sealing the photo-anode obtained as described above and the counter-electrode consisting of platinized FTO glass (Hartford Glass Co., TEC 8, having a thickness of 2.3 mm and a sheet resistance of 6 $\Omega/cm^2$-9 $\Omega/cm^2$). The cell was subsequently filled, through a hole previously made in the platinized FTO glass, with an electrolyte solution having the following composition: N-methyl-N-butylimidazolium iodide (0.6 M), iodine (0.04 M), lithium iodide (LiI) (0.025 M), guanidinium-thiocyanate (0.05 M) and tert-butylpiridine (0.28 M), in a 15:85 mixture (v/v) of valeronitrile and acetonitrile.

The active area of the cell, calculated by means of a microphotograph, was 0.1435 $cm^2$.

The photovoltaic performance of the cell was measured with a solar simulator (Abet 2000) equipped with a 300 W xenon light source, the light intensity was calibrated with a standard silicon solar cell ("VLSI Standard" SRC-1000-RTD-KGS), the current-voltage characteristics were obtained by applying an external voltage to the cell and measuring the photocurrent generated with a "Keithley 2602A" digital multimeter (3A DC, 10A Pulse). The following results were obtained:

Voc (open-circuit photovoltage)=0.62 V;
FF (Fill Factor)=71.9%;
Jsc (short-circuit current density)=14.7 $mA/cm^2$;
η (photoelectric transformation efficiency): 6.5%.

Examples 12-20

Preparation of Dye Sensitized Solar Cells (DSSCs)

Following the procedure described in Example 11, Dye Sensitized Solar Cells were prepared using compounds (F2), (F3), (F4), (F5), (F6), (F7), (F8), (F9) and (F10) as dyes, prepared according to what is described in Examples 2, 3, 4, 5, 6, 7, 8, 9 and 10, respectively. The photovoltaic performances were measured on each cell thus obtained, as described in Example 11. The values obtained are indicated in Table 2.

Table 2 indicates in order: the example number (Example), the number referring to the formula of the dye used, the active area of the cell, Voc (open-circuit voltage), FF (Fill Factor), Jsc (short-circuit current density) and η (photoelectric transformation efficiency).

TABLE 2

| Example | Dye | Area ($cm^2$) | Voc (V) | FF (%) | Jsc ($mA/cm^2$) | η (%) |
| --- | --- | --- | --- | --- | --- | --- |
| 12 | (F2) | 0.1646 | 0.59 | 69.4 | 12.3 | 5.1 |
| 13 | (F3) | 0.1231 | 0.69 | 73.0 | 14.9 | 7.5 |
| 14 | (F4) | 0.1135 | 0.69 | 70.4 | 19.5 | 9.4 |
| 15 | (F5) | 0.1286 | 0.62 | 64.3 | 16.8 | 6.7 |
| 16 | (F6) | 0.1027 | 0.63 | 70.0 | 10.5 | 4.6 |
| 17 | (F7) | 0.1127 | 0.68 | 71.1 | 18.1 | 8.7 |
| 18 | (F8) | 0.1179 | 0.66 | 71.4 | 14.5 | 6.8 |
| 19 | (F9) | 0.1115 | 0.65 | 70.4 | 15.5 | 7.1 |
| 20 | (F10) | 0.1058 | 0.64 | 70.7 | 21.2 | 9.6 |

The invention claimed is:

1. An organic dye having general formula (I):

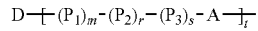

(I)

wherein:

$P_1$, $P_2$ and $P_3$, the same or different, are selected from bivalent heteroaryl groups having the following general formulae (VII), (VIII), (IX), (XII), with the proviso that at least one of $P_1$, $P_2$ and $P_3$, is selected from bivalent heteroaryl groups having general formula (VII):

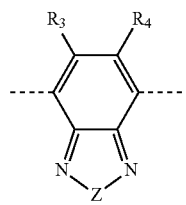

(IX)

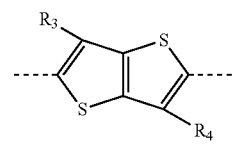

(VII)

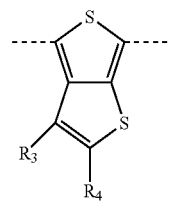

(VIII)

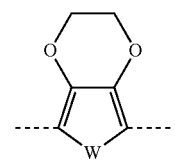

(XII)

wherein:

$R_3$ and $R_4$, the same or different, represent a hydrogen atom; or they represent a halogen atom selected from fluorine, chlorine or bromine; or they are selected from linear or branched $C_1$-$C_{20}$ alkyl groups, saturated or unsaturated, optionally containing heteroatoms, aryl groups optionally substituted, heteroaryl groups optionally substituted, cycloalkyl groups optionally substituted, heterocyclic groups optionally substituted, trialkyl- or triaryl-silyl groups, dialkyl- or diaryl-amine groups, dialkyl- or diaryl phosphinic groups, linear or branched $C_1$-$C_{20}$ alkoxyl groups, saturated or unsaturated, aryloxyl groups optionally substituted, thioalkoxyl or thioaryloxyl groups optionally substituted, cyano groups;

Z represents a heteroatom selected from oxygen, sulfur, selenium, tellurium; or it is selected from groups having general formula X($R_5$) or from groups having general formula Y($R_6R_7$), wherein $R_5$, $R_6$ and $R_7$, have the meanings specified hereunder, X represents a heteroatom selected from nitrogen, phosphorous, arsenic, boron, Y represents a carbon, silicon, or germanium atom;

W represents a heteroatom selected from oxygen, sulfur, selenium, tellurium; or it is selected from groups having general formula Y(R$_6$R$_7$) wherein R$_6$ and R$_7$, have the meanings specified hereunder, Y represents a carbon, silicon, or germanium atom;

R$_5$ represents a hydrogen atom; or it is selected from linear or branched C$_1$-C$_{20}$ alkyl groups, saturated or unsaturated, optionally containing heteroatoms, aryl groups optionally substituted, cycloalkyl groups optionally substituted;

R$_6$ and R$_7$, the same or different, are selected from linear or branched C$_1$-C$_{20}$ alkyl groups, saturated or unsaturated, optionally containing heteroatoms, aryl groups optionally substituted, cycloalkyl groups optionally substituted, linear or branched C$_1$-C$_{20}$ alkoxyl groups, saturated or unsaturated, aryloxyl groups optionally substituted, thioalkoxyl or thioaryloxyl groups optionally substituted;

or R$_3$ and R$_4$, in general formulae (VIII) or (IX), can be optionally bound to each other so as to form, together with the other atoms to which they are bound, a cycle containing from 1 to 12 carbon atoms, saturated, unsaturated, or aromatic, optionally substituted with linear or branched C$_1$-C$_{20}$ alkyl groups, saturated or unsaturated, optionally containing heteroatoms, aryl groups optionally substituted, heteroaryl groups optionally substituted, cycloalkyl groups optionally substituted, heterocyclic groups optionally substituted, trialkyl- or triaryl-silyl groups, dialkyl- or diaryl-amine groups, dialkyl- or diaryl phosphinic groups, linear or branched C$_1$-C$_{20}$ alkoxyl groups, saturated or unsaturated, aryloxyl groups optionally substituted, thioalkoxyl or thioaryloxyl groups optionally substituted, cyano groups, said cycle optionally containing heteroatoms selected from oxygen, sulfur, nitrogen, silicon, phosphorous, selenium;

m, r and s, the same or different, are an integer ranging from 0 to 5, with the proviso that at least one of m, r and s is different from 0, and that at least one of m, r and s is different from 0 for said at least one of P$_1$, P$_2$ and P$_3$ that is selected from bivalent heteroaryl groups having general formula (VII);

A represents a group —COOH; a phosphonic group having formula —PO(OH)$_2$ or —PO(OH)(R), wherein R is selected from linear or branched C$_1$-C$_{20}$ alkyl groups; a carboxycyanovinylene group having general formula (XIII) or (XIV):

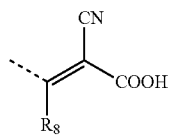

(XIII)

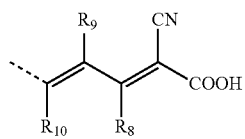

(XIV)

wherein R$_8$, R$_9$ and R$_{10}$, the same or different, represent a hydrogen atom; or they represent a halogen atom selected from fluorine, chlorine or bromine; or they are selected from linear or branched C$_1$-C$_{20}$ alkyl groups, saturated or unsaturated, optionally containing heteroatoms, aryl groups optionally substituted, heteroaryl groups optionally substituted, cycloalkyl groups optionally substituted, cyano groups, nitro groups;

t is an integer ranging from 2 to 6;

D represents a triarylamine group having the following general formulae (XV), (XVI), (XVII), (XVIII), (XIX), (XX), (XXI), (XXII), (XXIII), (XXIV):

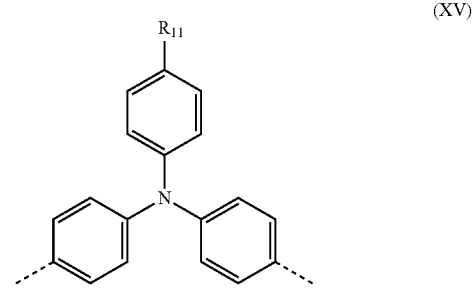

(XV)

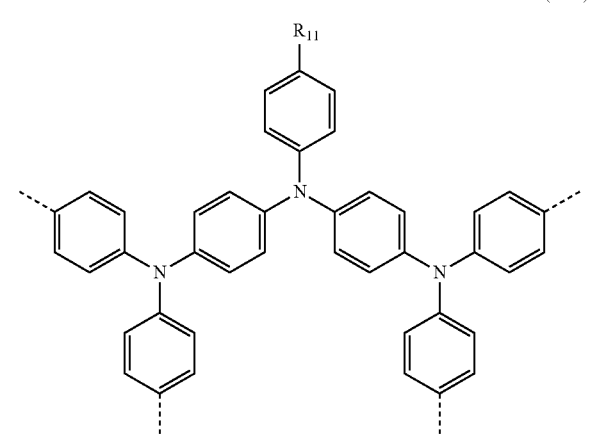

(XVI)

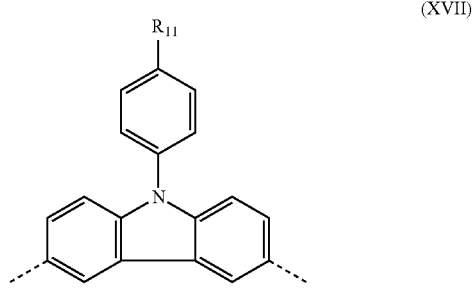

(XVII)

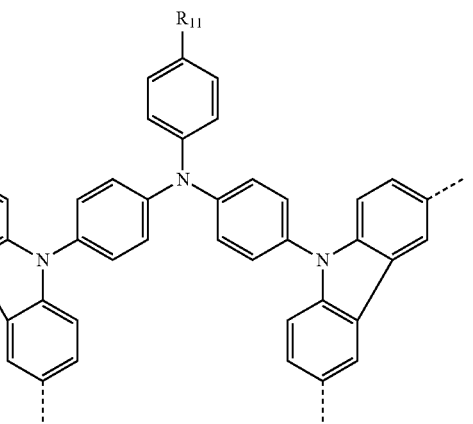

(XVIII)

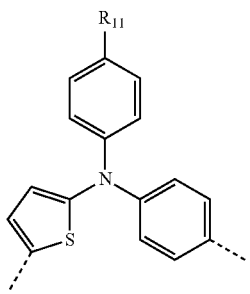
(XIX)

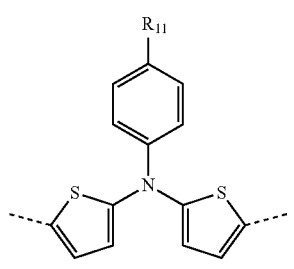
(XX)

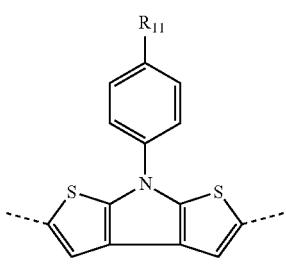
(XXI)

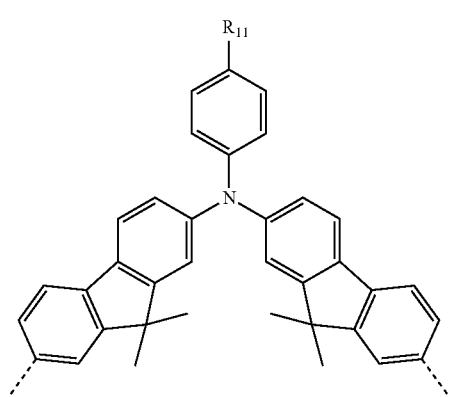
(XXII)

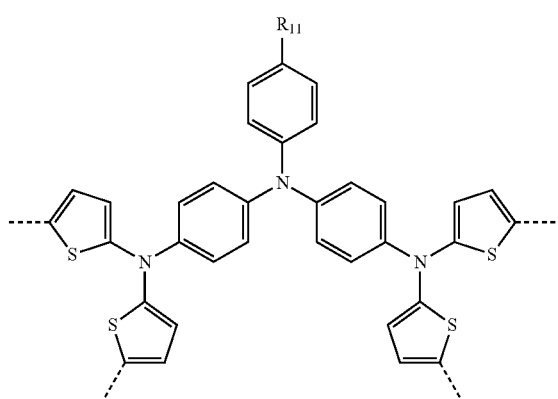
(XXIII)

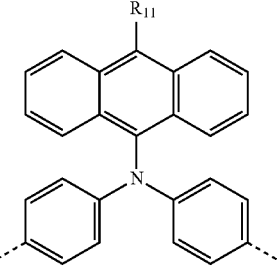
(XXIV)

wherein $R_{11}$ represents an hydrogen atom or it is selected from polyethyleneoxyl groups having formula $R'\!-\!O\!-\![-\!CH_2\!-\!CH_2\!-\!O]_q\!-$ wherein $R'$ represents a hydrogen atom; or it is selected from linear or branched $C_1$-$C_{20}$ alkyl groups, and q is an integer ranging from 1 to 20, heteroaryl groups optionally substituted.

2. A dye-sensitized photoelectric transformation element, comprising at least one organic dye having general formula (I) according to claim 1, said dye-sensitized photoelectric transformation element being supported on particles of a semiconductor oxide.

3. A Dye-Sensitized Solar Cell (DSSC) comprising the dye-sensitized photoelectric transformation element according to claim 2.

4. An organic dye having general formula (I):

(I)

wherein:
  $P_1$, $P_2$ and $P_3$, the same or different, are selected from bivalent heteroaryl groups having the following general formulae (VII), (VIII), (IX), (XII), with the proviso that at least one of $P_1$, $P_2$ and $P_3$, is selected from bivalent heteroaryl groups having general formula (VII):

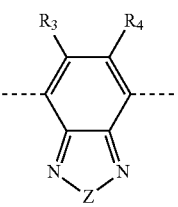
(IX)

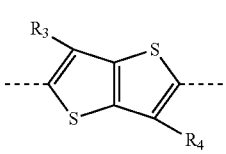
(VII)

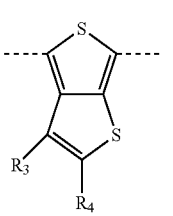
(VIII)

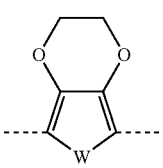

(XII)

wherein:
R₃ and R₄, the same or different, represent a hydrogen atom; or they represent a halogen atom selected from fluorine, chlorine or bromine; or they are selected from linear or branched $C_1$-$C_{20}$ alkyl groups, saturated or unsaturated, optionally containing heteroatoms, aryl groups optionally substituted, heteroaryl groups optionally substituted, cycloalkyl groups optionally substituted, heterocyclic groups optionally substituted, trialkyl- or triaryl-silyl groups, dialkyl- or diaryl-amine groups, dialkyl- or diaryl phosphinic groups, linear or branched $C_1$-$C_{20}$ alkoxyl groups, saturated or unsaturated, aryloxyl groups optionally substituted, thioalkoxyl or thioaryloxyl groups optionally substituted, cyano groups;

Z represents a heteroatom selected from oxygen, sulfur, selenium, tellurium; or it is selected from groups having general formula X(R₅) or from groups having general formula Y(R₆R₇), wherein R₅, R⁶ and R₇, have the meanings specified hereunder, X represents a heteroatom selected from nitrogen, phosphorous, arsenic, boron, Y represents a carbon, silicon, or germanium atom;

W represents a heteroatom selected from oxygen, sulfur, selenium, tellurium; or it is selected from groups having general formula Y(R₆R₇) wherein R₆ and R₇, have the meanings specified hereunder, Y represents a carbon, silicon, or germanium atom;

R₅ represents a hydrogen atom; or it is selected from linear or branched $C_1$-$C_{20}$ alkyl groups, saturated or unsaturated, optionally containing heteroatoms, aryl groups optionally substituted, cycloalkyl groups optionally substituted;

R₆ and R₇, the same or different, are selected from linear or branched $C_1$-$C_{20}$ alkyl groups, saturated or unsaturated, optionally containing heteroatoms, aryl groups optionally substituted, cycloalkyl groups optionally substituted, linear or branched $C_1$-$C_{20}$ alkoxyl groups, saturated or unsaturated, aryloxyl groups optionally substituted, thioalkoxyl or thioaryloxyl groups optionally substituted;

or R₃ and R₄, in general formulae (VIII) or (IX), can be optionally bound to each other so as to form, together with the other atoms to which they are bound, a cycle containing from 1 to 12 carbon atoms, saturated, unsaturated, or aromatic, optionally substituted with linear or branched $C_1$-$C_{20}$ alkyl groups, saturated or unsaturated, optionally containing heteroatoms, aryl groups optionally substituted, heteroaryl groups optionally substituted, cycloalkyl groups optionally substituted, heterocyclic groups optionally substituted, trialkyl- or triaryl-silyl groups, dialkyl- or diaryl-amine groups, dialkyl- or diaryl phosphinic groups, linear or branched $C_1$-$C_{20}$ alkoxyl groups, saturated or unsaturated, aryloxyl groups optionally substituted, thioalkoxyl or thioaryloxyl groups optionally substituted, cyano groups, said cycle optionally containing heteroatoms selected from oxygen, sulfur, nitrogen, silicon, phosphorous, selenium;

m, r and s, the same or different, are an integer ranging from 0 to 5, with the proviso that at least one of m, r and s is different from 0, and that at least one of m, r and s is different from 0 for said at least one of $P_1$, $P_2$ and $P_3$ that is selected from bivalent heteroaryl groups having general formula (VII);

A represents a carboxycyanovinylene group having general formula (XIII):

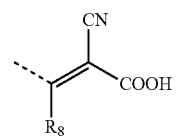

(XIII)

wherein R₈ represents a hydrogen atom;
t is 2;
D represents a triarylamine group having general formula (XV):

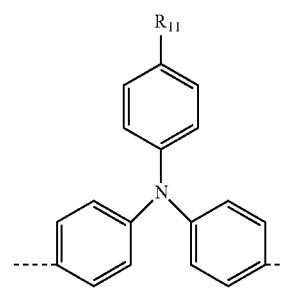

(XV)

wherein R₁₁ represents an hydrogen atom; or it is selected from polyethyleneoxyl groups having formula R'—O—[—CH₂—CH₂—O]_q— wherein R' represents a hydrogen atom; or it is selected from linear or branched $C_1$-$C_{20}$ alkyl groups, and q is an integer ranging from 1 to 20; or R' is an aryl group optionally substituted with one or more groups, the same or different, selected from: $C_1$-$C_{16}$ alkyl groups, $C_1$-$C_{16}$ alkoxyl groups, $C_1$-$C_{16}$ thioalkoxyl groups, $C_3$-$C_{24}$ tri-alkylsilyl groups, polyethyleneoxyl groups, amino groups, $C_1$-$C_{16}$ mono- or di-alkylamine groups; or R' is a heteroaryl group containing from 1 to 4 heteroatoms selected from nitrogen, oxygen, sulfur, silicon, selenium, phosphorous, optionally substituted with one or more groups, the same or different, selected from $C_1$-$C_{16}$ alkyl groups, $C_1$-$C_{16}$ alkoxyl groups, $C_1$-$C_{16}$ thioalkoxyl groups, $C_3$-$C_{24}$ tri-alkylsilyl groups, polyethyleneoxyl groups, amino groups, $C_1$-$C_{16}$ mono- or di-alkylamine groups.

5. A dye-sensitized photoelectric transformation element, comprising at least one organic dye having general formula (I) according to claim 4, said dye-sensitized photoelectric transformation element being supported on particles of a semiconductor oxide.

6. A Dye-Sensitized Solar Cell (DSSC) comprising the dye-sensitized photoelectric transformation element according to claim 5.

7. An organic dye having general formula (I):

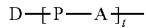   (I)

wherein:
P represents one of the following general formulae (Ia), (Ib), (Ic), (Id):

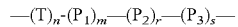   (Ia)

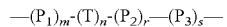   (Ib)

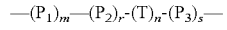   (Ic)

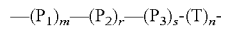   (Id)

wherein:
T represents a triple carbon-carbon bond having formula (II), or a double carbon-carbon bond having general formula (III) or (IV):

   (II)

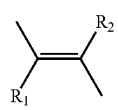   (III)

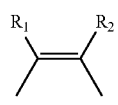   (IV)

wherein $R_1$ and $R_2$, the same or different, represent a hydrogen atom; or they are selected from linear or branched $C_1$-$C_{20}$ alkyl groups, saturated or unsaturated, optionally containing heteroatoms, aryl groups optionally substituted, heteroaryl groups optionally substituted, cycloalkyl groups optionally substituted;

n is an integer ranging from 0 to 5;

$P_1$, $P_2$ and $P_3$, the same or different, are selected from bivalent heteroaryl groups having the following general formulae (VIII), (IX), (XII), with the proviso that at least one of $P_1$, $P_2$ and $P_3$, is selected from bivalent heteroaryl groups having general formula (VIII) or (IX):

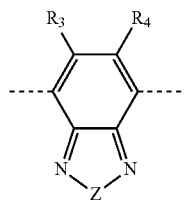   (IX)

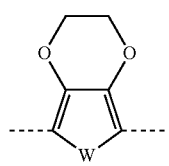   (XII)

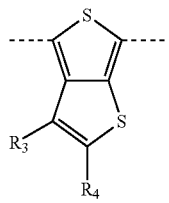   (VIII)

wherein:
$R_3$ and $R_4$, the same or different, represent a hydrogen atom; or they represent a halogen atom selected from fluorine, chlorine or bromine; or they are selected from linear or branched $C_1$-$C_{20}$ alkyl groups, saturated or unsaturated, optionally containing heteroatoms, aryl groups optionally substituted, heteroaryl groups optionally substituted, cycloalkyl groups optionally substituted, heterocyclic groups optionally substituted, trialkyl- or triaryl-silyl groups, dialkyl- or diaryl-amine groups, dialkyl- or diaryl phosphinic groups, linear or branched $C_1$-$C_{20}$ alkoxyl groups, saturated or unsaturated, aryloxyl groups optionally substituted, thioalkoxyl or thioaryloxyl groups optionally substituted, cyano groups;

Z represents a heteroatom selected from oxygen, sulfur, selenium, tellurium; or it is selected from groups having general formula $X(R_5)$ or from groups having general formula $Y(R_6R_7)$, wherein $R_5$, $R_6$ and $R_7$, have the meanings specified hereunder, X represents a heteroatom selected from nitrogen, phosphorous, arsenic, boron, Y represents a carbon, silicon, or germanium atom;

W represents a heteroatom selected from oxygen, sulfur, selenium, tellurium; or it is selected from groups having general formula $Y(R_6R_7)$ wherein $R_6$ and $R_7$, have the meanings specified hereunder, Y represents a carbon, silicon, or germanium atom;

$R_5$ represents a hydrogen atom; or it is selected from linear or branched $C_1$-$C_{20}$ alkyl groups, saturated or unsaturated, optionally containing heteroatoms, aryl groups optionally substituted, cycloalkyl groups optionally substituted;

$R_6$ and $R_7$, the same or different, are selected from linear or branched $C_1$-$C_{20}$ alkyl groups, saturated or unsaturated, optionally containing heteroatoms, aryl groups optionally substituted, cycloalkyl groups optionally substituted, linear or branched $C_1$-$C_{20}$ alkoxyl groups, saturated or unsaturated, aryloxyl groups optionally substituted, thioalkoxyl or thioaryloxyl groups optionally substituted;

or $R_3$ and $R_4$, in general formulae (VIII) or (IX), can be optionally bound to each other so as to form, together with the other atoms to which they are bound, a cycle containing from 1 to 12 carbon atoms, saturated, unsaturated, or aromatic, optionally substituted with linear or branched $C_1$-$C_{20}$ alkyl groups, saturated or unsaturated, optionally containing heteroatoms, aryl groups optionally substituted, heteroaryl groups optionally substituted, cycloalkyl groups optionally substituted, heterocyclic groups optionally substituted, trialkyl- or triaryl-silyl groups, dialkyl- or diaryl-amine groups, dialkyl- or diaryl phosphinic groups, linear or branched $C_1$-$C_{20}$ alkoxyl groups, saturated or unsaturated, aryloxyl groups optionally substituted, thioalkoxyl or thioaryloxyl groups optionally substituted, cyano groups, said cycle optionally containing heteroatoms selected from oxygen, sulfur, nitrogen, silicon, phosphorous, selenium;

m, r and s, the same or different, are an integer ranging from 0 to 5, with the proviso that at least one of m, r and s is different from 0, and that at least one of m, r and s is different from 0 for said at least one of $P_1$, $P_2$ and $P_3$ that is selected from bivalent heteroaryl groups having general formula (VIII) or (IX);

A represents a group —COOH; a phosphonic group having formula —PO(OH)$_2$ or —PO(OH)(R), wherein R is selected from linear or branched $C_1$-$C_{20}$ alkyl groups; a carboxycyanovinylene group having general formula (XIII) or (XIV):

(XV)

(XVI)

(XVII)

(XVIII)
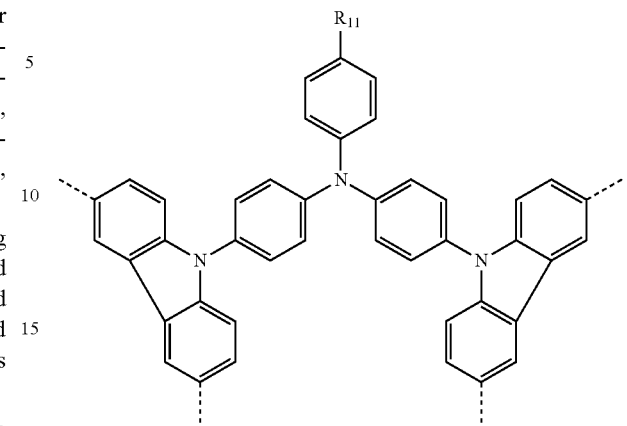

(XIX)
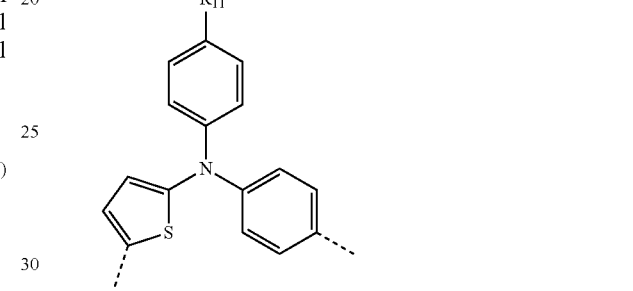

(XX)
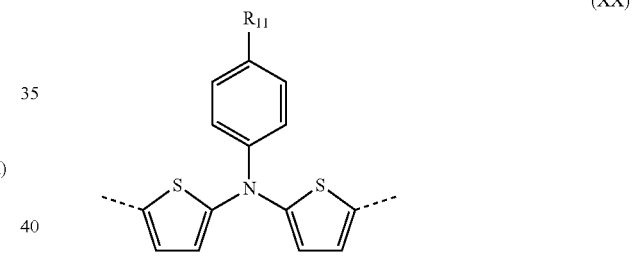

(XXI)
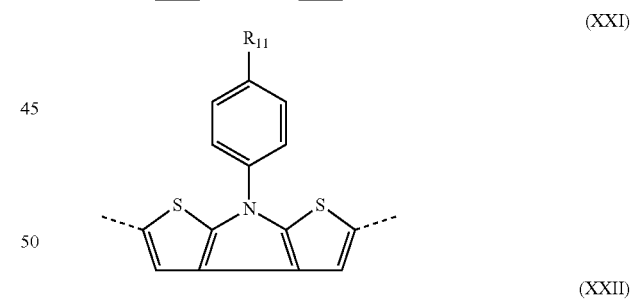

(XXII)
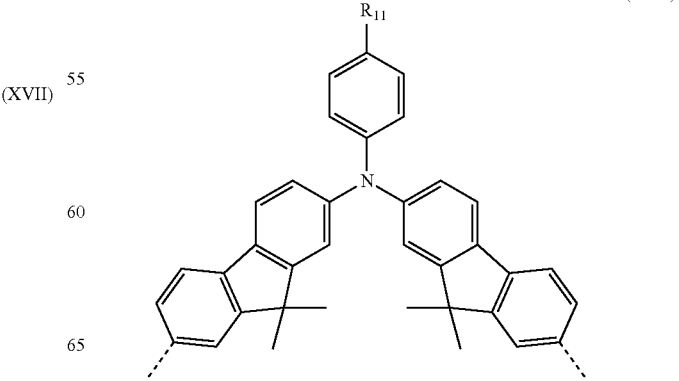

(XXIII)

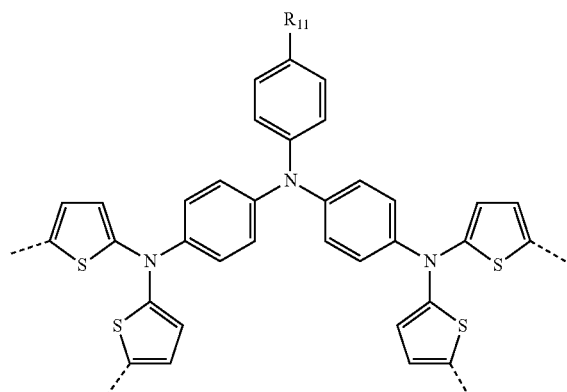

(XXIV)

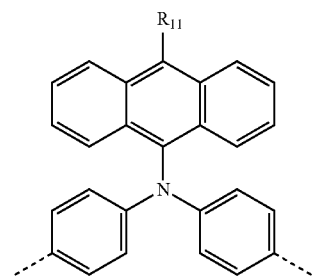

wherein $R_8$, $R_9$ and $R_{10}$, the same or different, represent a hydrogen atom; or they represent a halogen atom selected from fluorine, chlorine or bromine; or they are selected from linear or branched $C_1$-$C_{20}$ alkyl groups, saturated or unsaturated, optionally containing heteroatoms, aryl groups optionally substituted, heteroaryl groups optionally substituted, cycloalkyl groups optionally substituted, cyano groups, nitro groups;

t is an integer ranging from 2 to 6;

D represents a triarylamine group having the following general formulae (XV), (XVI), (XVII), (XVIII), (XIX), (XX), (XXI), (XXII), (XXIII), (XXIV):

(XV)

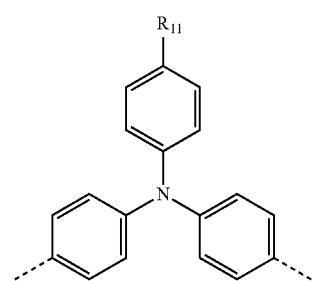

(XVI)

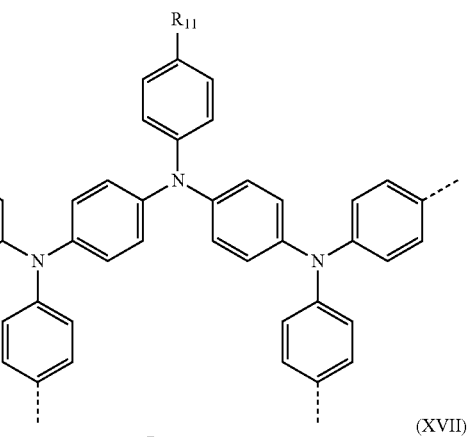

(XVII)

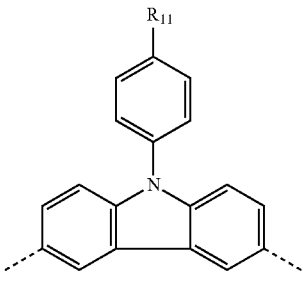

(XVIII)

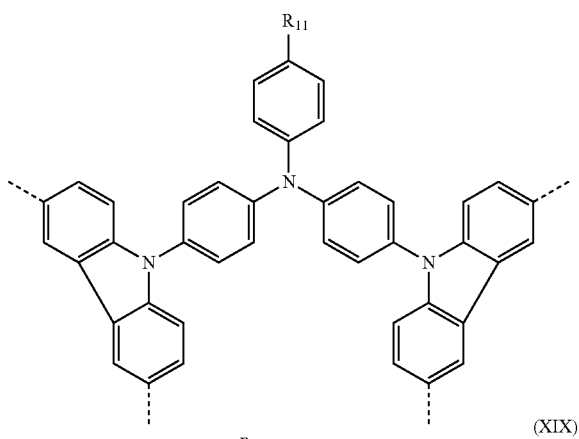

(XIX)

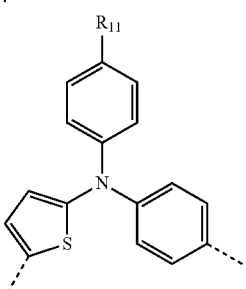

(XX)

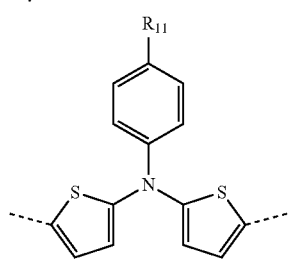

-continued

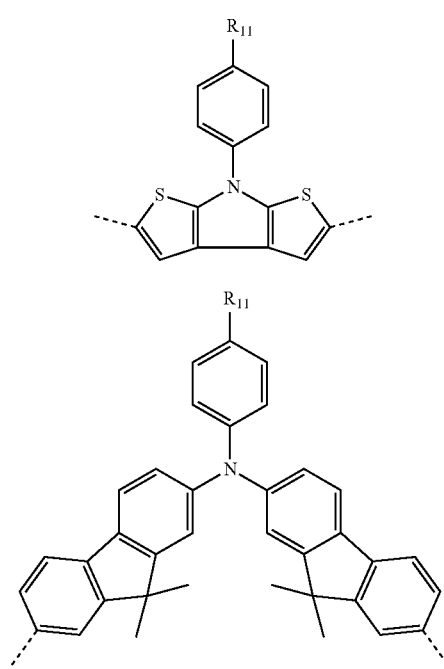

(XXI)

(XXII)

(XXIII)

-continued

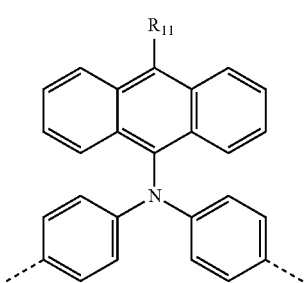

(XXIV)

wherein $R_{11}$ represents an hydrogen atom or it is selected from linear or branched $C_1$-$C_{20}$ alkyl groups, saturated or unsaturated, optionally containing heteroatoms, linear or branched $C_1$-$C_{20}$ alkoxyl groups, saturated or unsaturated, polyethyleneoxyl groups having formula R'—O—[—CH$_2$—CH$_2$—O]$_q$— wherein R' represents a hydrogen atom; or it is selected from linear or branched $C_1$-$C_{20}$ alkyl groups, and q is an integer ranging from 1 to 20, aryl groups optionally substituted, heteroaryl groups optionally substituted, cycloalkyl groups optionally substituted, heterocyclic groups optionally substituted, trialkyl- or triaryl-silyl groups, dialkyl- or diaryl-amine groups, dialkyl- or diaryl phosphinic groups, linear or branched $C_1$-$C_{20}$ alkoxyl groups, saturated or unsaturated, aryloxyl groups optionally substituted, thioalkoxyl or thioaryloxyl groups optionally substituted.

8. A dye-sensitized photoelectric transformation element, comprising at least one organic dye having general formula (I) according to claim 7, said dye-sensitized photoelectric transformation element being supported on particles of a semiconductor oxide.

9. A Dye-Sensitized Solar Cell (DSSC) comprising the dye-sensitized photoelectric transformation element according to claim 8.

* * * * *

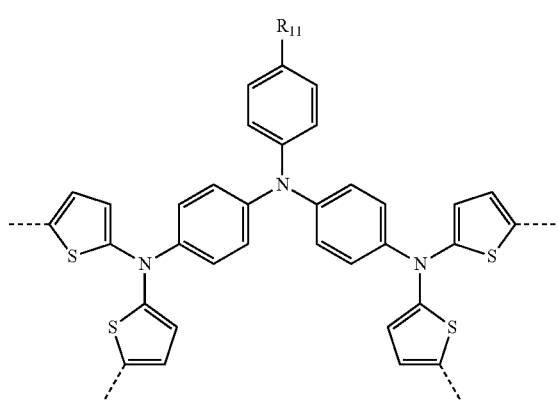

UNITED STATES PATENT AND TRADEMARK OFFICE
CERTIFICATE OF CORRECTION

PATENT NO. : 9,660,196 B2
APPLICATION NO. : 14/428659
DATED : May 23, 2017
INVENTOR(S) : Alessandro Abbotto et al.

Page 1 of 1

It is certified that error appears in the above-identified patent and that said Letters Patent is hereby corrected as shown below:

In the Claims

On Column 97, directly following Line 23 which reads: "formula (XIII) or (XIV):" all the way through Column 99, Line 35, delete all chemical formulas:
"(XV), (XVI), (XVII), (XVIII), (XIX), (XX), (XXI), (XXII), (XXIII), (XXIV)"

And insert instead the following chemical formulas (XIII) and (XIV) in their place:

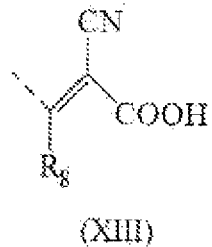 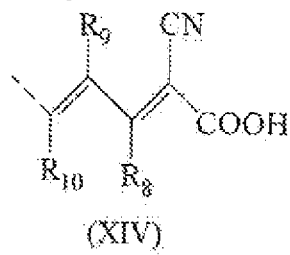

The next line will continue with the current Column 99, Line 39, which reads:
"wherein R8, R9 and R10, the same or different, represent a"

Signed and Sealed this
Fourteenth Day of November, 2017

Joseph Matal
*Performing the Functions and Duties of the
Under Secretary of Commerce for Intellectual Property and
Director of the United States Patent and Trademark Office*